(12) United States Patent
Gray et al.

(10) Patent No.: US 11,369,489 B2
(45) Date of Patent: Jun. 28, 2022

(54) DECOUPLED SPACER AND PLATE AND METHOD OF INSTALLING THE SAME

(71) Applicant: GLOBUS MEDICAL, INC., Audubon, PA (US)

(72) Inventors: Jason Gray, East Greenville, PA (US); Mark Fromhold, Phoenixville, PA (US); Brittany Hansen, Philadelphia, PA (US); Mark Miccio, Lynbrook, NY (US); Morgan Kunkle, Philadelphia, PA (US); Matthew Urban, Mont Clare, PA (US); Jason Zappacosta, Philadelphia, PA (US); Noah Hansell, King of Prussia, PA (US); Mark Adams, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 309 days.

(21) Appl. No.: 16/458,467

(22) Filed: Jul. 1, 2019

(65) Prior Publication Data

US 2019/0321199 A1 Oct. 24, 2019

Related U.S. Application Data

(63) Continuation of application No. 15/479,438, filed on Apr. 5, 2017, now Pat. No. 10,376,385.

(51) Int. Cl.
*A61F 2/44* (2006.01)
*A61F 2/46* (2006.01)
*A61B 17/70* (2006.01)
*A61B 17/80* (2006.01)

(52) U.S. Cl.
CPC ........ *A61F 2/4611* (2013.01); *A61B 17/7059* (2013.01); *A61B 17/8042* (2013.01); *A61F 2/4455* (2013.01)

(58) Field of Classification Search
None
See application file for complete search history.

(56) References Cited

U.S. PATENT DOCUMENTS

| 1,673,630 | A | 6/1928 | Madge |
| 2,363,405 | A | 11/1944 | Eichelberger |
| 2,596,957 | A | 5/1952 | Olson |
| 4,599,086 | A | 7/1986 | Doty |

(Continued)

FOREIGN PATENT DOCUMENTS

| FR | 2727003 A1 | 5/1996 |
| JP | 2012-508043 A | 4/2012 |

(Continued)

OTHER PUBLICATIONS

Guidance Document: Intervertebral Body Fusion Device, U.S. Dept. of Health and Human Services, Food and Drug Administration (Jun. 12, 2007).

(Continued)

*Primary Examiner* — Sameh R Boles

(57) ABSTRACT

Intervertebral spacer assemblies, systems, and methods thereof. A method of insertion includes inserting an intervertebral spacer and plate together using an insertion tool and, upon removal of the insertion tool, the intervertebral spacer and plate are no longer considered connected/coupled and act as separate components.

18 Claims, 60 Drawing Sheets

(56) References Cited

U.S. PATENT DOCUMENTS

| | | |
|---|---|---|
| 4,743,256 A | 5/1988 | Brantigan |
| 4,955,908 A | 9/1990 | Frey |
| 5,002,576 A | 3/1991 | Fuhrmann |
| 5,364,399 A | 11/1994 | Lowery |
| 5,397,364 A | 3/1995 | Kozak |
| 5,458,641 A | 10/1995 | Jiminez |
| 5,514,180 A | 5/1996 | Heggeness |
| 5,549,612 A | 8/1996 | Yapp et al. |
| 5,609,635 A | 3/1997 | Michelson |
| 5,728,159 A | 3/1998 | Stroever |
| 5,741,253 A | 4/1998 | Michelson |
| 5,814,084 A | 9/1998 | Grivas |
| 5,861,041 A | 1/1999 | Tienboon |
| 5,888,223 A | 3/1999 | Bray, Jr. |
| 5,888,227 A | 3/1999 | Cottle |
| 5,899,939 A | 5/1999 | Boyce |
| 5,972,368 A | 10/1999 | Mckay |
| 5,989,289 A | 11/1999 | Coates |
| 6,025,538 A | 2/2000 | Yaccarino, III |
| 6,033,438 A | 3/2000 | Bianchi |
| 6,045,579 A | 4/2000 | Hochshuler |
| 6,066,175 A | 5/2000 | Henderson et al. |
| 6,096,081 A | 8/2000 | Grivas |
| 6,143,033 A | 11/2000 | Paul |
| 6,146,421 A | 11/2000 | Gordon |
| 6,156,037 A | 12/2000 | LeHuec et al. |
| 6,174,311 B1 | 1/2001 | Branch |
| 6,200,347 B1 | 3/2001 | Anderson et al. |
| 6,206,922 B1 | 3/2001 | Zdeblick et al. |
| 6,206,923 B1 | 3/2001 | Boyd |
| 6,231,610 B1 | 5/2001 | Geisler |
| 6,235,059 B1 | 5/2001 | Benezech |
| 6,245,108 B1 | 6/2001 | Biscup |
| 6,258,089 B1 | 7/2001 | Campbell et al. |
| 6,258,125 B1 | 7/2001 | Paul |
| 6,261,586 B1 | 7/2001 | Mckay |
| 6,270,528 B1 | 8/2001 | Mckay |
| 6,294,187 B1 | 9/2001 | Boyce |
| 6,342,074 B1 | 1/2002 | Simpson |
| 6,350,283 B1 | 2/2002 | Michelson |
| 6,364,880 B1 | 4/2002 | Michelson |
| 6,371,988 B1 | 4/2002 | Pafford |
| 6,379,385 B1 | 4/2002 | Kalas |
| 6,383,186 B1 | 5/2002 | Michelson |
| 6,398,811 B1 | 6/2002 | Mckay |
| 6,409,765 B1 | 6/2002 | Bianchi |
| 6,432,106 B1 | 8/2002 | Fraser |
| 6,432,436 B1 | 8/2002 | Gertzman |
| 6,458,158 B1 | 10/2002 | Anderson |
| 6,468,311 B2 | 10/2002 | Boyd |
| 6,471,724 B2 | 10/2002 | Zdeblick |
| 6,482,233 B1 | 11/2002 | Aebi |
| 6,511,509 B1 | 1/2003 | Ford |
| 6,520,993 B2 | 2/2003 | James |
| 6,540,785 B1 | 4/2003 | Gill et al. |
| 6,548,080 B1 | 4/2003 | Gertzman |
| 6,554,863 B2 | 4/2003 | Paul |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,579,318 B2 | 6/2003 | Varga |
| 6,610,065 B1 | 8/2003 | Branch |
| 6,629,998 B1 | 10/2003 | Lin |
| 6,632,247 B2 | 10/2003 | Boyer, II |
| 6,638,310 B2 | 10/2003 | Lin |
| 6,652,593 B2 | 11/2003 | Boyer, II |
| 6,660,038 B2 | 12/2003 | Boyer, II |
| 6,666,889 B1 | 12/2003 | Commarmond |
| 6,666,890 B2 | 12/2003 | Michelson |
| 6,676,703 B2 | 1/2004 | Biscup |
| 6,682,563 B2 | 1/2004 | Scharf |
| 6,695,882 B2 | 2/2004 | Bianchi |
| 6,706,067 B2 | 3/2004 | Shimp |
| 6,709,458 B2 | 3/2004 | Michelson |
| 6,719,794 B2 | 4/2004 | Gerber |
| 6,730,127 B2 | 5/2004 | Michelson |
| 6,740,118 B2 | 5/2004 | Eisermann et al. |
| 6,761,738 B1 | 7/2004 | Boyd |
| 6,761,739 B2 | 7/2004 | Shepard |
| 6,764,491 B2 | 7/2004 | Frey |
| 6,767,369 B2 | 7/2004 | Boyer, II |
| 6,776,800 B2 | 8/2004 | Boyer, II |
| 6,793,658 B2 | 9/2004 | LeHuec |
| RE38,614 E | 10/2004 | Paul |
| 6,805,714 B2 | 10/2004 | Sutcliffe |
| 6,808,585 B2 | 10/2004 | Boyce |
| 6,827,740 B1 | 12/2004 | Michelson |
| 6,830,570 B1 | 12/2004 | Frey |
| 6,835,206 B2 | 12/2004 | Jackson |
| 6,849,093 B2 | 2/2005 | Michelson |
| 6,852,126 B2 | 2/2005 | Ahlgren |
| 6,855,167 B2 | 2/2005 | Shimp |
| 6,855,169 B2 | 2/2005 | Boyer, II |
| 6,887,272 B2 | 4/2005 | Shinomiya |
| 6,899,735 B2 | 5/2005 | Coates et al. |
| 6,902,578 B1 | 6/2005 | Anderson |
| 6,929,662 B1 | 8/2005 | Messerli |
| 6,972,019 B2 | 12/2005 | Michelson |
| 6,974,480 B2 | 12/2005 | Messerli |
| 6,986,788 B2 | 1/2006 | Paul |
| 7,001,432 B2 | 2/2006 | Keller et al. |
| 7,014,659 B2 | 3/2006 | Boyer, II |
| 7,018,412 B2 | 3/2006 | Ferreira |
| 7,018,413 B2 | 3/2006 | Krüger |
| 7,022,137 B2 | 4/2006 | Michelson |
| 7,025,787 B2 | 4/2006 | Bryan et al. |
| 7,044,968 B1 | 5/2006 | Yaccarino, III et al. |
| 7,044,972 B2 | 5/2006 | Mathys |
| 7,048,762 B1 | 5/2006 | Sander |
| 7,048,765 B1 | 5/2006 | Grooms |
| 7,060,073 B2 | 6/2006 | Frey |
| 7,060,096 B1 | 6/2006 | Schopf |
| 7,087,082 B2 | 8/2006 | Paul |
| 7,087,087 B2 | 8/2006 | Boyer, II |
| 7,112,222 B2 | 9/2006 | Fraser |
| 7,115,146 B2 | 10/2006 | Boyer, II |
| 7,137,997 B2 | 11/2006 | Paul |
| 7,147,665 B1 | 12/2006 | Bryan et al. |
| 7,153,325 B2 | 12/2006 | Kim et al. |
| 7,163,561 B2 | 1/2007 | Michelson |
| 7,172,627 B2 | 2/2007 | Fiere |
| 7,192,447 B2 | 3/2007 | Rhoda |
| 7,223,292 B2 | 5/2007 | Messerli |
| 7,226,482 B2 | 6/2007 | Messerli |
| 7,226,483 B2 | 6/2007 | Gerber |
| 7,229,477 B2 | 6/2007 | Biscup |
| 7,232,464 B2 | 6/2007 | Mathieu |
| 7,235,105 B2 | 6/2007 | Jackson |
| 7,238,203 B2 | 7/2007 | Bagga |
| 7,276,082 B2 | 10/2007 | Zdeblick et al. |
| 7,300,465 B2 | 11/2007 | Paul |
| 7,309,357 B2 | 12/2007 | Kim |
| 7,309,359 B2 | 12/2007 | Trieu |
| 7,320,708 B1 | 1/2008 | Bernstein |
| 7,323,011 B2 | 1/2008 | Shepard |
| 7,347,873 B2 | 3/2008 | Paul |
| 7,435,262 B2 | 10/2008 | Michelson |
| 7,473,277 B2 | 1/2009 | Boyer, II |
| 7,479,160 B2 | 1/2009 | Branch |
| 7,481,812 B2 | 1/2009 | Frey |
| 7,491,237 B2 | 2/2009 | Randall |
| 7,594,931 B2 | 9/2009 | Louis |
| 7,601,173 B2 | 10/2009 | Messerli |
| 7,618,456 B2 | 11/2009 | Mathieu |
| 7,618,460 B2 | 11/2009 | Boyd |
| 7,637,953 B2 | 12/2009 | Branch |
| 7,662,184 B2 | 2/2010 | Edwards |
| 7,662,185 B2 | 2/2010 | Alfaro |
| 7,726,002 B2 | 6/2010 | Shimp |
| 7,753,963 B2 | 7/2010 | Boyer, II |
| 7,771,475 B2 | 8/2010 | Michelson |
| 7,794,502 B2 | 9/2010 | Michelson |
| 7,815,682 B1 | 10/2010 | Peterson |

(56) References Cited

U.S. PATENT DOCUMENTS

| | | |
|---|---|---|
| 7,833,271 B2 | 11/2010 | Mitchell |
| 7,846,207 B2 | 12/2010 | Lechmann |
| 7,850,731 B2 | 12/2010 | Brittan |
| 7,862,616 B2 | 1/2011 | Lechmann |
| 7,875,076 B2 | 1/2011 | Mathieu |
| 7,879,103 B2 | 1/2011 | Gertzman |
| 7,918,888 B2 | 4/2011 | Hamada |
| 7,931,692 B2 | 4/2011 | Sybert |
| 7,938,857 B2 | 5/2011 | Garcia-bengochea |
| 7,967,867 B2 | 6/2011 | Barreiro |
| 7,972,381 B2 | 7/2011 | Michelson |
| 8,002,833 B2 | 8/2011 | Fabris Monterumici |
| 8,100,976 B2 | 1/2012 | Bray et al. |
| 8,105,383 B2 | 1/2012 | Michelson |
| 8,114,162 B1 | 2/2012 | Bradley |
| 8,273,127 B2 | 9/2012 | Jones |
| 8,323,343 B2 | 12/2012 | Michelson |
| 8,328,872 B2 | 12/2012 | Duffield |
| 8,343,222 B2 | 1/2013 | Cope |
| 8,366,776 B2 | 2/2013 | Heinz |
| 8,435,300 B2 | 5/2013 | Messerli et al. |
| 8,709,085 B2 | 4/2014 | Lechmann |
| 8,840,667 B1 | 9/2014 | Tumialan |
| 8,956,416 B2 | 2/2015 | McCarthy |
| 9,180,022 B2 * | 11/2015 | Georges ............ A61B 17/7059 |
| 2001/0010021 A1 | 7/2001 | Boyd |
| 2002/0010511 A1 | 1/2002 | Michelson |
| 2002/0016595 A1 | 2/2002 | Michelson |
| 2002/0106393 A1 | 8/2002 | Bianchi |
| 2002/0138143 A1 | 9/2002 | Grooms |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2004/0078078 A1 | 4/2004 | Shepard |
| 2004/0143270 A1 | 7/2004 | Zucherman et al. |
| 2004/0143332 A1 | 7/2004 | Krueger et al. |
| 2004/0172133 A1 | 9/2004 | Gerber |
| 2004/0176853 A1 | 9/2004 | Sennett et al. |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2006/0085071 A1 | 4/2006 | Lechmann et al. |
| 2006/0129240 A1 | 6/2006 | Lessar et al. |
| 2006/0142828 A1 | 6/2006 | Schorr |
| 2006/0217809 A1 | 9/2006 | Albert et al. |
| 2006/0241760 A1 | 10/2006 | Randall |
| 2007/0088441 A1 | 4/2007 | Duggal et al. |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0225806 A1 | 9/2007 | Squires et al. |
| 2007/0225812 A1 | 9/2007 | Gill |
| 2007/0233253 A1 | 10/2007 | Bray et al. |
| 2007/0250167 A1 | 10/2007 | Bray |
| 2007/0255414 A1 | 11/2007 | Melkent |
| 2007/0270961 A1 | 11/2007 | Ferguson |
| 2008/0046090 A1 | 2/2008 | Paul |
| 2008/0051890 A1 | 2/2008 | Waugh et al. |
| 2008/0051907 A1 | 2/2008 | Marik |
| 2008/0125865 A1 | 5/2008 | Abdelgany |
| 2008/0133013 A1 | 6/2008 | Duggal et al. |
| 2008/0154379 A1 | 6/2008 | Steiner |
| 2008/0188940 A1 | 8/2008 | Cohen |
| 2008/0249569 A1 | 10/2008 | Waugh |
| 2009/0012529 A1 | 1/2009 | Blain et al. |
| 2009/0024132 A1 | 1/2009 | Blain et al. |
| 2009/0076608 A1 | 3/2009 | Gordon et al. |
| 2009/0099661 A1 | 4/2009 | Bhattacharya |
| 2009/0101582 A1 | 4/2009 | Liu |
| 2009/0210062 A1 | 8/2009 | Thalgott et al. |
| 2010/0057206 A1 | 3/2010 | Duffield |
| 2010/0145459 A1 | 6/2010 | McDonough |
| 2010/0145460 A1 * | 6/2010 | McDonough ...... A61B 17/7059 623/17.16 |
| 2010/0305704 A1 | 12/2010 | Messerli |
| 2011/0087327 A1 | 4/2011 | Lechmann |
| 2011/0160864 A1 | 6/2011 | Messerli |
| 2011/0251689 A1 | 10/2011 | Seifert |
| 2012/0078373 A1 | 3/2012 | Gamache |
| 2012/0130495 A1 | 5/2012 | Duffield |
| 2012/0130496 A1 | 5/2012 | Duffield |
| 2012/0323330 A1 | 12/2012 | Kueenzi |
| 2013/0073047 A1 | 3/2013 | Laskowitz |
| 2013/0211523 A1 | 8/2013 | Southard |
| 2014/0214166 A1 * | 7/2014 | Theofilos .............. A61F 2/4611 623/17.16 |
| 2015/0005879 A1 | 1/2015 | Georges et al. |
| 2015/0025635 A1 | 1/2015 | Laubert |
| 2016/0058564 A1 | 3/2016 | Zappacosta et al. |
| 2016/0235448 A1 | 8/2016 | Seex |
| 2017/0042692 A1 | 2/2017 | Stewart et al. |
| 2018/0289496 A1 | 10/2018 | Zappacosta et al. |

FOREIGN PATENT DOCUMENTS

| | | |
|---|---|---|
| JP | 2017-529910 A | 10/2017 |
| WO | 1997023175 A1 | 7/1997 |
| WO | 1999063914 A1 | 12/1999 |
| WO | 2005007040 A1 | 1/2005 |
| WO | 2007098288 A2 | 8/2007 |
| WO | 2008014258 A2 | 1/2008 |
| WO | 2011019699 A2 | 2/2011 |

OTHER PUBLICATIONS

M. Spruit et al.,The in vitro stabilizing effect of polyetheretherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) Eur. Spine J. 1757, 1757-1765 (2008).

P.W. Pavlov et al.. Anterior lumbar interbody fusion with threaded fusion cages and autologous bone grafts, 9 Eur. Spine J. 224, 224-229 (2000).

Synthes' SynFix Technique Guide device ("SynFix Technique Guide"), copyright 2006, Synthes Spine.

* cited by examiner

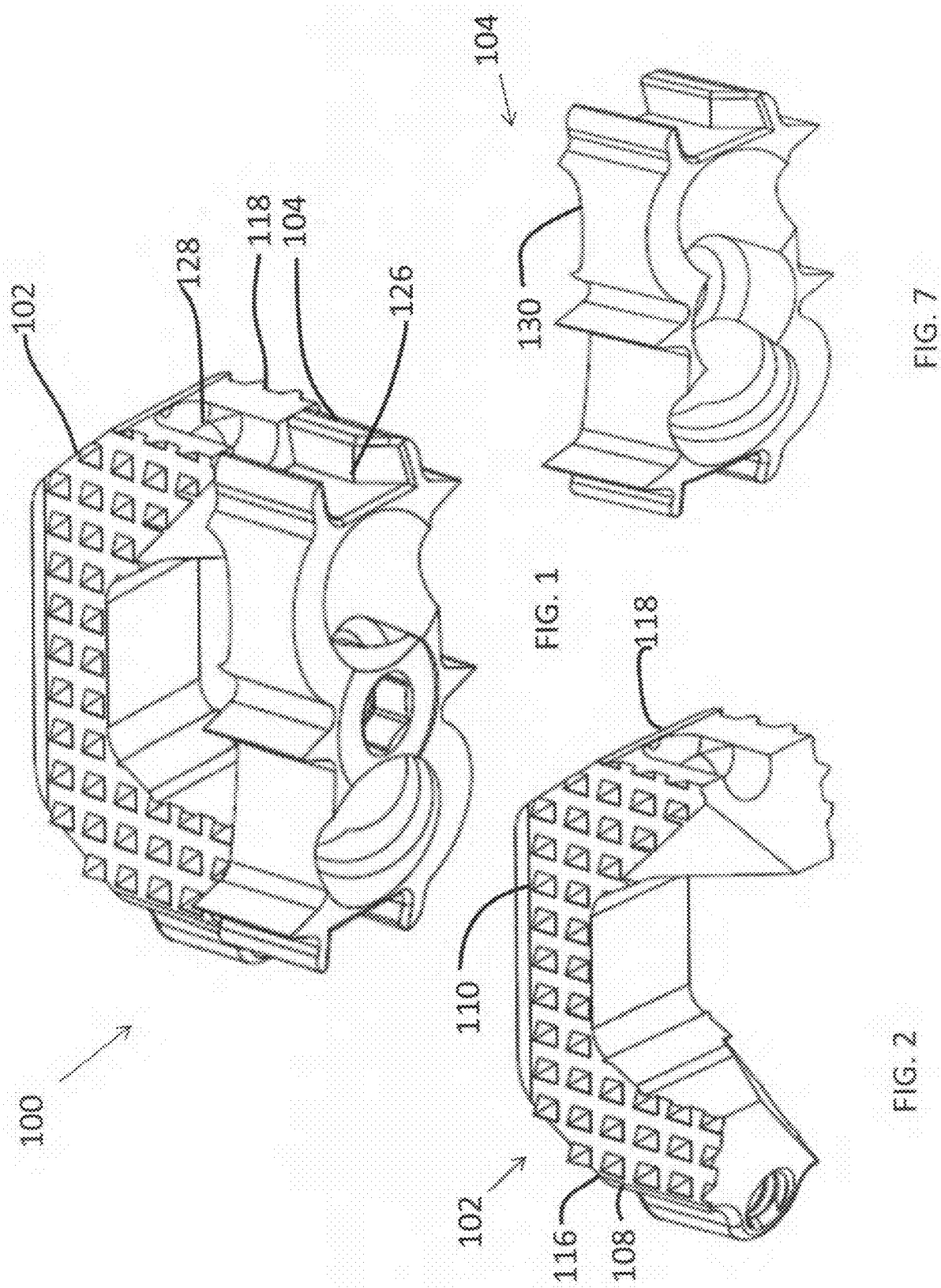

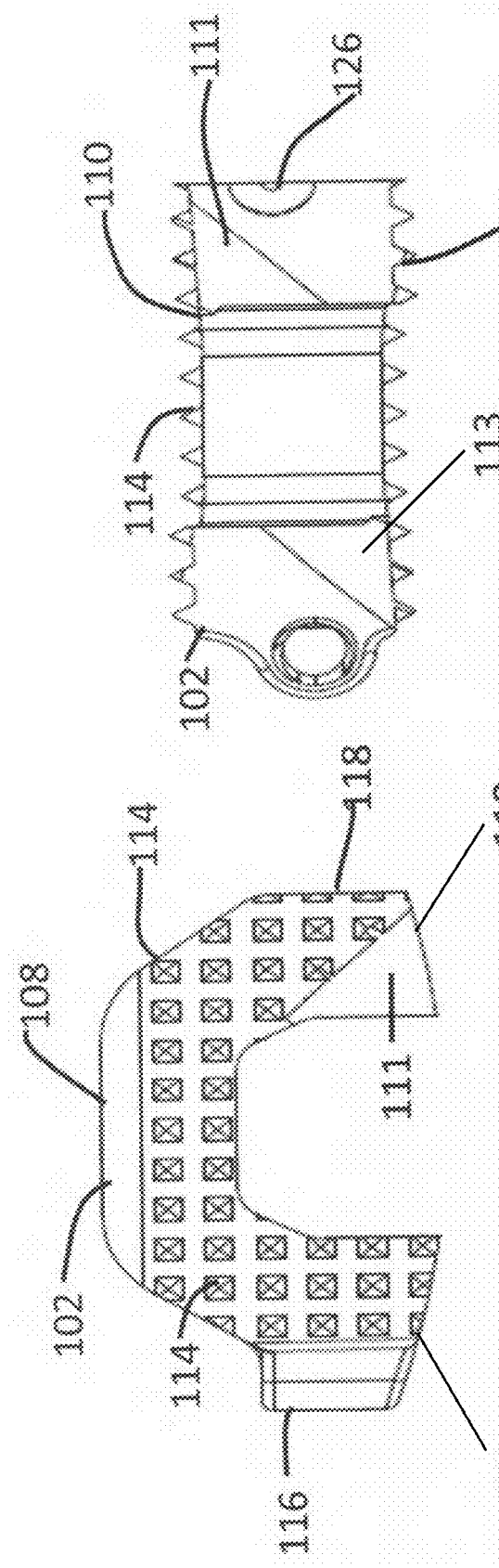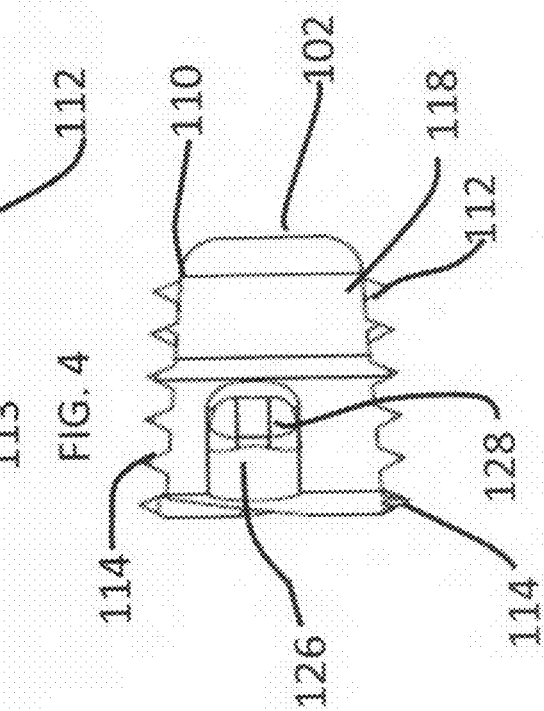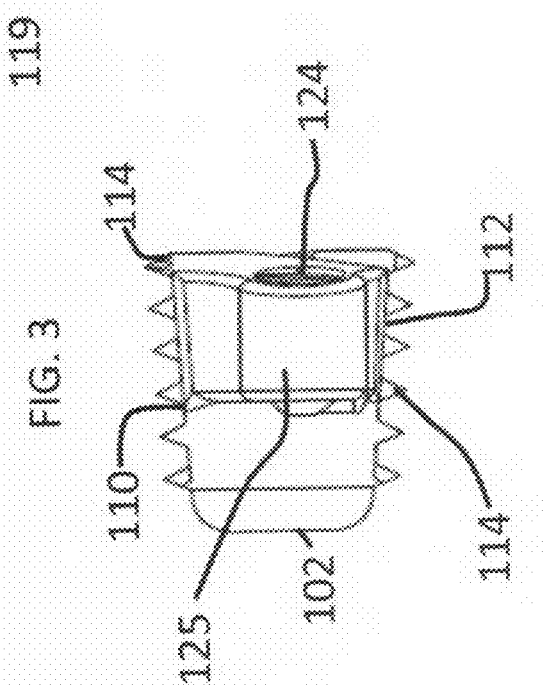

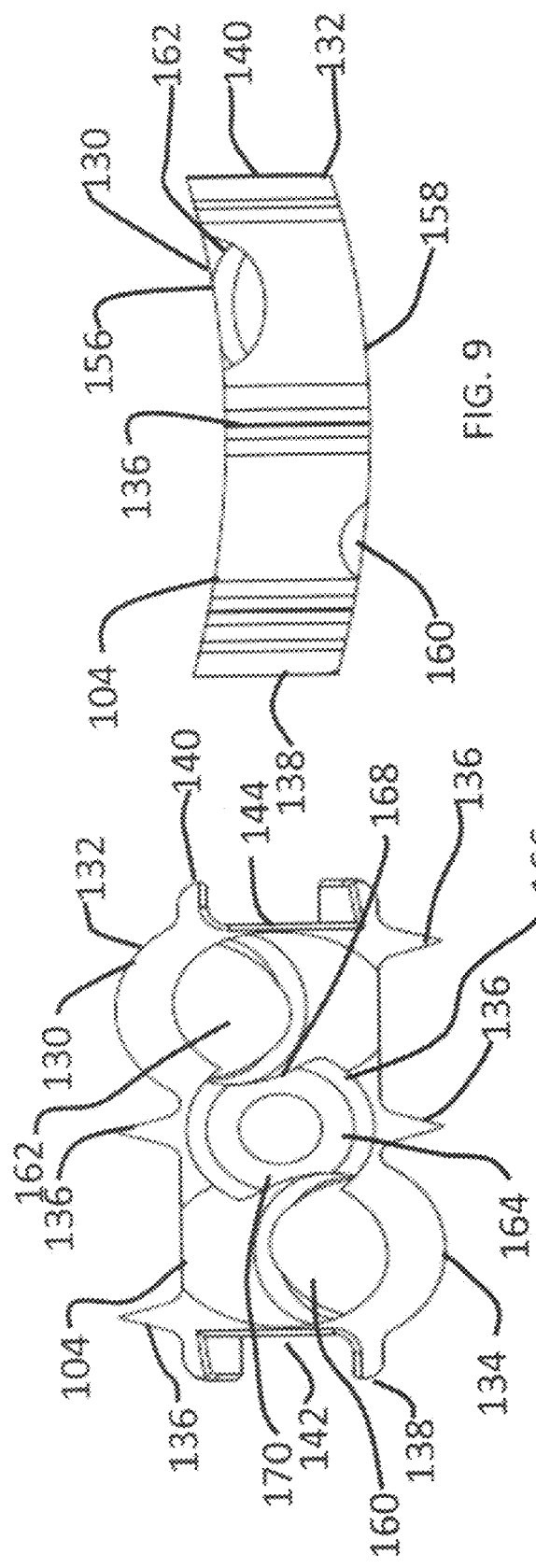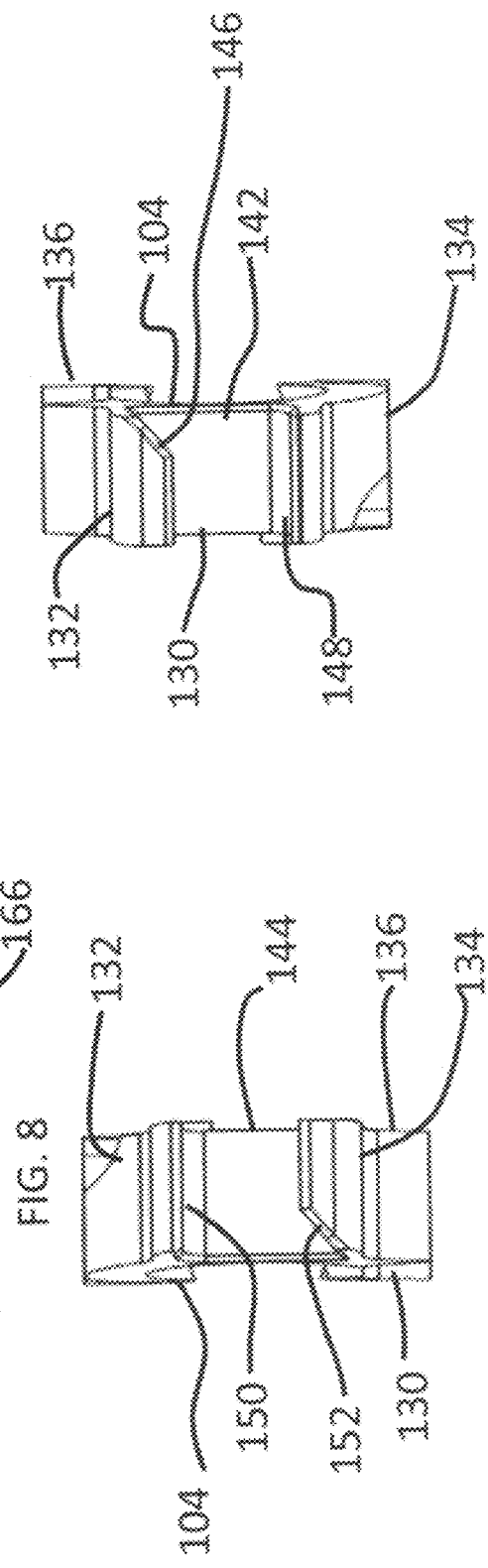

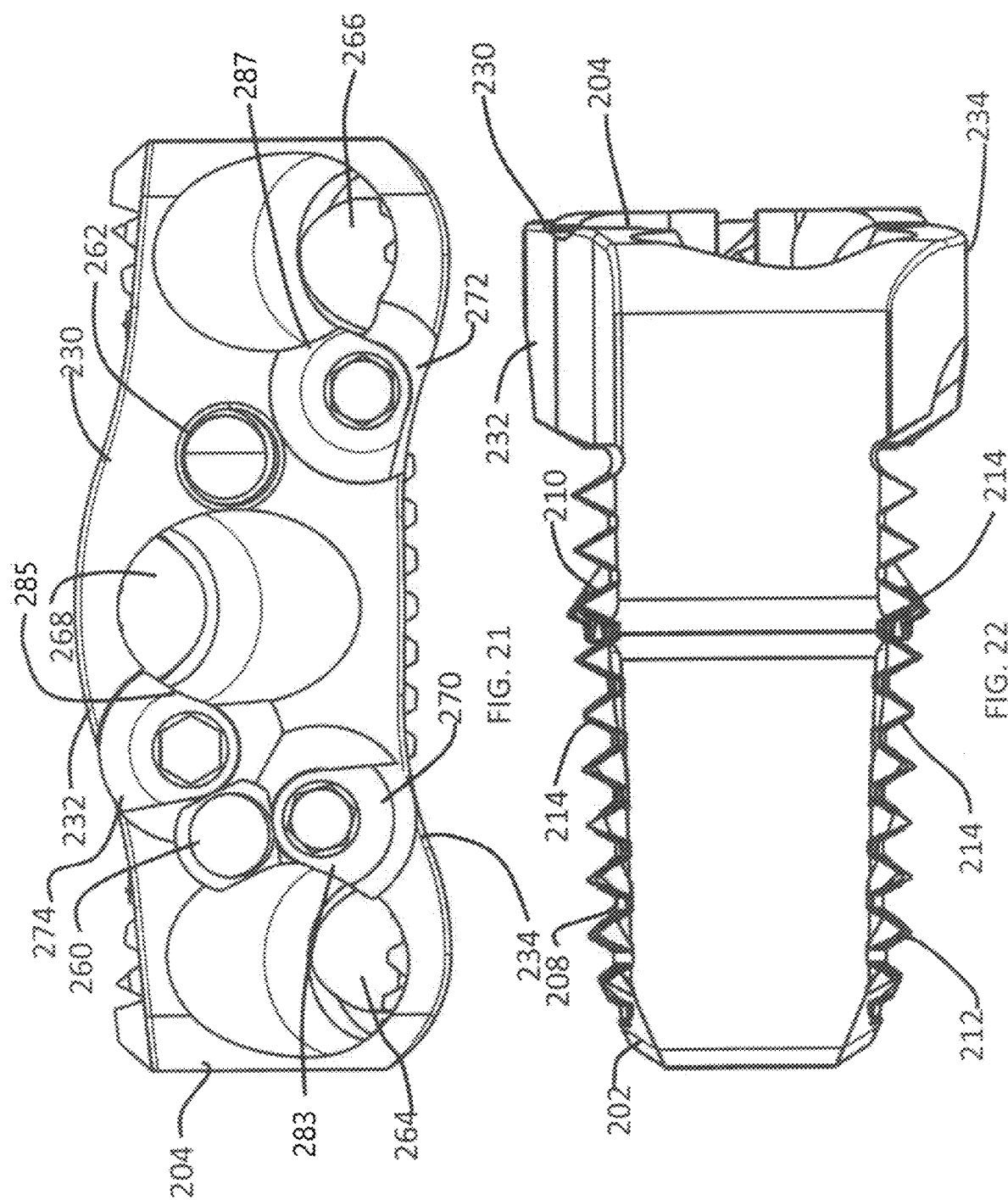

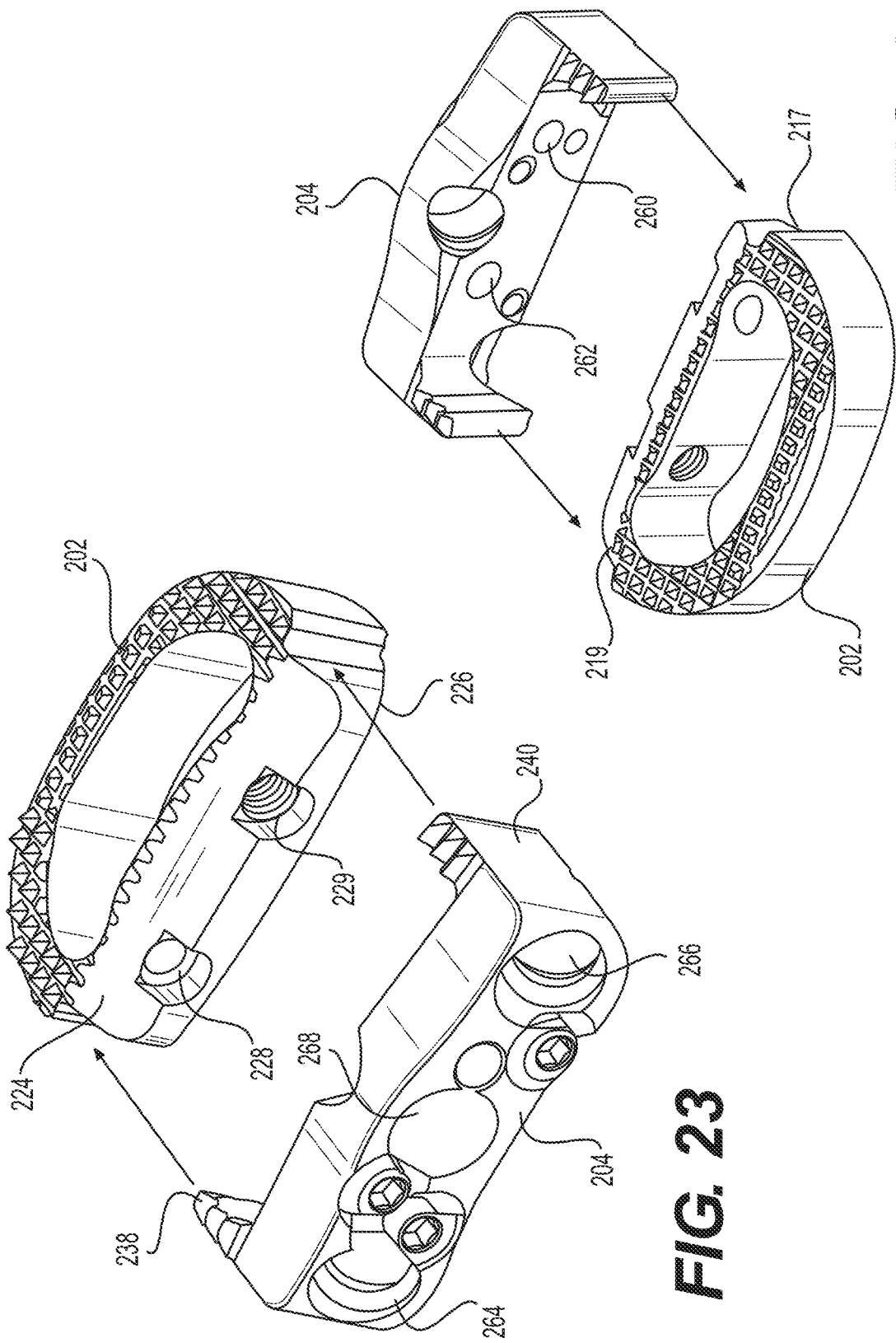

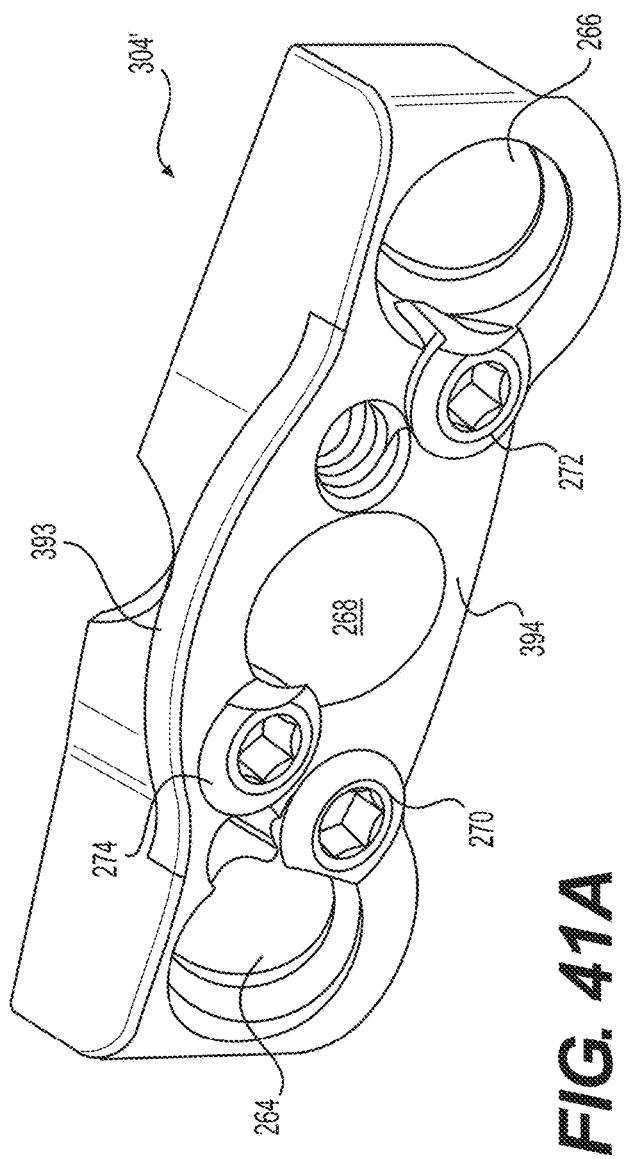
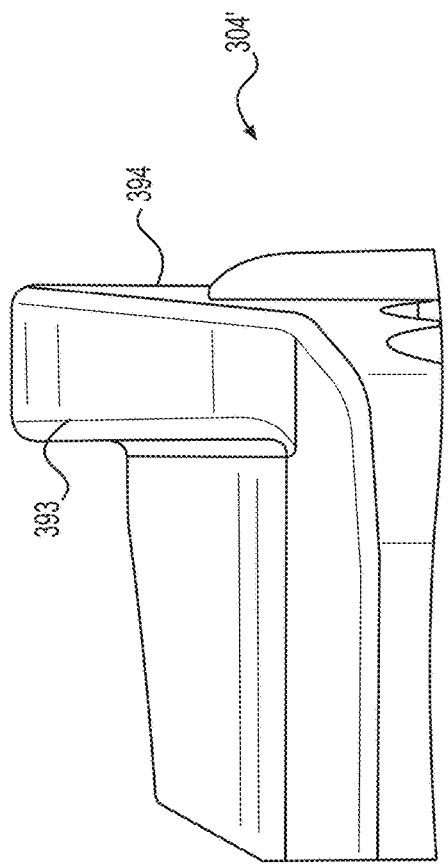
FIG. 41A
FIG. 41B

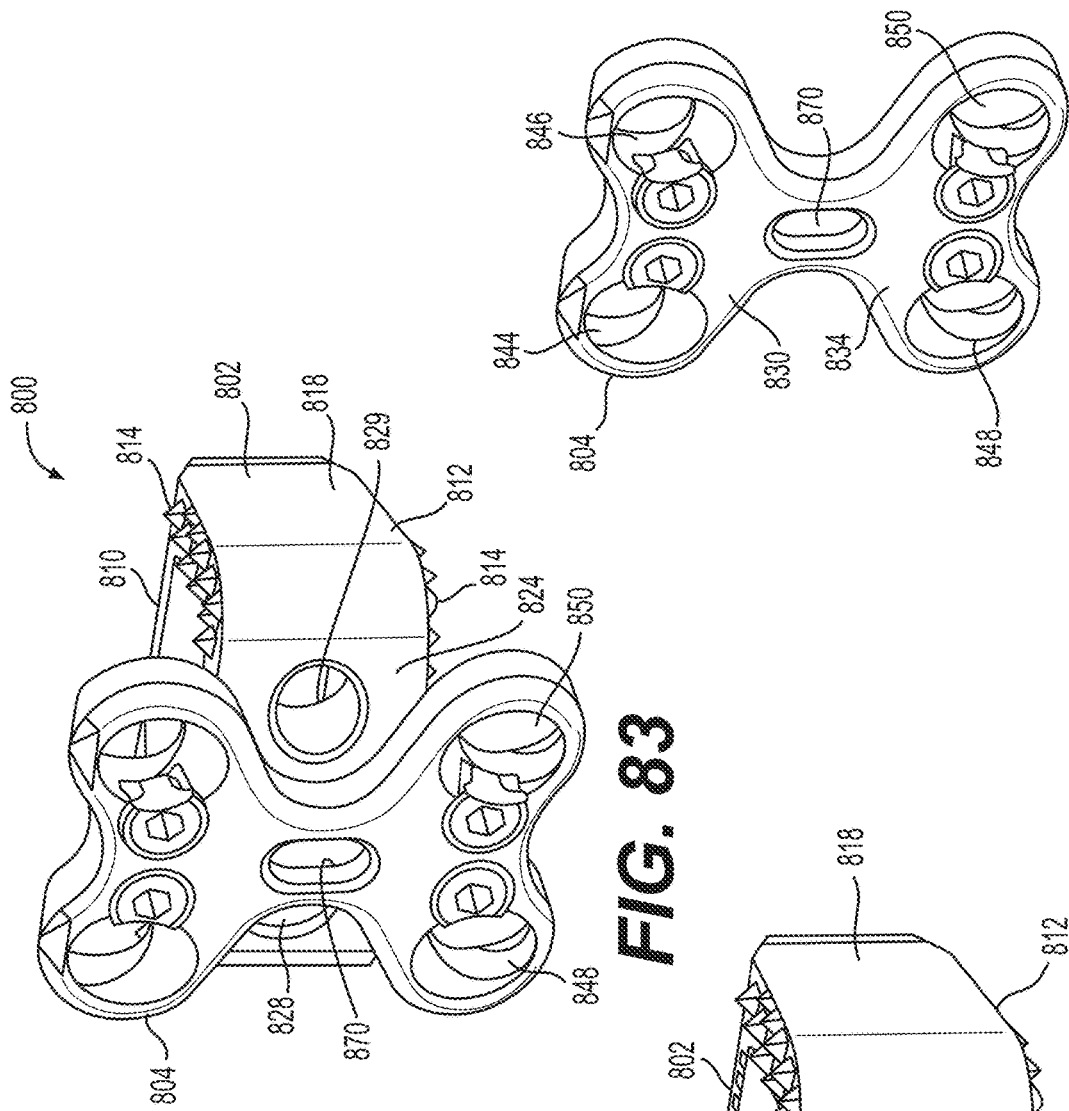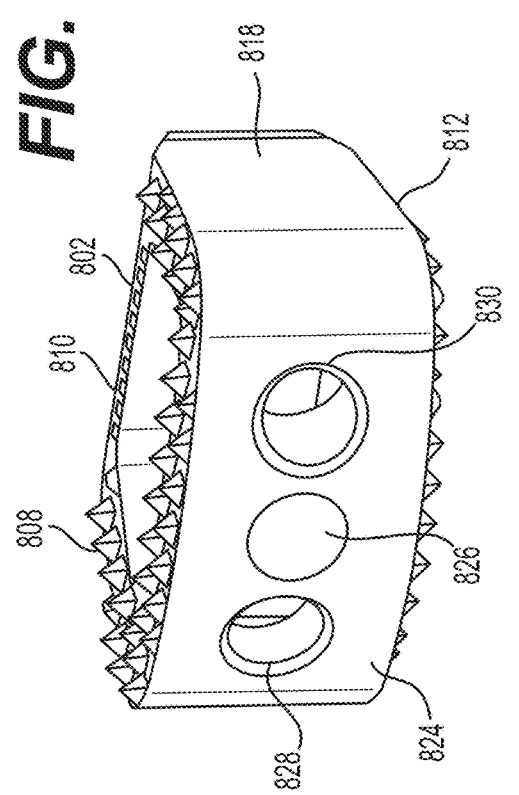

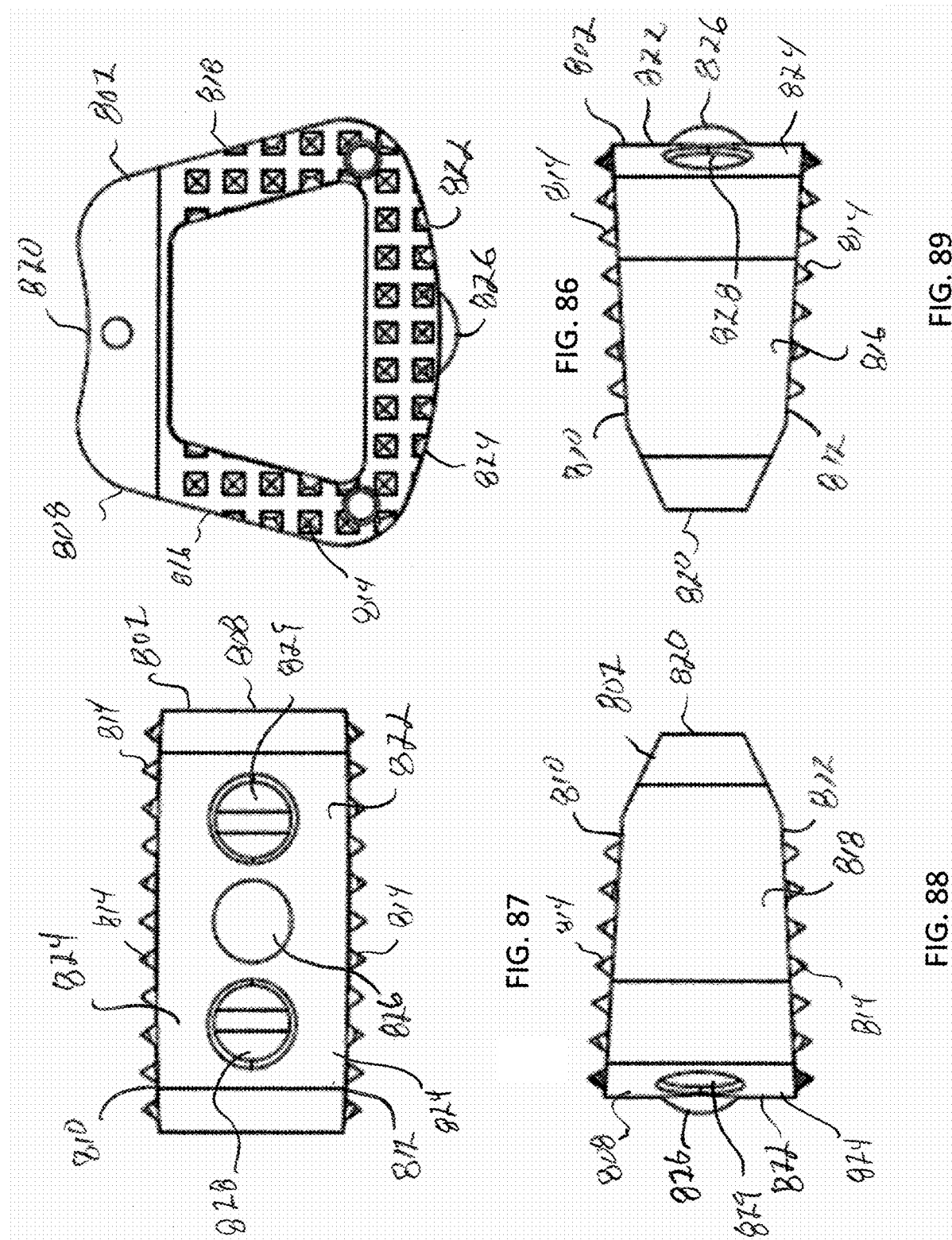

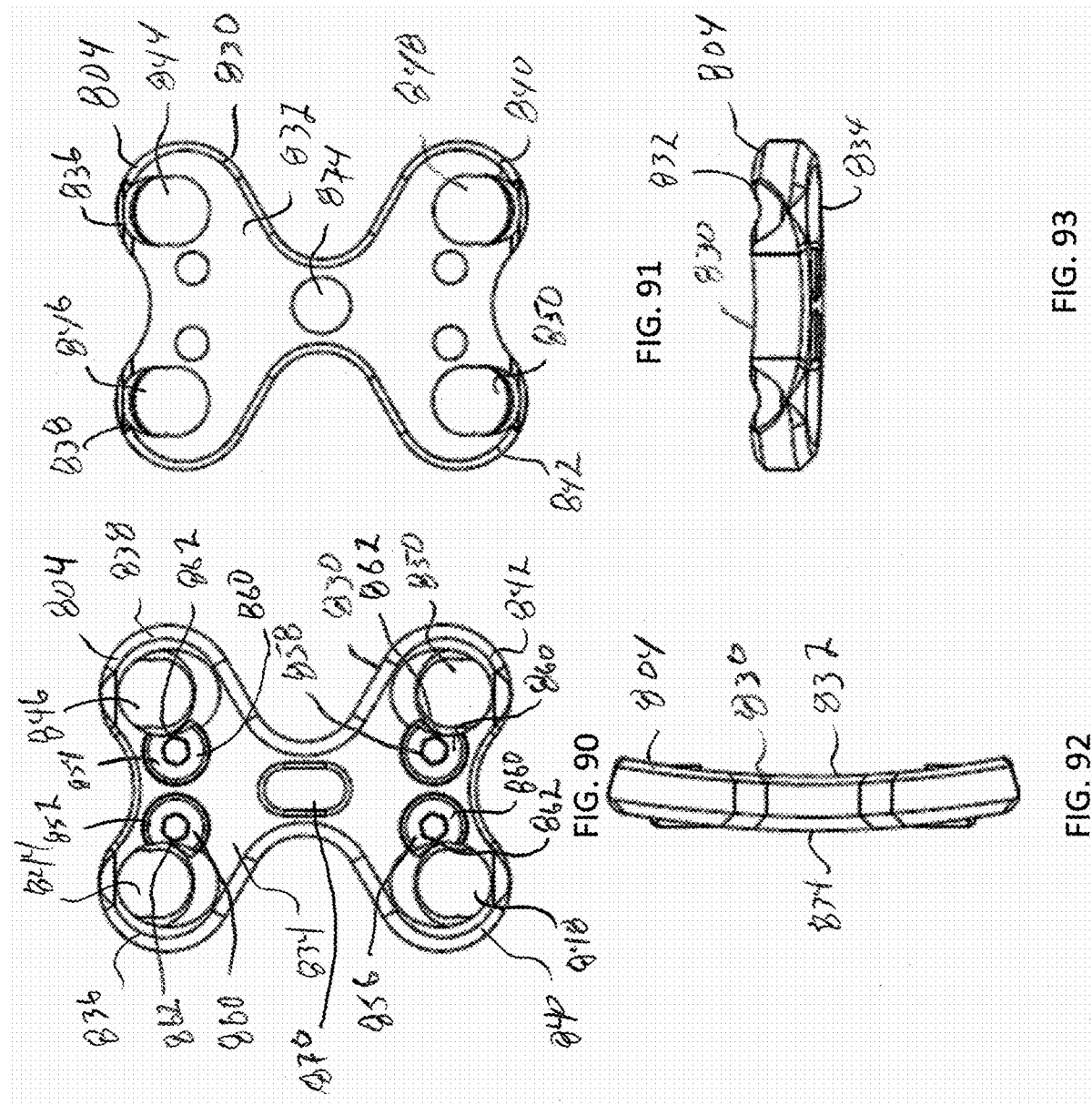

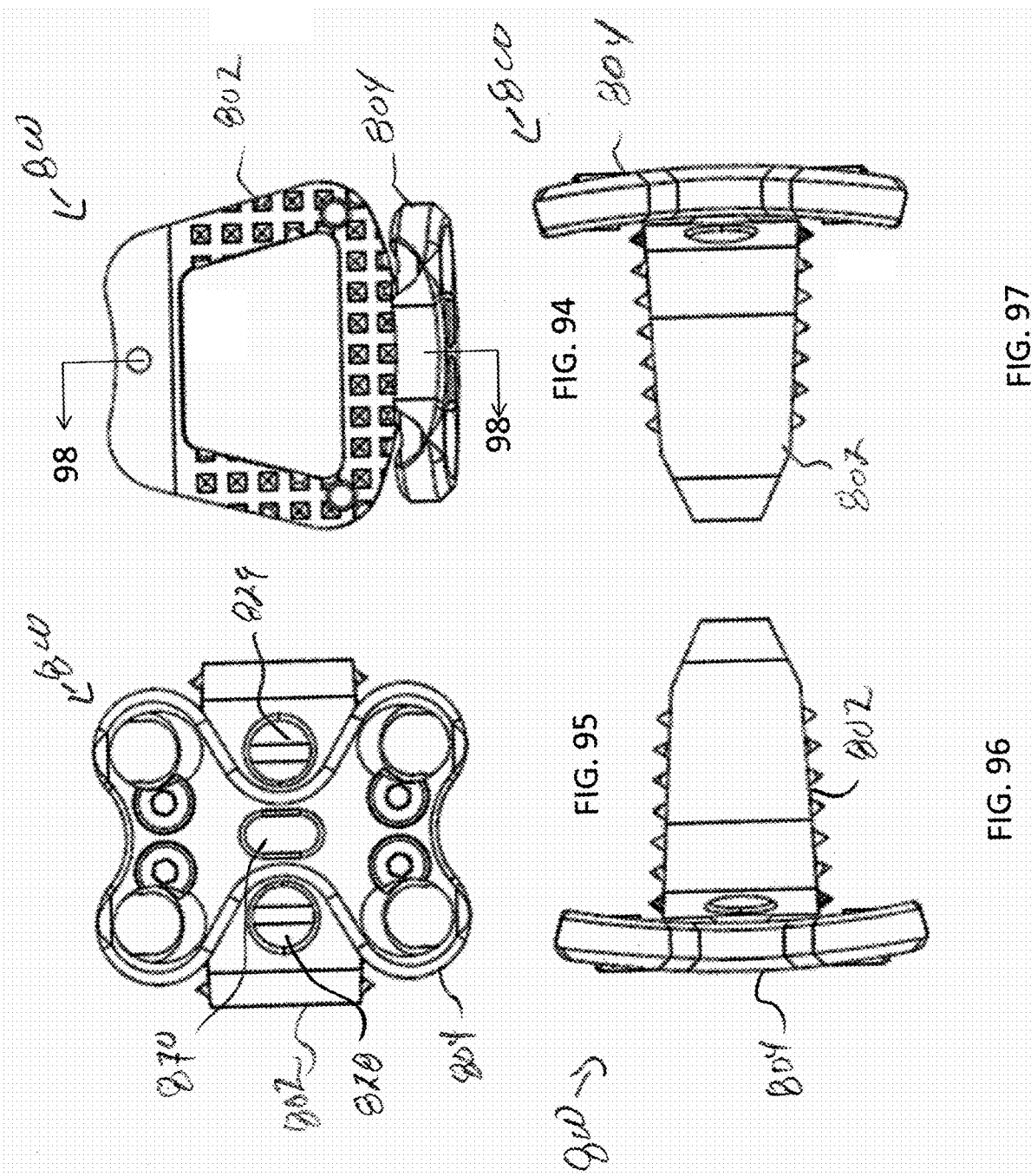

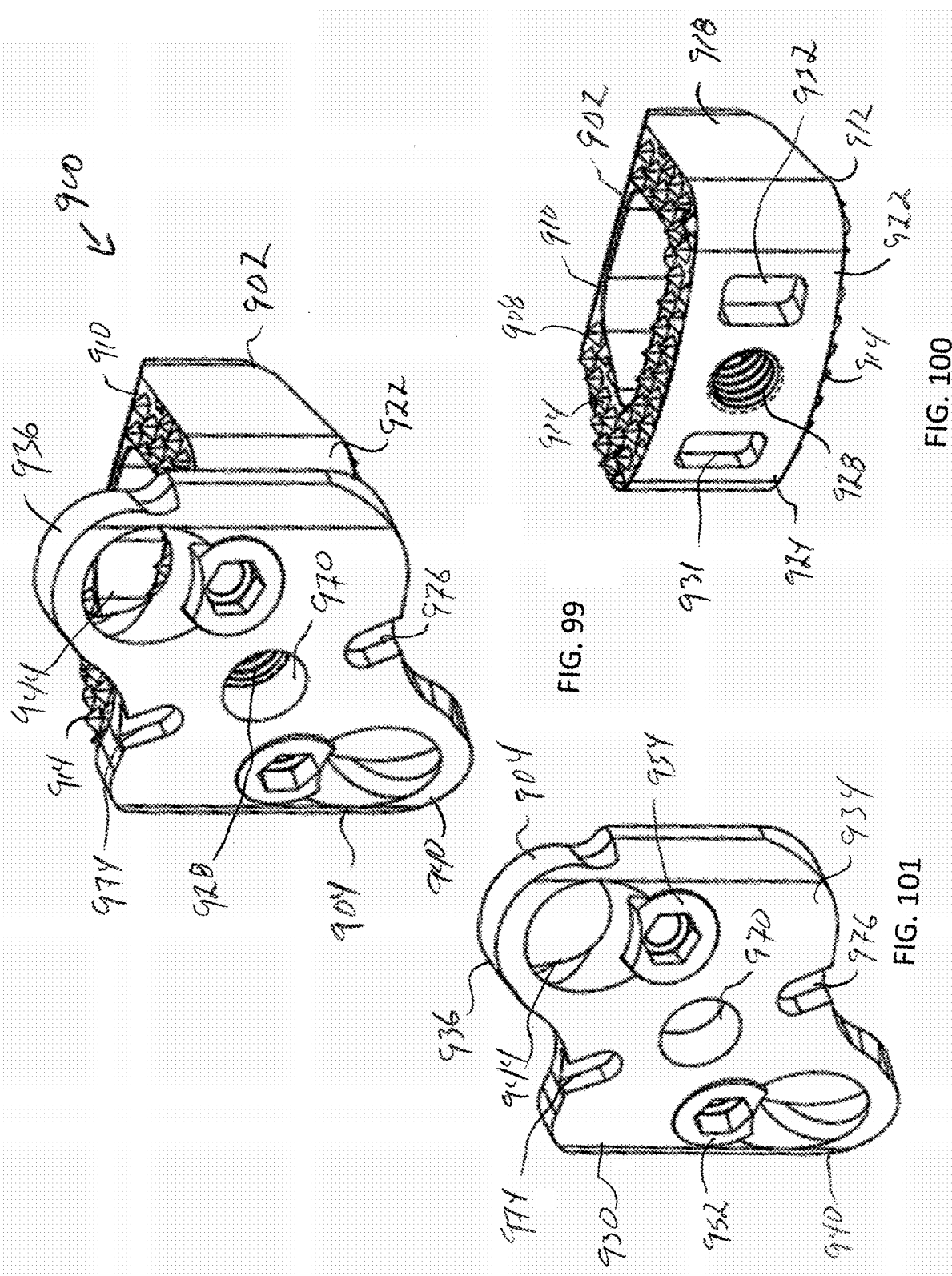

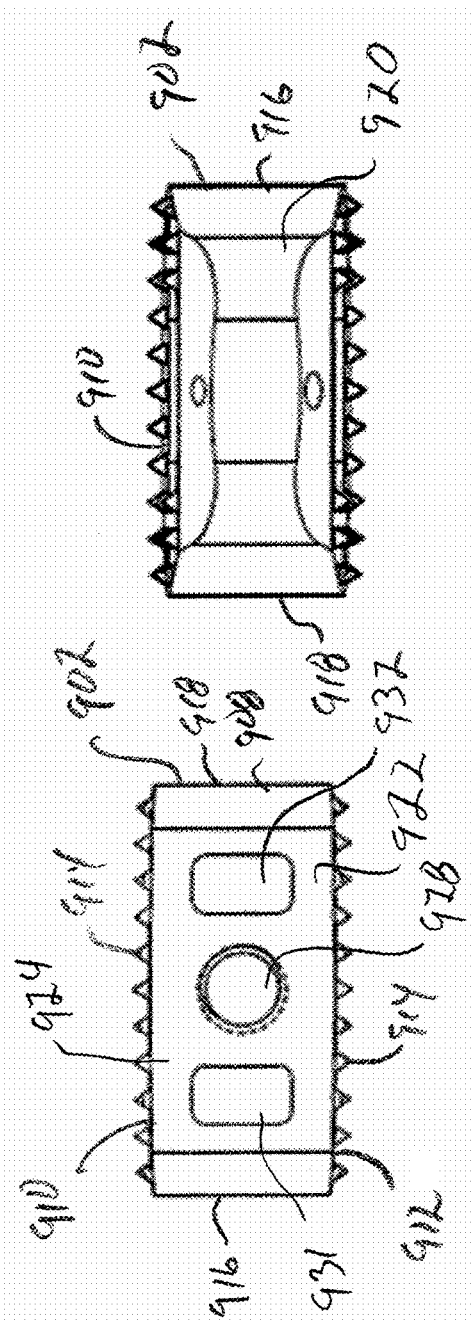
FIG. 104
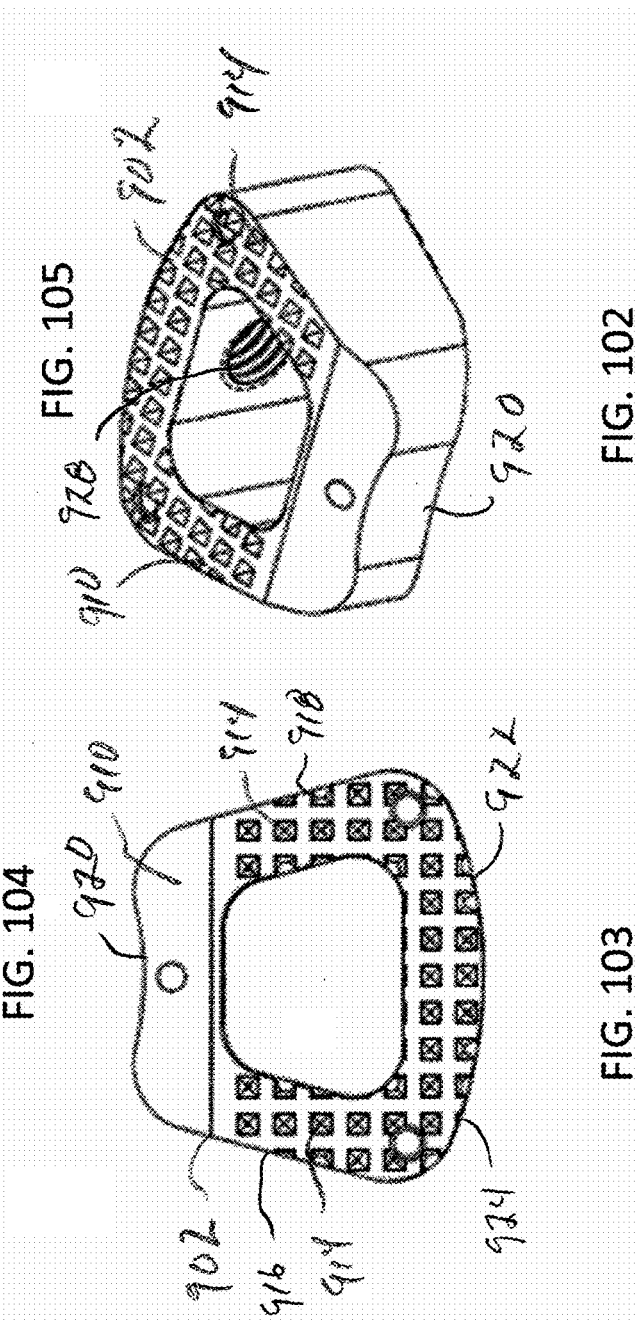
FIG. 105
FIG. 102
FIG. 103

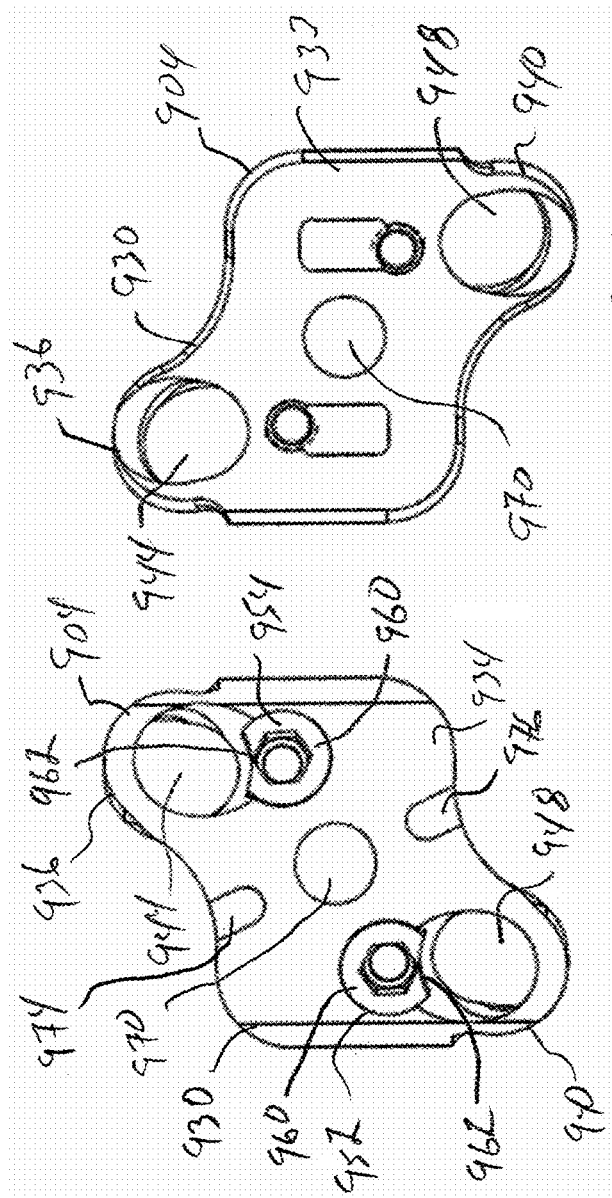
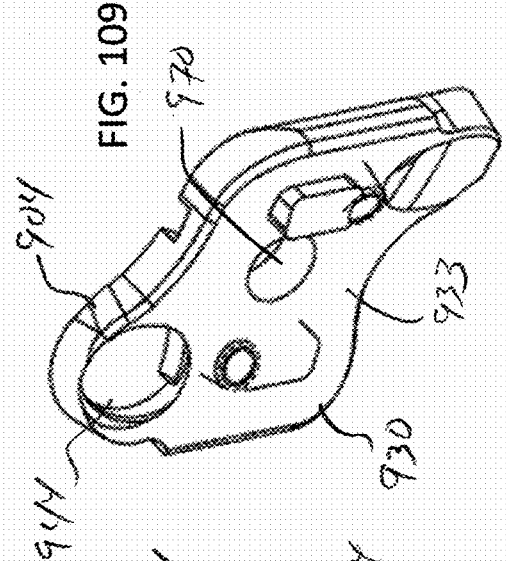
FIG. 106
FIG. 107
FIG. 108
FIG. 109

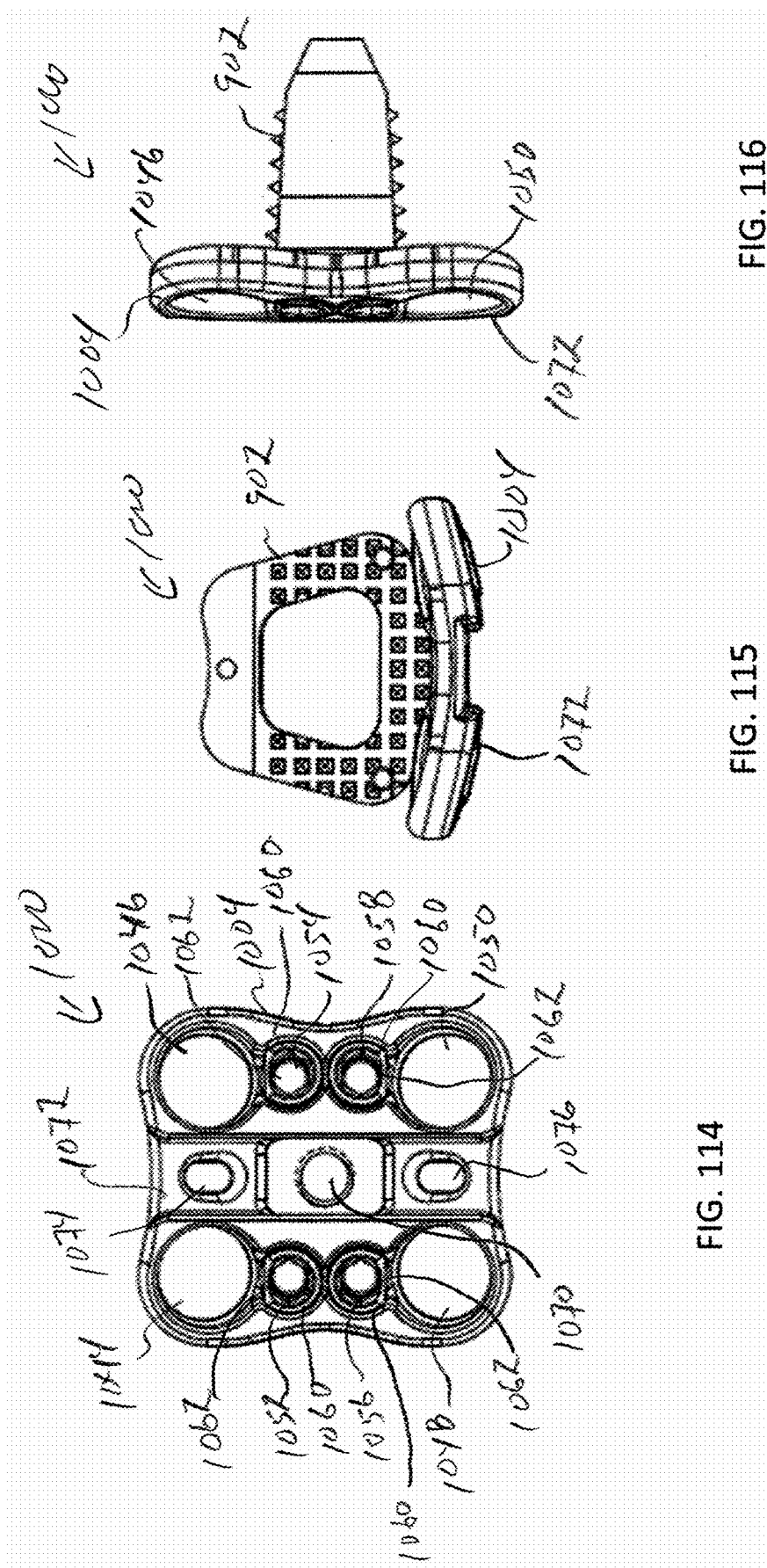

DECOUPLED SPACER AND PLATE AND METHOD OF INSTALLING THE SAME

REFERENCE TO RELATED APPLICATIONS

The present application is a continuation application of U.S. Ser. No. 15/479,438, filed Apr. 5, 2017 (published as U.S. Pat. Pub. No. 2018-0289495), which is hereby incorporated by reference in its entirety.

BACKGROUND

Field of the Invention

The present invention relates to bone fixation, and more specifically, to a method of installing an intervertebral spacer and plate.

Description of the Related Art

Various types of spacers can be used in spinal fusion procedures. A standalone spacer is one in which a spacer is attached to a plate. The plate is configured to receive one or more screws that secure the standalone spacer to one or more adjacent vertebrae. The combined spacer/plate structure is typically rigid, thereby reducing the flexibility of the patient at the implant site.

There exists a need for intervertebral spacer and plate assemblies that are inserted as a unit with an insertion tool, but are decoupled from each other when the insertion tool is removed. Further, methods of inserting the assemblies are also needed.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a method of installing an intervertebral spacer and plate assembly may include coupling an intervertebral spacer and plate to an insertion tool; delivering the coupled spacer and plate to a surgical site via the insertion tool, wherein the spacer and/or plate are received in an intervertebral disc space; inserting one or more bone screws into the plate to secure the plate to one or more adjacent vertebrae; and removing the insertion tool, such that the spacer is decoupled from the plate at the surgical site.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 1 is a perspective view of a spacer and plate assembly according to a first exemplary embodiment;

FIG. 2 is a perspective view of the spacer shown in FIG. 1;

FIG. 3 is a top plan view of the spacer shown in FIG. 2;

FIG. 4 is a posterior elevational view of the spacer shown in FIG. 2;

FIG. 5 is a left lateral side elevational view of the spacer shown in FIG. 2;

FIG. 6 is a right lateral side elevational view of the spacer shown in FIG. 2;

FIG. 7 is a perspective view of the plate shown in FIG. 1;

FIG. 8 is a posterior elevational view of the plate shown in FIG. 7;

FIG. 9 is a top plan view of the plate shown in FIG. 7;

FIG. 10 is a left lateral side elevational view of the plate shown in FIG. 7;

FIG. 11 is a right lateral side elevational view of the plate shown in FIG. 7;

FIG. 21 is a posterior elevational view of the assembly shown in FIG. 20;

FIG. 22 is a left lateral side elevational view of the assembly shown in FIG. 20;

FIG. 23 is an exploded posterior perspective view of the assembly shown in FIG. 20;

FIG. 24 is an exploded anterior perspective view of the assembly shown in FIG. 20;

FIG. 41A is an anterior perspective view of an alternative plate for use with the spacer shown in FIG. 20;

FIG. 41B is a left perspective view of the plate shown in FIG. 41A;

FIG. 83 is a perspective view of a spacer and plate assembly according to an eighth exemplary embodiment;

FIG. 84 is a perspective view of a spacer used with the assembly shown in FIG. 83;

FIG. 85 is a perspective view of a plate used with the assembly shown in FIG. 83;

FIG. 86 is a top plan view of the spacer shown in FIG. 84;

FIG. 87 is an anterior elevational view of the spacer shown in FIG. 84;

FIG. 88 is a right side elevational view of the spacer shown in FIG. 84;

FIG. 89 is a left side elevational view of the spacer shown in FIG. 84;

FIG. 90 is an anterior elevational view of the plate shown in FIG. 85;

FIG. 91 is a posterior elevational view of the plate shown in FIG. 85;

FIG. 92 is a right side elevational view of the plate shown in FIG. 85;

FIG. 93 is a top plan view of the spacer shown in FIG. 85;

FIG. 94 is a top plan view of the assembly shown in FIG. 83;

FIG. 95 is an anterior elevational view of the assembly shown in FIG. 83;

FIG. 96 is a right side elevational view of the assembly shown in FIG. 83;

FIG. 97 is a left side elevational view of the assembly shown in FIG. 83;

FIG. 99 is a perspective view of a spacer and plate assembly according to a ninth exemplary embodiment;

FIG. 100 is a perspective view of a spacer used with the assembly shown in FIG. 99;

FIG. 101 is a perspective view of a plate used with the assembly shown in FIG. 99;

FIG. 102 is a perspective view of the spacer shown in FIG. 100;

FIG. 103 is top plan view of the spacer shown in FIG. 100;

FIG. 104 is an anterior elevational view of the spacer shown in FIG. 100;

FIG. 105 is a posterior elevational view of the spacer shown in FIG. 100;

FIG. 106 is top plan view of the plate shown in FIG. 101;

FIG. 107 is a perspective view of the plate shown in FIG. 101;

FIG. 108 is an anterior elevational view of the plate shown in FIG. 101;

FIG. 109 is a posterior elevational view of the spacer shown in FIG. 101;

FIG. 114 is an anterior elevational view of a spacer and plate assembly according to a tenth exemplary embodiment;

FIG. 115 is a top plan view of the assembly shown in FIG. 114;

FIG. 116 is a right side elevational view of the assembly shown in FIG. 114;

FIG. 117 is a top plan view of a spacer and plate assembly according to an eleventh exemplary embodiment;

FIG. 118 is a top plan view of a spacer and plate assembly according to a twelfth exemplary embodiment;

FIG. 119 is a top plan view of a spacer and plate assembly according to a thirteenth exemplary embodiment;

FIG. 120 is a top plan view of a spacer and plate assembly according to a fourteenth exemplary embodiment;

FIG. 121 is a top plan view of a spacer and plate assembly according to a fifteenth exemplary embodiment;

FIG. 122 is a top plan view of a spacer and plate assembly according to a sixteenth exemplary embodiment;

FIG. 123 is posterior side elevation view of a spacer according to a seventeenth exemplary embodiment;

FIG. 124 is an anterior side elevation view of the spacer shown in FIG. 123;

FIG. 125 is a top plan view of the spacer shown in FIG. 123, with a plate and insertion device;

FIG. 126 is a top plan view of a spacer and plate assembly according to an eighteenth exemplary embodiment;

Figure 127:
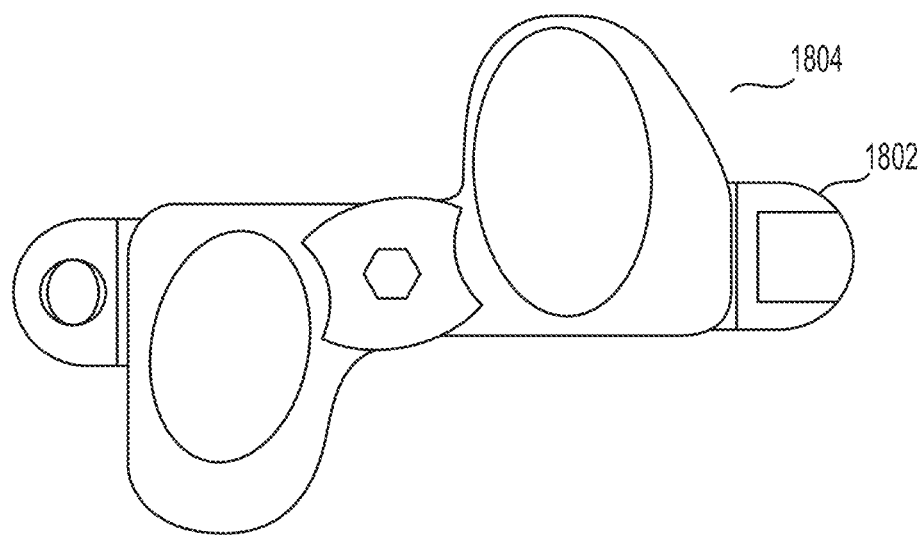
Figure 126:
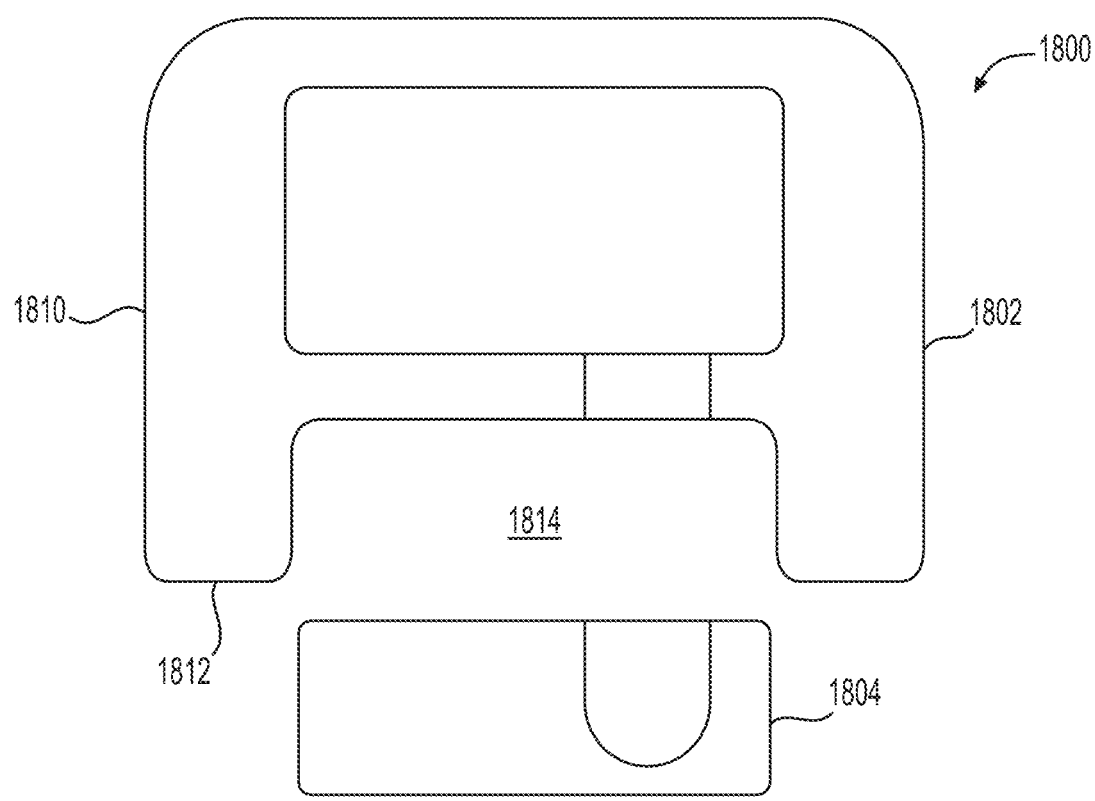
Figure 128:
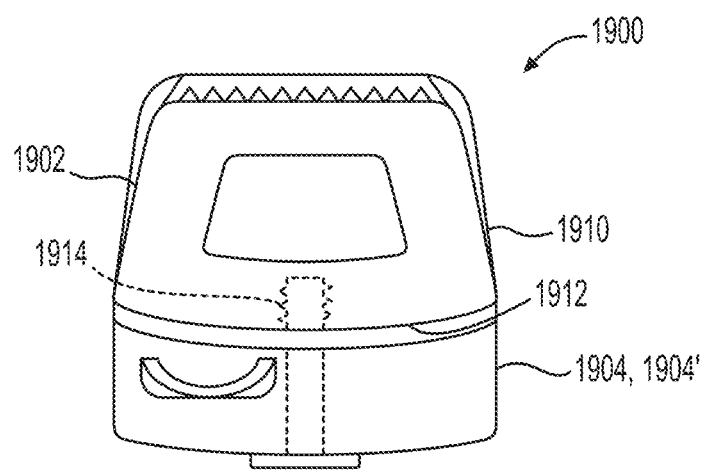
Figure 129:
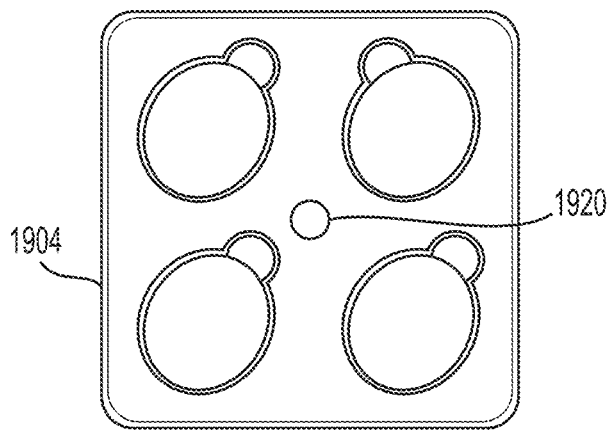

FIG. 127 is a posterior side elevation view of the assembly shown in FIG. 126;

FIG. 128 is a top plan view of a spacer and plate assembly according to a nineteenth exemplary embodiment;

FIG. 129 is a posterior side elevation view of the plate shown in FIG. 128; and

Figure 130:
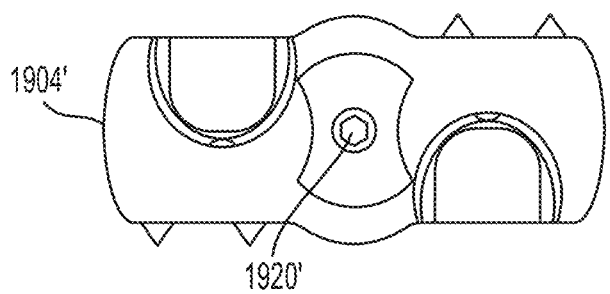

FIG. 130 is a posterior side elevation view of the spacer shown in FIG. 128.

DETAILED DESCRIPTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

In performing spinal fusion procedures, a spacer can be inserted into a disc space. In some embodiments, a stand-alone spacer can be attached to a plate. The plate can receive one or more bone anchors or screws to attach to the plate to one or more adjacent vertebrae. The plate and spacer are often rigidly connected and are not decoupled from one another.

The present application includes spacer and plate assemblies that can be coupled via an insertion instrument upon delivery to a surgical site. In some embodiments, a surgical site can be at or near a disc space, as one skilled in the art will appreciate. The insertion instrument advantageously provides a single tool for delivering both the spacer and plate if desired. Once the spacer and plate are implanted at the surgical site, the insertion instrument can be removed. With the insertion instrument removed, the spacer and plate are considered decoupled from one another. By providing a spacer and plate that are independent and decoupled from one another, a surgeon advantageously has the option to implant both a plate and a spacer, a spacer by itself, or a plate by itself if desired.

The present disclosure provides embodiments of intervertebral spacers and plates that can be used to space and fixedly secure two adjacent vertebrae. According to one embodiment, shown in FIGS. 1-19, an intervertebral spacer and plate assembly 100 ("assembly 100") is provided. In an exemplary embodiment, assembly 100 can be used for cervical repair, although those skilled in the art will recognize that assembly 100 can be sized for thoracic or lumbar repair as well.

Assembly 100 is formed from two separate components, an intervertebral spacer 102 and a plate 104. In some embodiments, spacer 102 and plate 104 are not directly connected to each other, but are instead each separately coupled to an insertion tool 106, shown in FIGS. 16-19.

Referring to FIGS. 1-6, spacer 102 includes a body 108 having a superior surface 110 and an opposing inferior surface 112. Each of superior surface 110 and inferior surface 112 can have a plurality of protrusions or fixation elements 114 extending outwardly therefrom. While fixation elements 114 are shown as being generally pyramidal in shape, those skilled in the art will recognize that fixation elements 114 can be other shapes, such as ribbed, or other suitable shapes. Fixation elements 114 are used to bite into a grip each of adjacent vertebrae (not shown) between which spacer 102 is inserted.

As shown in FIG. 2, body 102 can have a generally U-shape, with generally parallel lateral sides 116, 118, connected to each other by an anterior portion 120. Lateral side 116 includes a convex arcuate posterior face 117 while lateral side 118 includes a convex arcuate posterior face 119. The space between lateral sides 116, 118 can optionally be filled with graft material. The advantage of a U-shaped body is that if a surgeon decides to use the spacer 102 on its own, it can be easily backfilled through the opening of the "U". Referring to FIGS. 2-4, superior surface 110 along lateral side 118 includes a cutout 111 that slopes inferiorly in an anterior-to posterior direction. Similarly, inferior surface 112 along lateral side 116 includes a cutout 113 that slopes superiorly in an anterior-to posterior direction. Cutouts 111, 113 allow for securing screws (not shown) to be inserted through plate 104, along cutouts 111, 113, respectively, and into adjacent vertebrae (not shown) without engaging spacer 102.

Lateral side 116 includes a tubular protrusion 122 extending in an anterior-posterior direction. Protrusion 122 has an internally threaded passage 124 that is sized to accept a portion of insertion tool 106 as will be explained in detail below. Passage 124 can have a closed anterior end 125.

Lateral side 118 includes an open slot 126 that extends in an anterior-posterior direction. An anterior end 128 of slot 126 extends medially inward and is sized to accept a portion of insertion tool 106 as will be explained in detail below.

Referring now to FIGS. 1 and 7-11, plate 104 includes a body 130 having a superior surface 132 and an opposing inferior surface 134. In some embodiments, the plate 104 is sized and configured to be received within a disc space, while in other embodiments, at least a portion of the plate 104 is sized and configured to be received outside of a disc space. Each of superior surface 132 and inferior surface 134 can have a plurality of stabilizer elements 136 extending outwardly therefrom. In some embodiments, the stabilizer elements 136 can be for torsional stabilization. In an exemplary embodiment, one stabilizer element 136 is located along a central anterior-to-posterior axis, and a second stabilizer element 136 is located proximate to a lateral side of body 130. While stabilizer elements 136 are shown as being generally ribbed in shape, those skilled in the art will recognize that stabilizer elements 136 can be other shapes, such as pyramidal, or other suitable shapes. Stabilizer elements 136 are used to bite into a grip each of adjacent vertebrae (not shown) between which spacer 102 is inserted.

Figure 13:
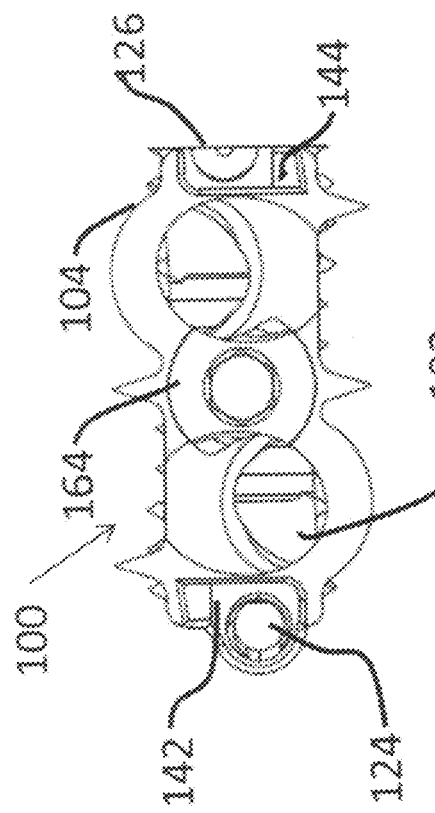
FIG. 13 is a posterior elevational view of the assembly shown in FIG. 1.
Figure 14:
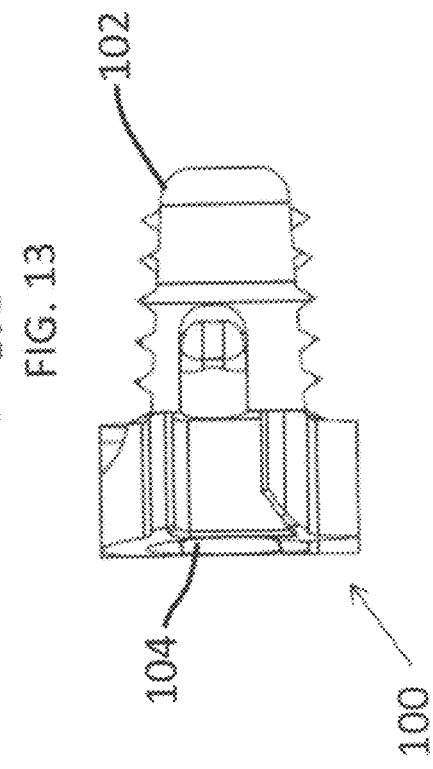
FIG. 14 is a right lateral side elevational view of the assembly shown in FIG. 1.

As shown in FIG. 9, body 130 can have a generally arcuate shape, with generally parallel lateral sides 138, 140. Each lateral side 138, 140 includes an anterior-to-posterior slot 142, 144, respectively. Slot 142 includes a superior surface 146 and a generally parallel inferior surface 148, while slot 144 includes a superior surface 150 and a generally parallel inferior surface 152. As shown in FIG. 13, when plate 104 is aligned with spacer 102 for insertion, slot 142 is aligned with threaded passage 124 and slot 144 is aligned with open slot 126.

Figure 12:
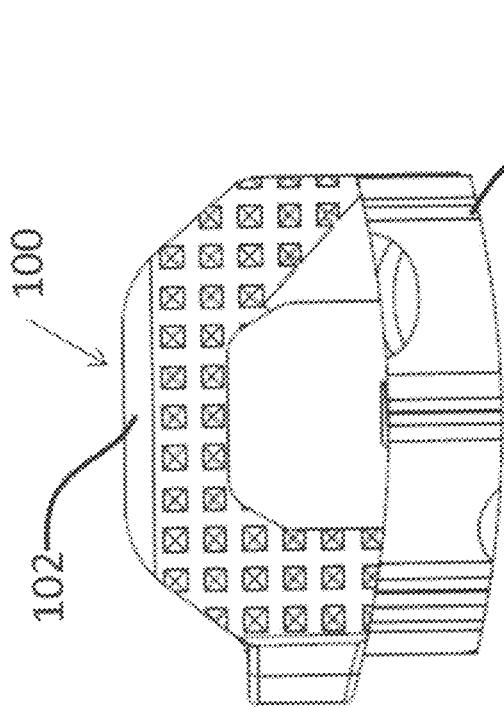
FIG. 12 is a top plan view of the assembly shown in FIG. 1.
Figure 15:
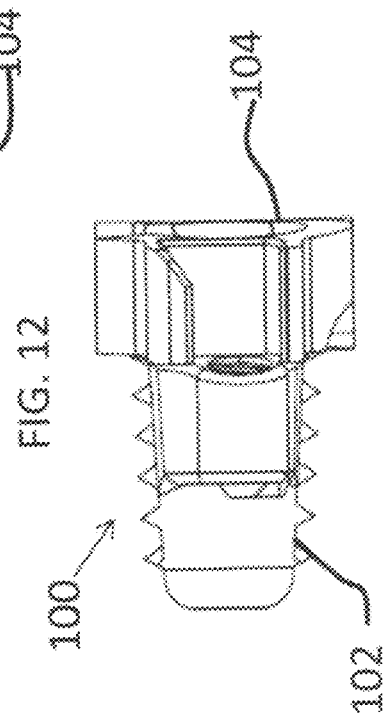
FIG. 15 is a left lateral side elevational view of the spacer shown in FIG. 1.

Body 130 includes a generally concave arcuate anterior face 156 that mates with convex arcuate faces 117, 119 of spacer 102 when plate 104 is located against spacer 102, as shown in FIG. 12. Body 130 also includes a generally convex posterior face 158 that extends generally parallel to anterior face 156.

Through-holes 160, 162 extend through body 130 in a posterior-to-anterior direction. Through-holes 160, 162 are sized to allow a bone or securing screw (not shown) to be inserted therethrough to secure plate 104 to each of a superior vertebra (not shown) and an inferior vertebra (not shown), between which spacer 102 is being inserted. Through-hole 160 extends in a superior-to-inferior direction so that its screw engages and secures to the inferior vertebra, while through-hole 162 extends in an inferior-to-superior direction so that its screw engages and secures the superior vertebra.

A locking screw 164 is disposed between through-holes 160, 162. Locking screw 164 has a head 166 with diametrically opposed arcuate cutouts 168, 170 that are sized to allow the securing screws discussed above to be inserted into through-holes 160, 162. During insertion of assembly 100, locking screw 164 is in a configuration relative to plate 104 as shown in FIG. 8. After the securing screws secure plate 104 to the superior and inferior vertebra, locking screw 164 is rotated, for example, about 90 degrees, so that head 166 extends over the securing screws, preventing the securing screws from inadvertently backing out.

FIGS. 1 and 12-15 show assembly 100. While plate 104 abuts spacer 102, plate 104 is not rigidly connected to spacer 102 in any way so that spacer 102 and plate 104 remain separate, independent components. During insertion via an insertion tool, the spacer 102 and plate 104 can both be coupled to the insertion tool. After insertion to a surgical site, the spacer 102 and plate 104 are decoupled from one another.

Figure 16:
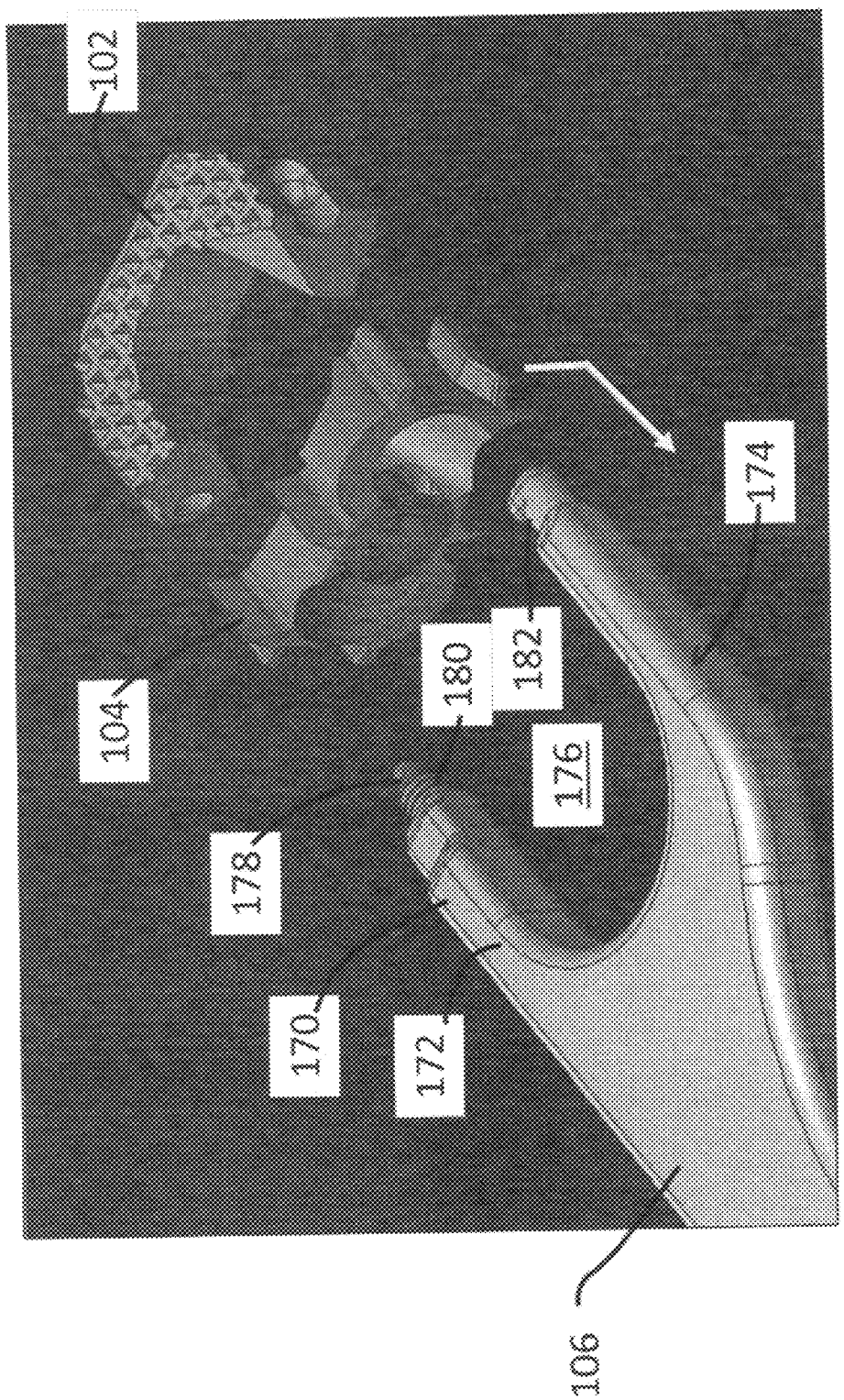
FIG. 16 is a perspective view of the assembly components shown in FIG. 1 and an insertion tool for inserting the assembly.
Figure 17:
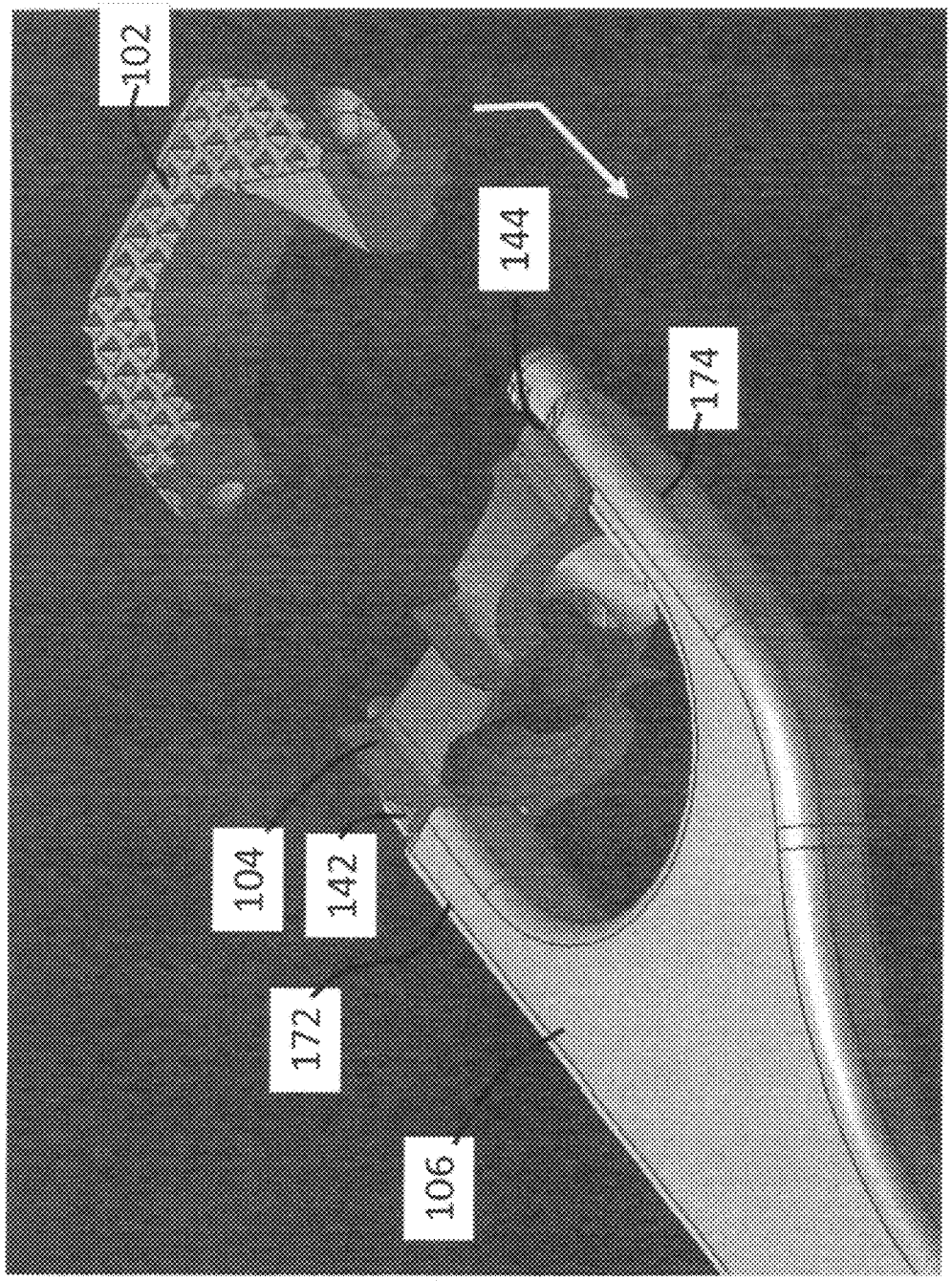
FIG. 17 is a perspective view showing the plate of FIG. 7 having been inserted onto the insertion tool.
Figure 18:
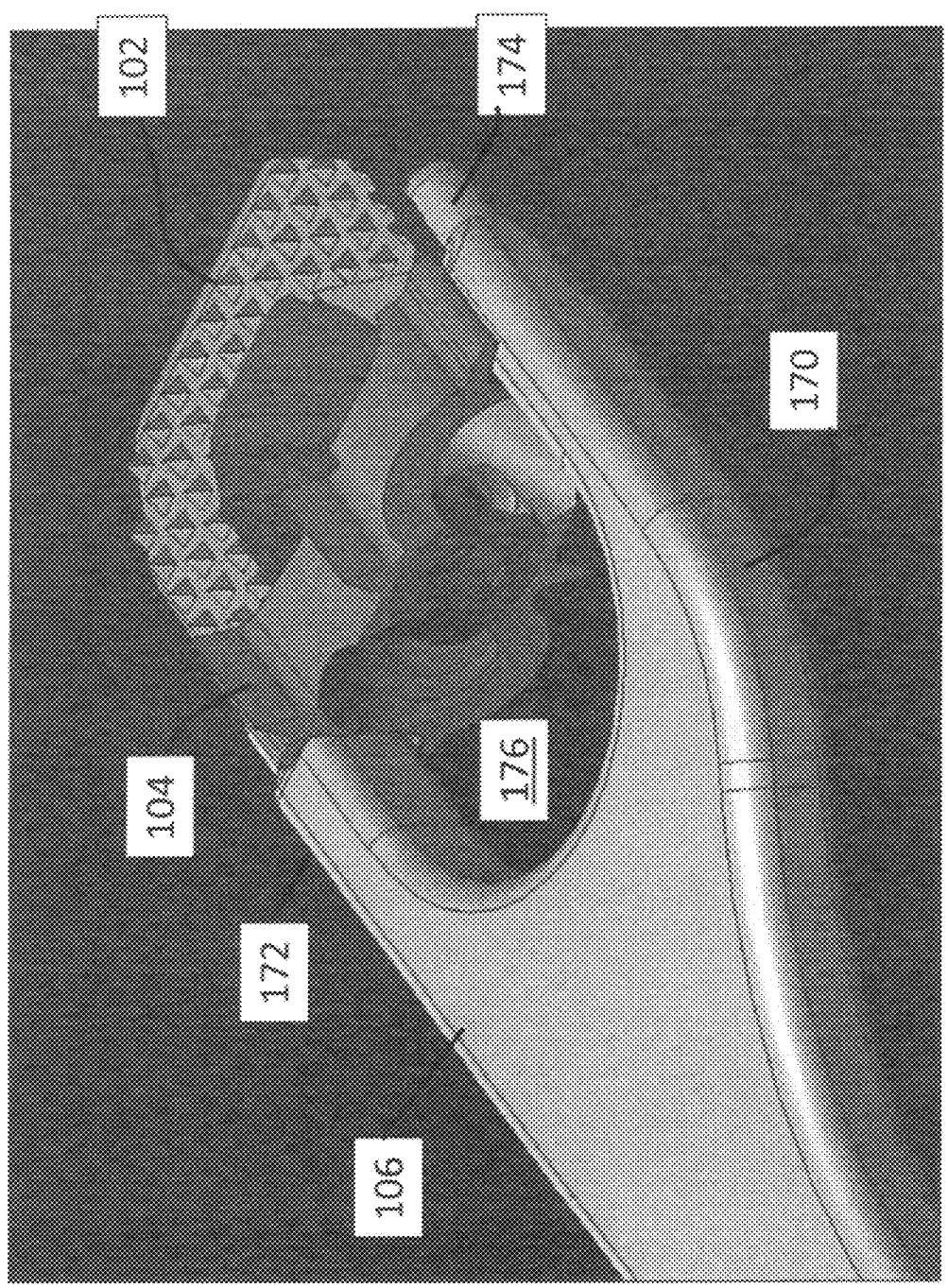
FIG. 18 is a perspective view showing the spacer and plate assembly of FIG. 1 having been inserted onto the insertion tool.
Figure 19:
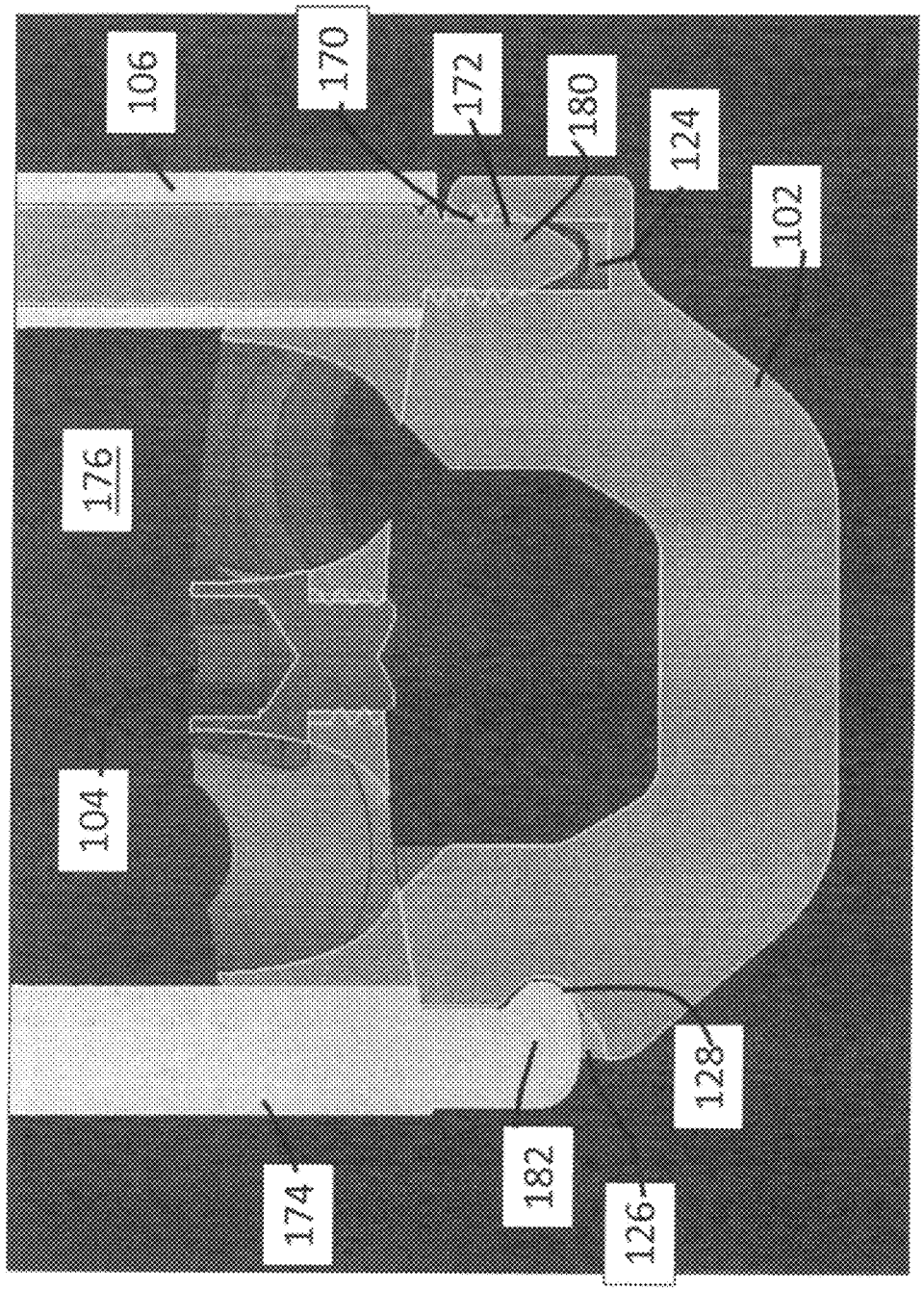
FIG. 19 is a top plan view, in section, of the plate and spacer of the assembly shown in FIG. 1 having been inserted onto the insertion tool.

Referring now to FIGS. 16-19, insertion tool 106 is used to insert spacer 102 and plate 104. Insertion tool 106 includes a distal end 170 having a first distal finger 172 and a second distal finger 174 that extends generally parallel to first distal finger 174. A gap 176 between fingers 172, 174 forms a generally U-shaped cavity 176 that is sized to accept plate 104 therein, as shown in FIG. 17. This gap advantageously provides space for a surgeon to use a tool to insert one or more bone screws or anchors into the plate. First distal finger 172 includes a rod 178 having a threaded end 180 that threads into threaded passage 124 in tubular protrusion 122 on spacer 102, as shown in FIG. 19. Rod 178 has a proximal end (not shown) that can be rotated by the surgeon to threadingly secure threaded end 180 into threaded passage 124.

Second distal finger 174 includes a prong 182 that extends generally toward first distal finger 172. Prong 182 is sized to fit into anterior end 128 of slot 126 on spacer 102.

While a single insertion tool 106 is shown, those skilled in the art will recognize that multiple insertion tools can be used. For example, a first insertion tool having only first distal finger 172 can be used in conjunction with a second insertion tool having only second distal finger 174.

According to one embodiment, a method of installing assembly 100, for example, at the site of two adjacent vertebrae (not shown), may include providing spacer 102, plate 104, and insertion tool 106 as a kit, as shown in FIG. 16. Referring to FIG. 17, plate 104 is connected to insertion tool 106 such that distal end 170 of insertion tool 106 extends distally of plate 104 (shown in FIG. 19). Plate 104 is connected to insertion tool 106 by attaching plate 104 to each of first finger 172 and second finger 174. First finger 172 is inserted into slot 142, while second finger 174 is inserted into second slot 144. Plate 104 is slid proximally onto each of first finger 172 and second finger 174, with plate 104 engaging each of first finger 172 and second finger 174 with an interference fit.

Next, as shown in FIGS. 18 and 19, spacer 102 is attached to distal end 170 of insertion tool 106 by attaching spacer 102 to each of first finger 172 and second finger 174. Sequentially or simultaneously, first finger 172 is connected to spacer 102 by threading threaded end 180 that threads into threaded passage 124 in tubular protrusion 122 on spacer 102 and inserting prong 182 on second finger 174 into slot 126 on spacer 102 and sliding spacer 102 proximally until prong 182 engages anterior end 128 of slot 126, thereby frictionally engaging second finger 174 with spacer 102.

After assembly 100 is attached to insertion tool 106, spacer 102 is inserted between adjacent vertebrae. Gap 176 is sufficiently large between plate 104 and insertion tool 106 to allow securing devices, such as, for example, screws (not shown) to be inserted through through-holes 160, 162, and into inferior vertebra and superior vertebra, respectively, securing plate 104 to the vertebrae. After securing plate 104 to the vertebrae, insertion tool 106 is removed, leaving spacer 102 and plate 104, as separate components, in the patient's spinal column. While the plate 104 and spacer 102 are attached to the insertion tool 106 upon delivery to a surgical site, once the insertion tool 106 is removed, the plate 104 and spacer 102 can be viewed as decoupled or independent from one another.

An alternative embodiment of an intervertebral spacer and plate assembly 200 ("assembly 200") is shown in FIGS. 20-28. In an exemplary embodiment, assembly 200 can be used for lumbar repair, although those skilled in the art will recognize that assembly 200 can be sized for thoracic or cervical repair as well.

Assembly 200 is formed from two separate components, an intervertebral spacer 202 ("spacer 202") and a plate 204 ("plate 204"). In some embodiments, spacer 202 and plate 204 are not connected to each other, but are instead each separately coupled to an insertion tool 206, as shown in FIGS. 25-28.

Referring to FIGS. 20 and 22-24, spacer 202 includes a body 208 having a superior surface 210 and an opposing inferior surface 212. Each of superior surface 210 and inferior surface 212 can have a plurality of protrusions or fixation elements 214 extending outwardly therefrom. While fixation elements 214 are shown as being generally pyramidal in shape, those skilled in the art will recognize that fixation elements 214 can be other shapes, such as ribbed, or other suitable shapes. Fixation elements 214 are used to bite into a grip each of adjacent vertebrae (not shown) between which spacer 202 is inserted.

Figure 20:
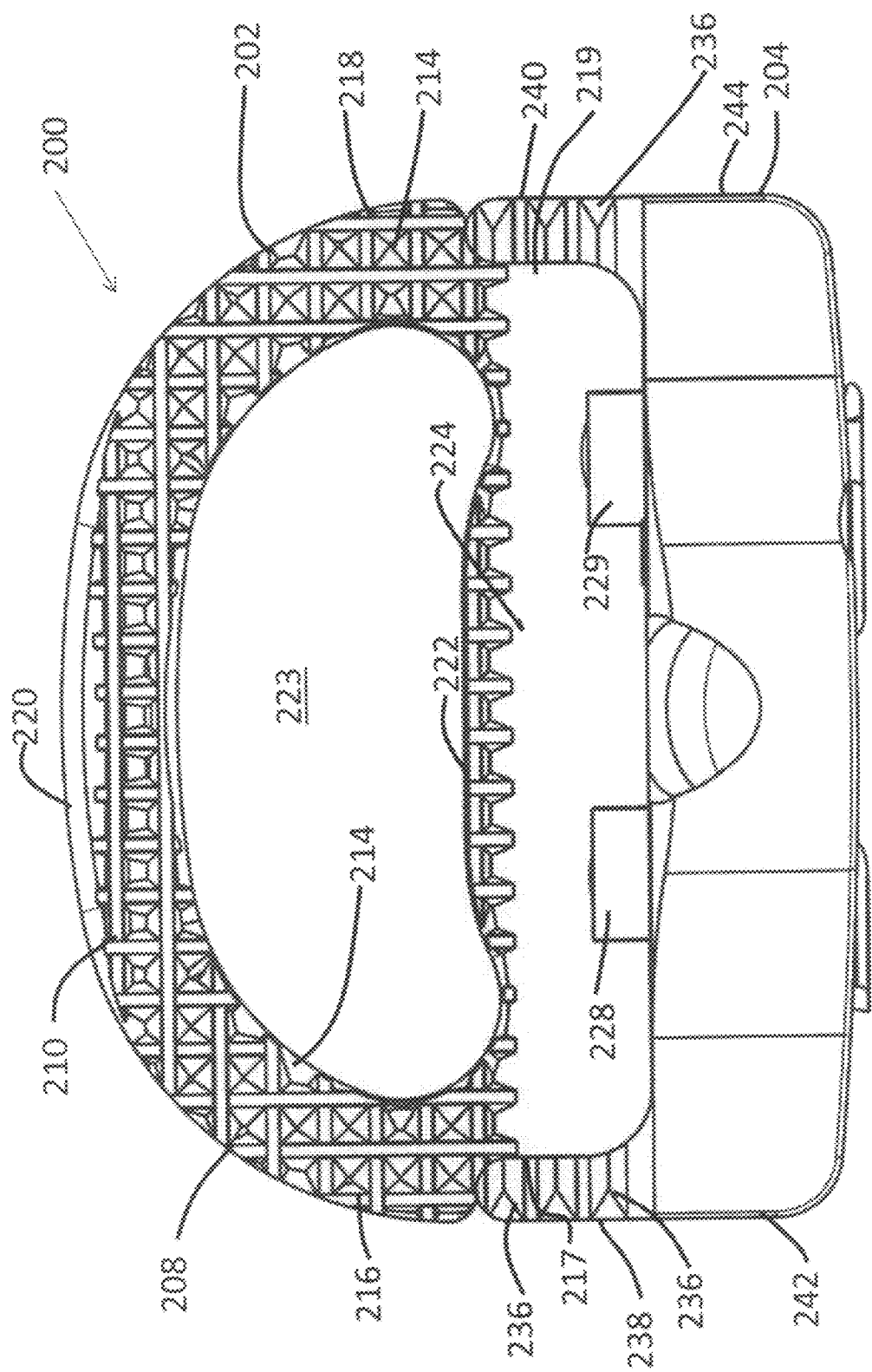
FIG. 20 is a top plan view of a spacer and plate assembly according to a second exemplary embodiment.

As shown in FIG. 20, body 202 can have a generally oblong shape, with generally arcuate lateral sides 216, 218, connected to each other by an anterior portion 220 and a posterior portion 222. Lateral side 216 includes an indentation 217 while lateral side 218 includes a similar indentation 219. Indentations 217, 219 reduce the lateral length of posterior portion 222 relative to the remaining lateral length of spacer 202. A space 223 bounded by lateral sides 216, 218, anterior portion 220, and posterior portion 222 can optionally be filled with graft material.

Posterior portion 222 includes a first chamfered face 224 that extends in an inferior direction posteriorly from superior surface 210 and a second chamfered face 226 (shown in FIG. 23) that extends in a superior direction posteriorly from inferior surface 212. Chamfered faces 224, 226 allow for securing screws (not shown) to be inserted through plate 204, along chamfered faces 224, 226, respectively, and into adjacent vertebrae (not shown) without engaging spacer 202.

Posterior portion 222 also includes a smooth, anteriorly directed hole 228 proximate to lateral side 216. Hole 228 is sized to accept a non-threaded portion of insertion tool 206 as will be explained in detail below. Posterior portion 222 also includes a threaded, anteriorly directed hole 229 proximate to lateral side 218. Hole 229 is sized to accept a threaded portion of insertion tool 206 as will be explained in detail below.

Referring now to FIGS. 20-24, plate 204 includes a body 230 having a superior surface 232 and an opposing inferior surface 234. Each of superior surface 232 and inferior surface 234 can have a plurality of stabilizer elements 236 extending outwardly therefrom. In some embodiments, the stabilizer elements 236 can be for torsional stabilization. In an exemplary embodiment, stabilizer elements 236 are located along fingers 238, 240 that extend anteriorly from plate 204. While stabilizer elements 236 are shown as being generally ribbed in shape, those skilled in the art will recognize that stabilizer elements 236 can be other shapes, such as pyramidal, or other suitable shapes. Stabilizer elements 236 are used to bite into a grip each of adjacent vertebrae (not shown) between which spacer 202 is inserted.

As shown in FIG. 20, body 230 can have a generally laterally elongate shape, with generally parallel lateral sides 242, 244. Fingers 238, 240 extend from lateral sides 242, 244, respectively. Fingers 238, 240 are sized to fit into indentations 217, 219 respectively, while a space between fingers 238, 340 is sized to allow posterior portion 222 of spacer 202 to be inserted therein.

Referring to FIG. 21, through-holes 260, 262 extend through body 230 in a posterior-to-anterior direction. Through-holes 260, 262 are located on plate 204 to align with holes 228, 229 when plate 204 and spacer 202 are coupled as shown in FIG. 20. Through-hole 260 can be smooth bored to allow for the passage of the non-threaded portion of insertion tool 206. Through-hole 262 can be smooth bored or threaded to allow for the insertion of the threaded portion of insertion tool 206.

Additional through-holes 264, 266, 268 are provided in plate 204 and are sized to allow a securing screw (not shown) to be inserted therethrough to secure plate 204 to each of a superior vertebra (not shown) and an inferior vertebra (not shown), between which spacer 202 is being inserted. Through-holes 264, 266 each extends in a superior-to-inferior direction so that their respective screw each engages and secures to the inferior vertebra, while through-hole 268 extends in an inferior-to-superior direction so that its screw engages and secures the superior vertebra.

Referring to FIG. 21, locking screws 270, 272, 274 are each is disposed adjacent to a respective through-hole 264, 266, 268. Each locking screw 270, 272, 274 has a head 276, 278, 280 with an arcuate cutout 282, 284, 286, respectively, that is sized to allow the securing screws discussed above to be inserted into through-holes 264, 266, 268. During insertion of assembly 200, locking screws 264, 266, 268 are in a configuration relative to plate 204 as shown in FIG. 21. After the securing screws secure plate 204 to the superior and inferior vertebra, locking screws 270, 272, 274 are rotated, for example, about 90 degrees, so that heads 276, 278, 280 each extends over its adjacent securing screws, preventing the securing screws from inadvertently backing out.

FIGS. 20-24, 27, and 28 show assembly 200. While plate 204 is butted up against spacer 202 to form a coupled construct, plate 204 is not connected to spacer 202 so that spacer 202 and plate 204 remain separate, independent components that can be implanted together or on their own as part of a fusion procedure.

Referring now to FIGS. 25-28, insertion tool 206 is used to insert spacer 202 and plate 204. Insertion tool 206 includes a distal end 282 having a first distal finger 284 and a second distal finger 286 that extends generally parallel to first distal finger 282. First distal finger 282 is a generally smooth bore rod that is sized to pass through through-hole 260 in plate 204 and into hole 228 in spacer 202.

Figure 25:
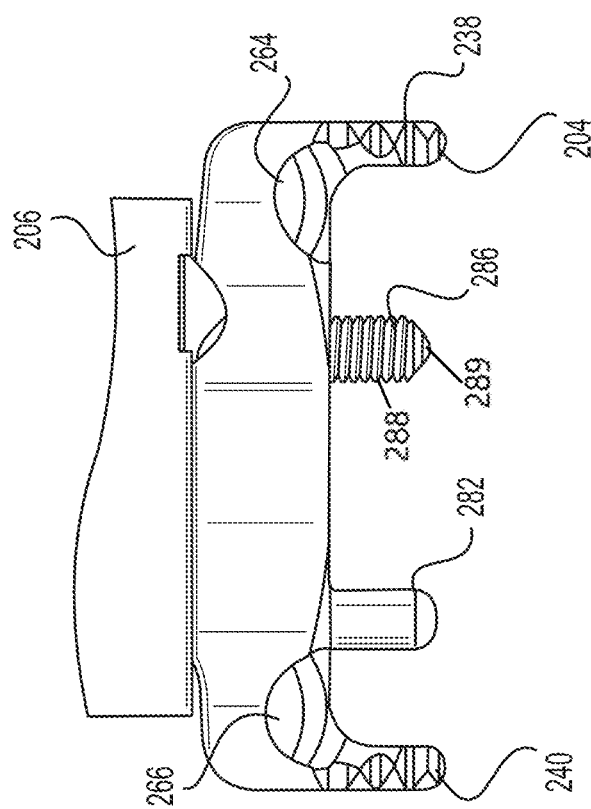
FIG. 25 is a top plan view, in section, of the plate of FIG. 20 and an insertion tool for inserting the plate.
Figure 27:
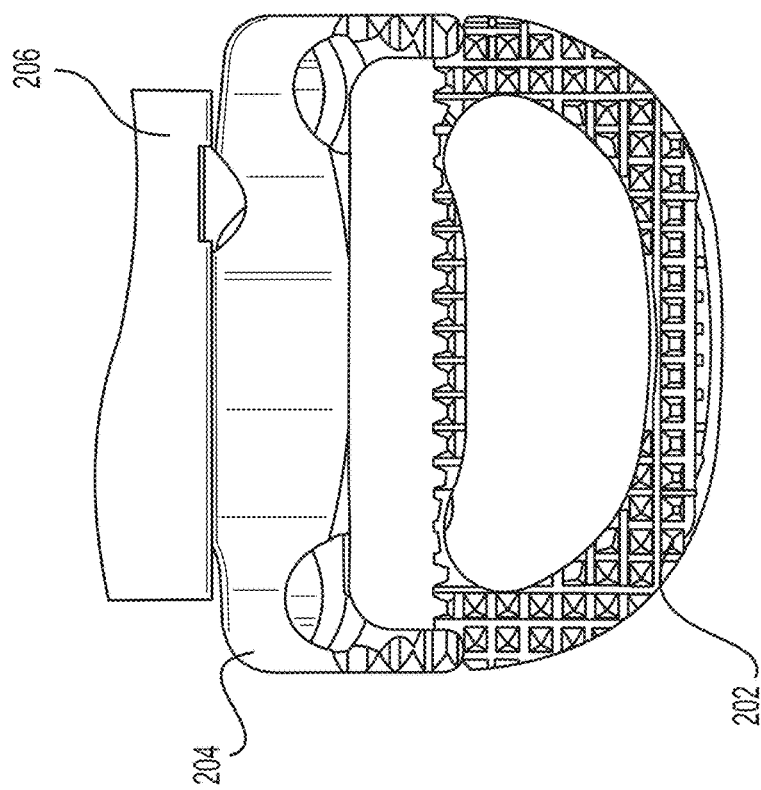
FIG. 27 is a top plan view, in section, of the assembly of FIG. 20 and the insertion tool for inserting the assembly.

Second distal finger 286 includes a rod 288 having a threaded end 290 that threads into threaded through-hole 262 in plate 204, as shown in FIG. 25, as well as into hole 229 in spacer, as shown in FIG. 27. Rod 288 has a proximal end (not shown) that can be rotated by the surgeon to threadingly secure threaded end 290 into hole 229.

While a single insertion tool 206 is shown, those skilled in the art will recognize that multiple insertion tools can be used. For example, a first insertion tool having only first distal finger 282 can be used in conjunction with a second insertion tool having only second distal finger 286.

Figure 28:
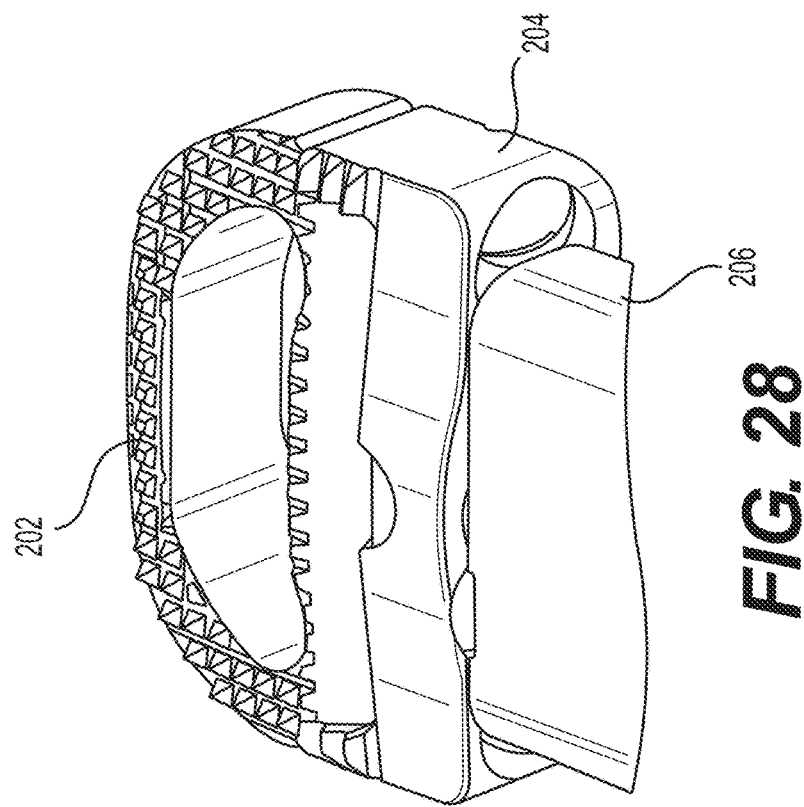
FIG. 28 is a perspective view of the assembly and insertion tool of FIG. 27.

According to one embodiment, a method of installing assembly 200, for example, at the site of two adjacent vertebrae (not shown), may include providing spacer 202, plate 204, and insertion tool 206 as a kit, as shown in FIG. 28.

As shown in FIGS. 23 and 24, plate 204 is releasably engaged with spacer 202 in the absence of securing plate 204 to spacer 202 such that plate 204 engages spacer 202 between first finger 238 and second finger 240, as shown in FIG. 20.

Next, insertion tool 206 is inserted through plate 204 and into spacer 202. Such insertion is performed by inserting insertion tool 206 through first through-hole 260 and second through-hole 262 and into holes 228, 230 of spacer 202. This is accomplished by threading threaded finger 286 of insertion tool 206 into plate 204 and into hole 229 in spacer 202, as well as inserting unthreaded finger 282 of insertion tool 206 through plate 204 and into hole 228 in spacer 202.

Next, spacer 202 is implanted between adjacent vertebrae. Insertion tool 206 is removed such that spacer 202 is separate from plate 204. Next, plate 204 is connected to the vertebrae.

Figure 26:
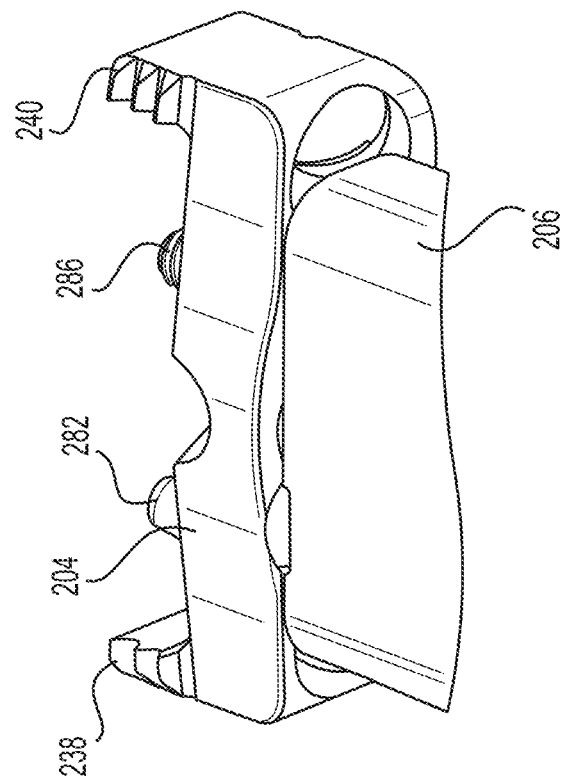
FIG. 26 is a perspective view of the plate and insertion tool of FIG. 25.

Optionally, as shown in FIGS. 25 and 26, insertion tool 206 can be releasably secured to only plate 204. Then, plate 204 can be coupled to spacer 202, after which time insertion tool 206 is then releasably secured to spacer 202.

A situation may arise wherein plate 204 is not required to secure spacer 202 between adjacent vertebrae; the compression of vertebrae toward each other is sufficient to maintain spacer 202 in place. In such a situation, plate 204 can be omitted. It is desired, however, to incorporate a substitute for plate 204 in order to provide desired spacing between plate 202 and insertion tool 206.

Figure 30:
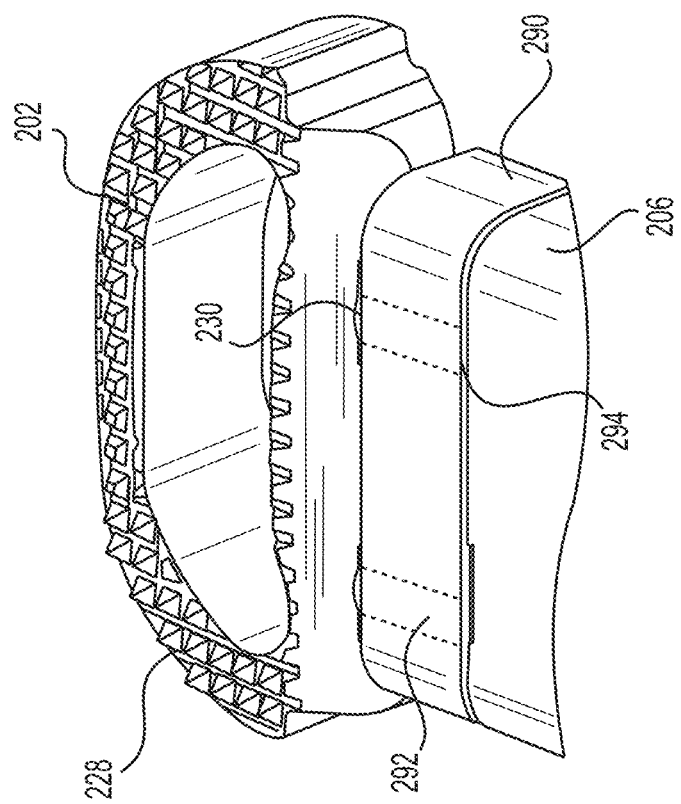
FIG. 30 is a perspective view of the spacer block, spacer, and insertion tool of FIG. 29.
Figure 29:
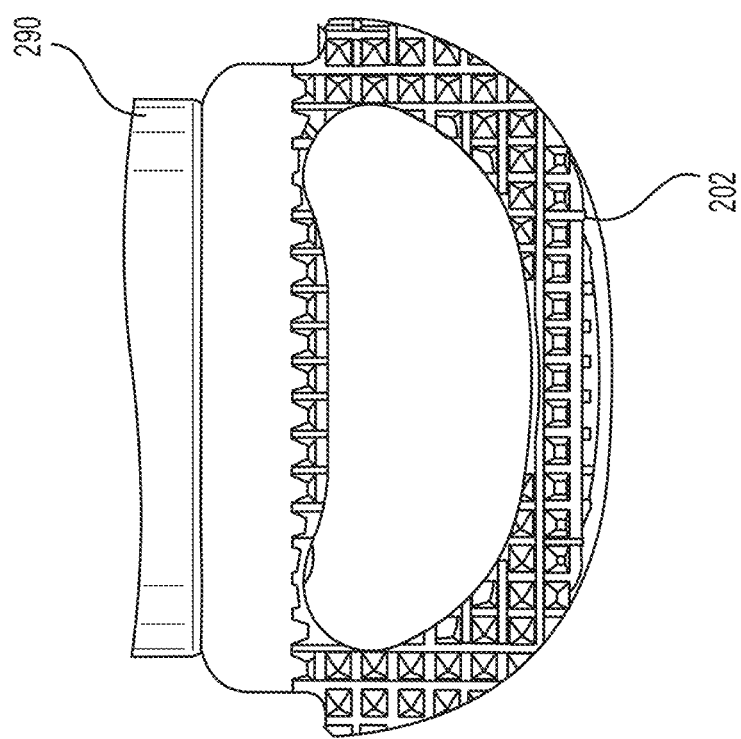
FIG. 29 is a top plan view, in section, of a spacer block and the spacer and insertion tool of FIG. 27.

To achieve this spacing, as shown in FIGS. 29 and 30, a spacer block 290 is provided. Spacer block 290 has substantially the same anterior-to-posterior width as plate 204, but without fingers 238, 240. Spacer block 290 includes a pair of unthreaded, smooth bore through-holes 292, 294 that align with holes 228, 230 of spacer 202 so that fingers 282, 286 of insertion tool 206 can be inserted therethrough and into hole 228, 230 of spacer 202 for insertion of spacer 202 between adjacent vertebrae (not shown).

An alternative embodiment of an intervertebral spacer and plate assembly 300 ("assembly 300") is shown in FIGS. 31-39. In an exemplary embodiment, assembly 300 can be used for lumbar repair, although those skilled in the art will recognize that assembly 300 can be sized for thoracic or cervical repair as well.

Figure 39:
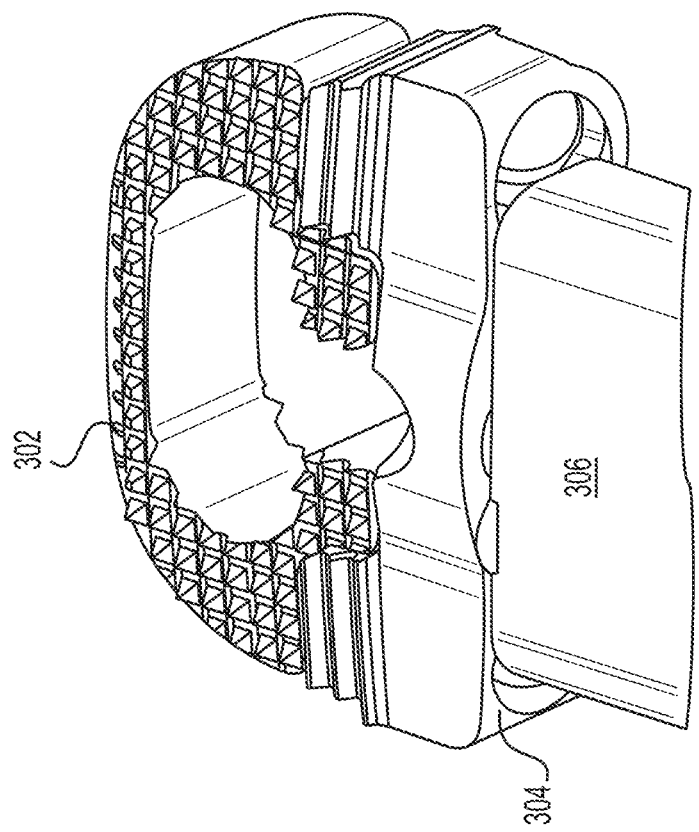
FIG. 39 is a perspective view of the assembly and insertion tool of FIG. 38.
Figure 38:
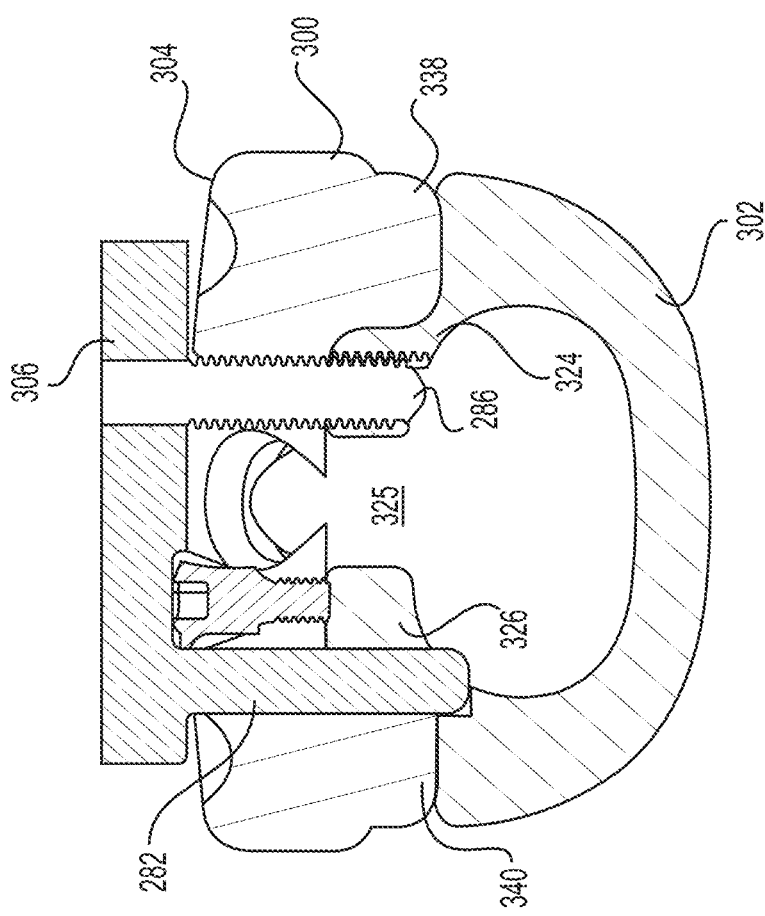
FIG. 38 is a top plan view, in section, of the assembly of FIG. 31 and the insertion tool for inserting the assembly.

Assembly 300 is formed from two separate components, an intervertebral spacer 302 ("spacer 302") and a plate 304 ("plate 304"). In some embodiments, spacer 302 and plate 304 are not connected to each other, but are instead each separately coupled to an insertion tool 306, as shown in FIGS. 38 and 39.

Figure 31:
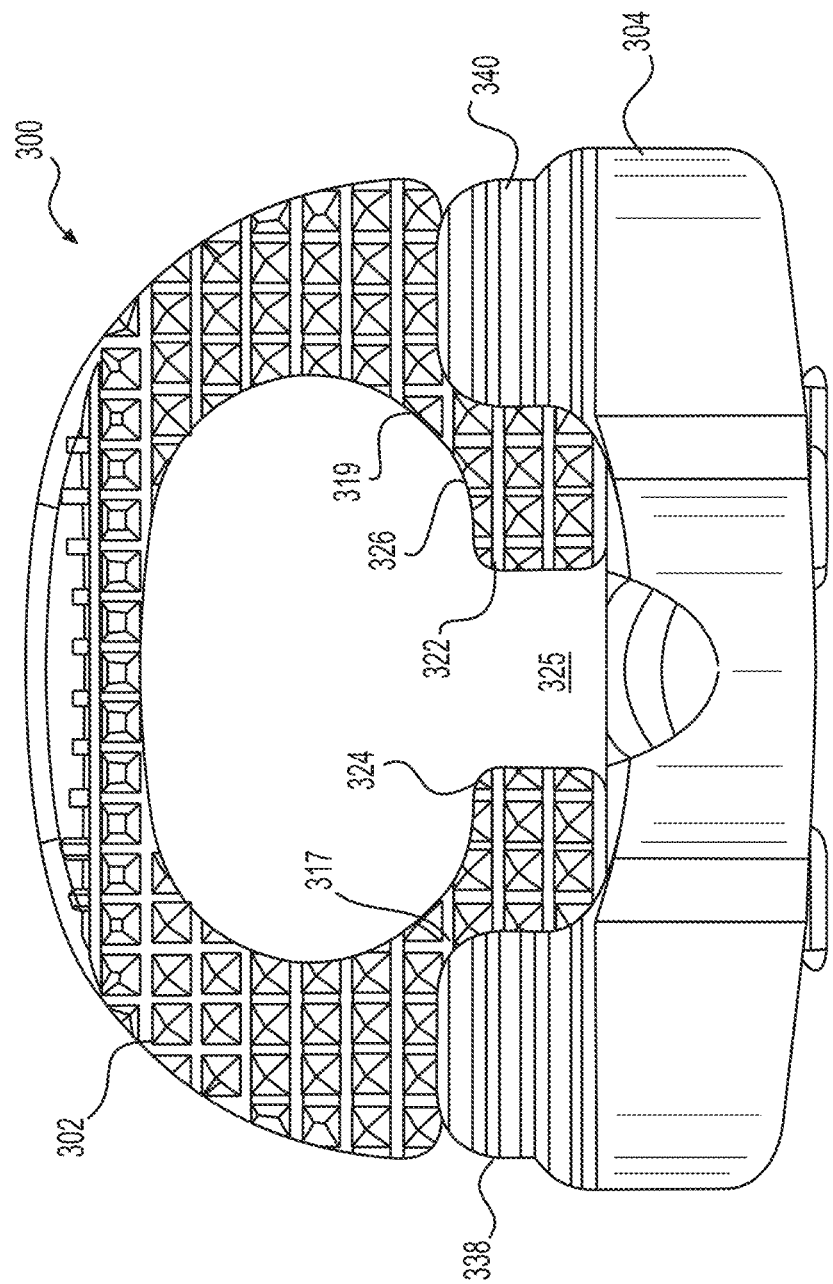
FIG. 31 is a top plan view of a spacer and plate assembly according to a third exemplary embodiment.
Figure 32:
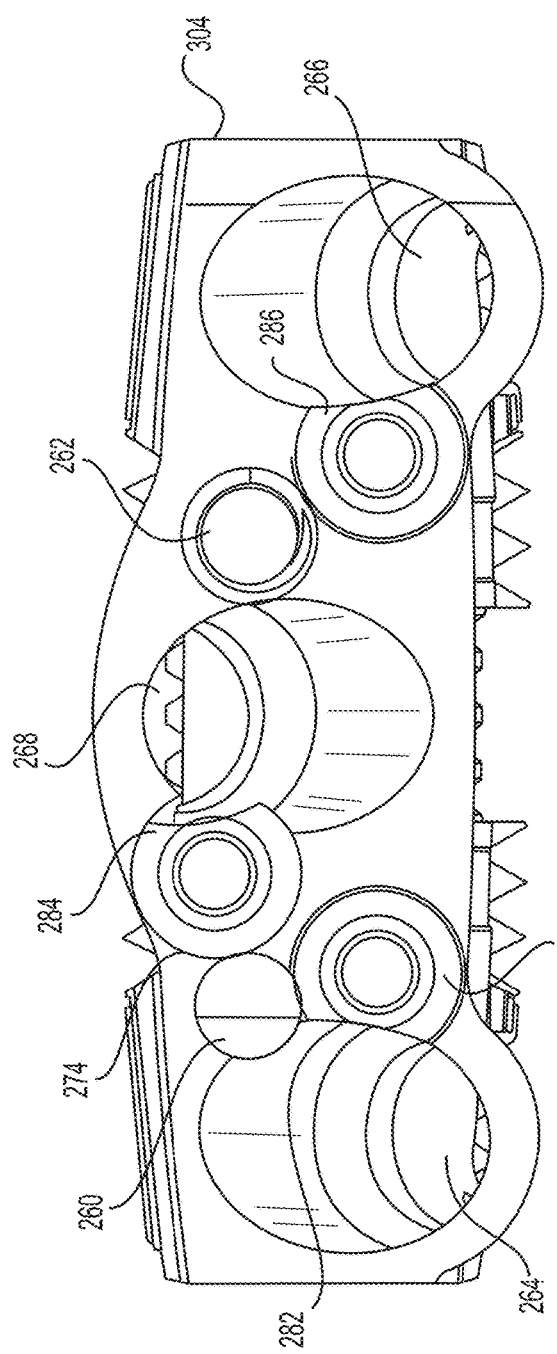
FIG. 32 is a posterior elevational view of the assembly shown in FIG. 31.
Figure 33:
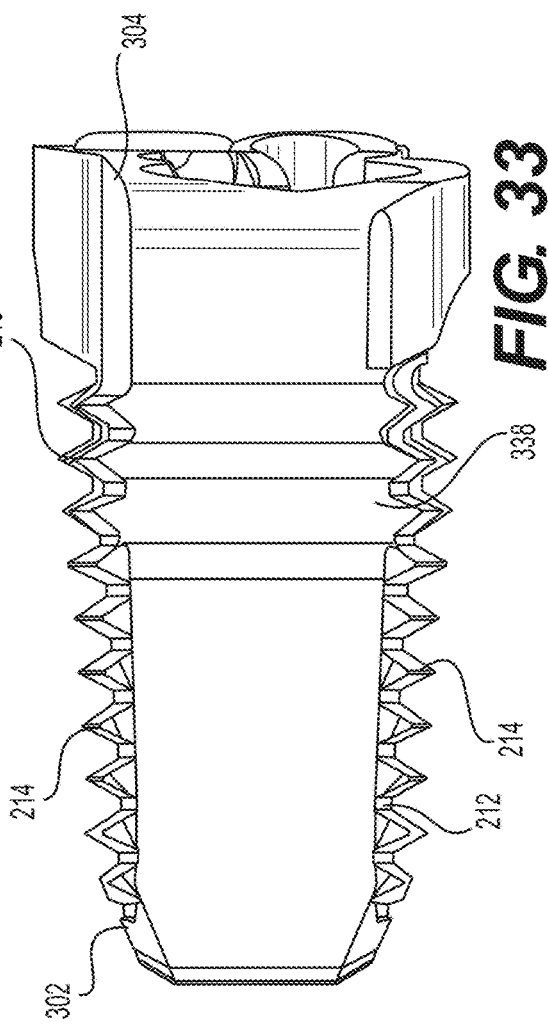
FIG. 33 is a left lateral side elevational view of the assembly shown in FIG. 31.
Figure 34:
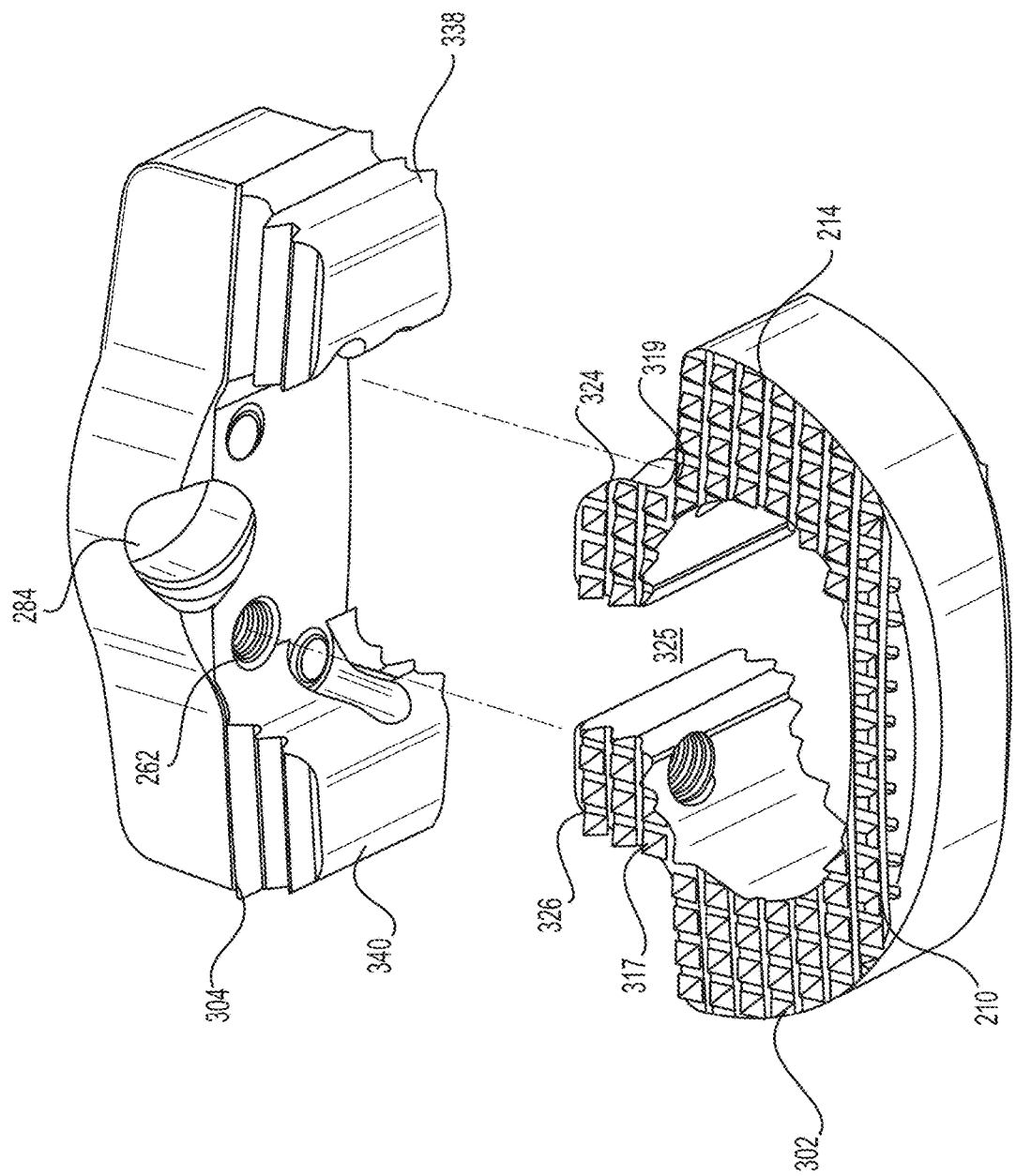
FIG. 34 is an exploded anterior perspective view of the assembly shown in FIG. 20.
Figure 35:
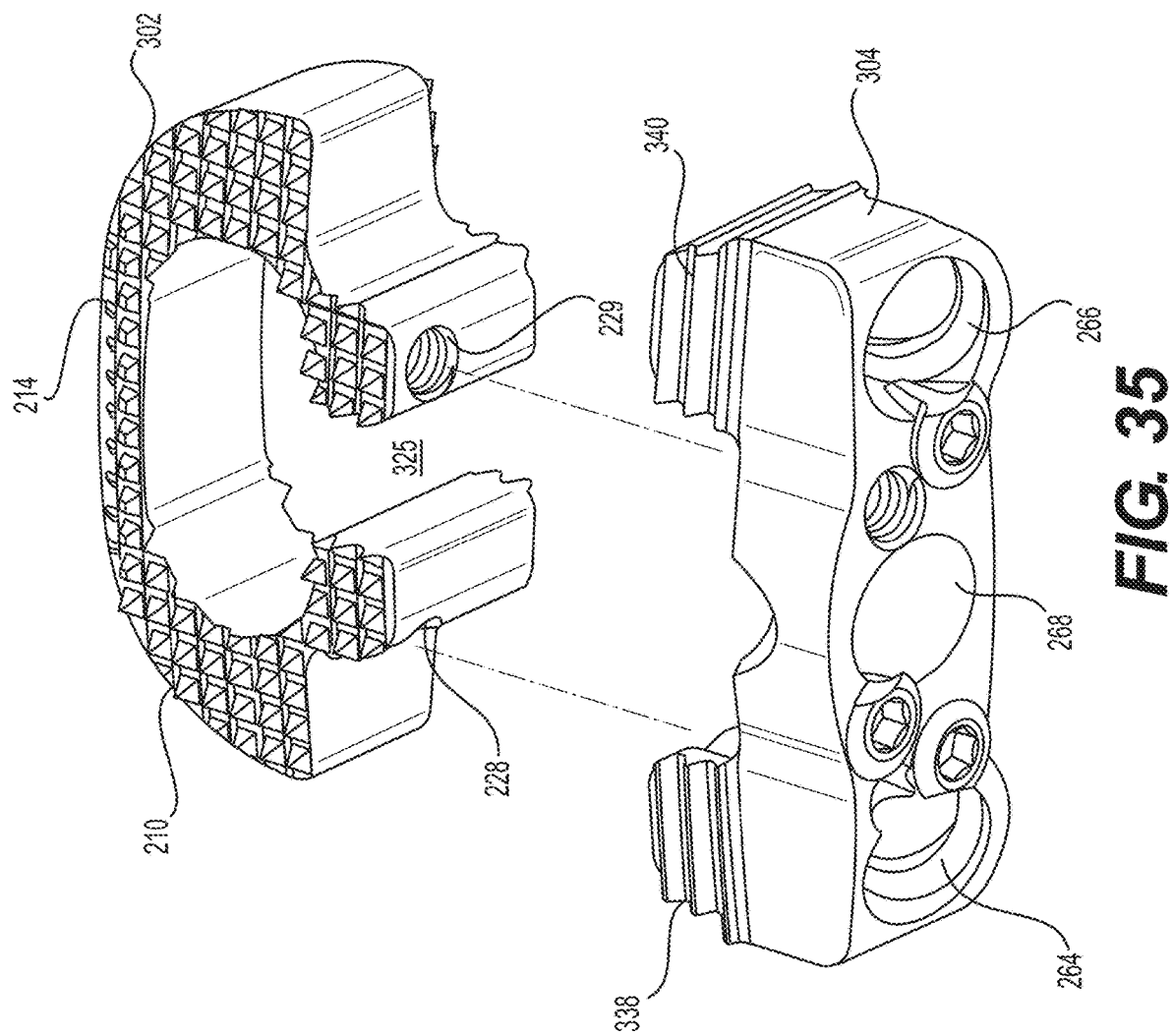
FIG. 35 is an exploded posterior perspective view of the assembly shown in FIG. 20.
Figure 37:
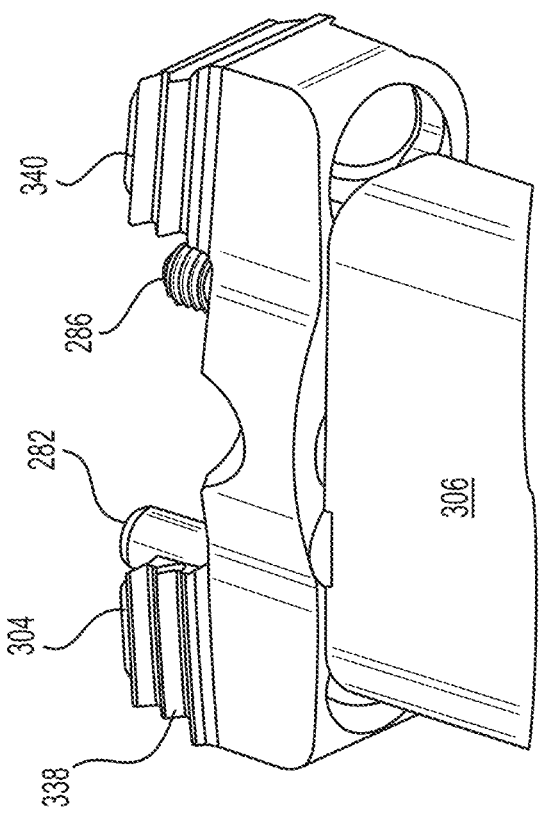
FIG. 37 is a perspective view of the plate and insertion tool of FIG. 36.
Figure 36:
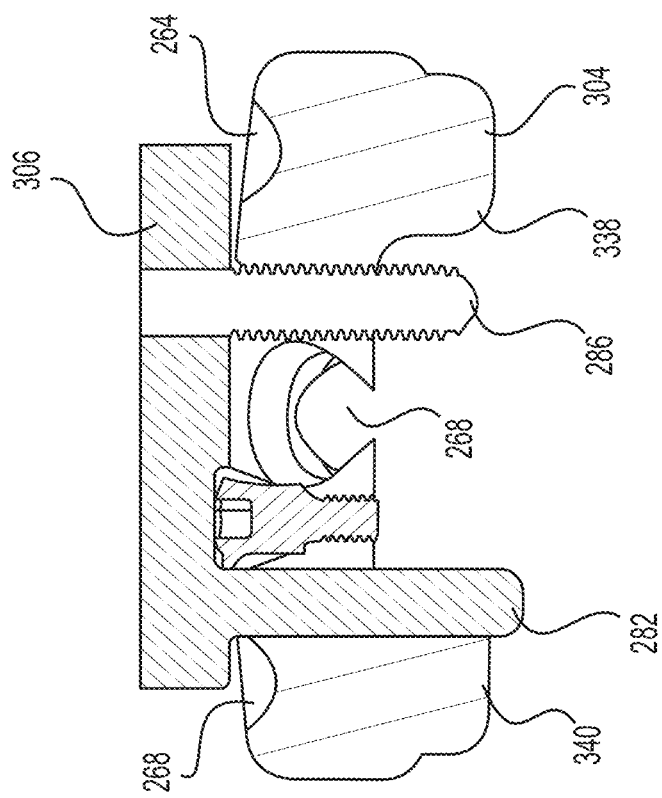
FIG. 36 is a top plan view, in section, of the plate of FIG. 31 and an insertion tool for inserting the assembly of FIG. 31.

Referring to FIGS. 31 and 34-35, spacer 302 is similar to spacer 202, but, instead of a solid posterior portion 222, posterior portion 322 of spacer 302 includes a gap 325 between two medially directed ends 324, 326. Gap 325 allows for spacer 302 to flex after insertion, which may provide enhanced mobility for the patient.

Additionally, spacer 302 includes indentations 317, 319 that are larger than indentations 217, 219 on spacer 202. Similarly, fingers 338, 340 on plate 304 are wider than fingers 238, 240 on plate 204 to accommodate the larger indentations 317, 319.

Other aspects of spacer 302, plate 304, and insertion tool 306 are similar, if not identical, to corresponding aspects of spacer 202, plate 204, and insertion tool 206 as discussed above. Those aspects are identified with element numbers corresponding to spacer 202, plate 204, and insertion tool 206 with respect to spacer 302, plate 304, and insertion tool 306, respectively.

Figure 41:
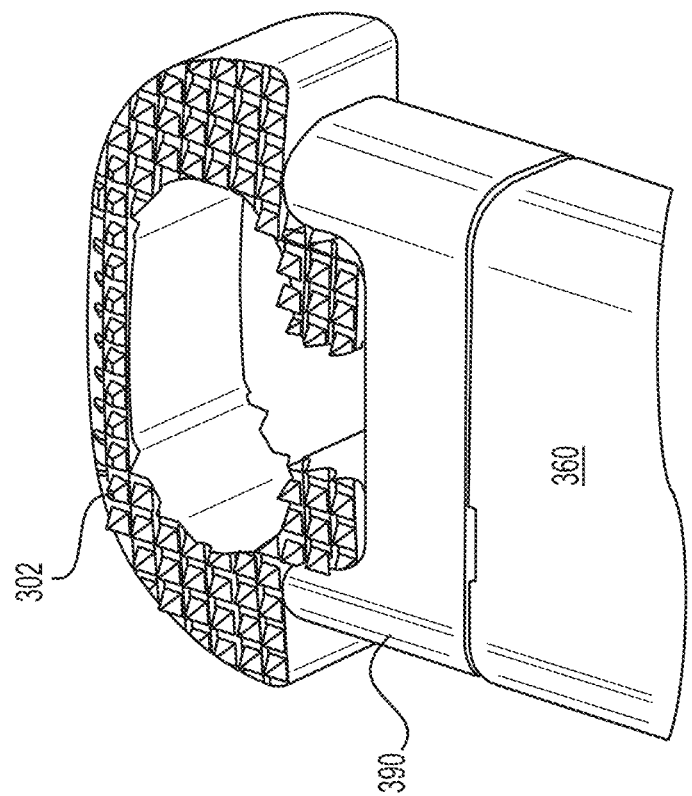
FIG. 41 is a perspective view of the spacer block, spacer, and insertion tool of FIG. 40.
Figure 40:
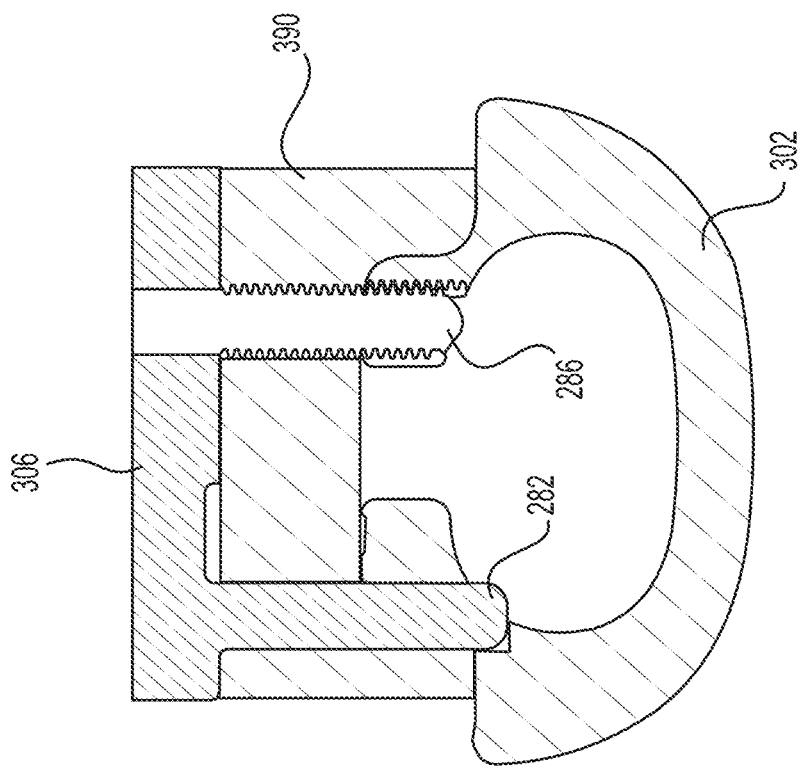
FIG. 40 is a top plan view, in section, of a spacer block and the spacer and insertion tool of FIG. 38.
Figure 41D:
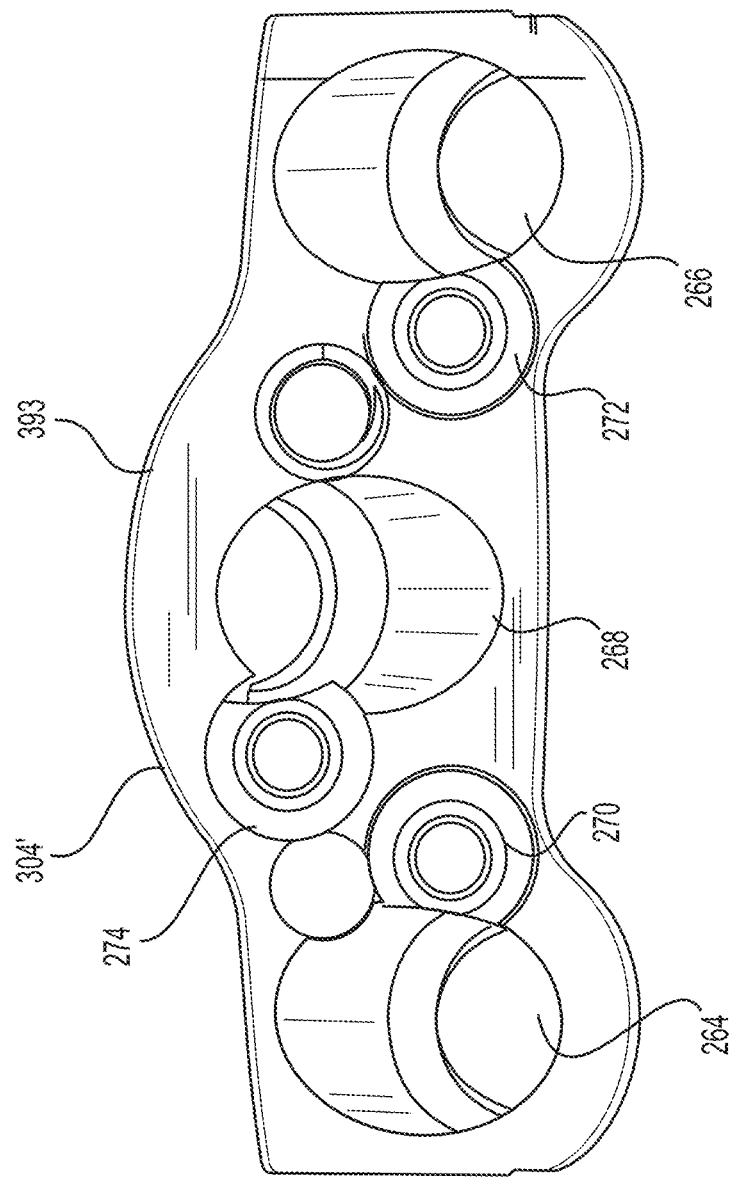
FIG. 41D is an anterior side elevational view of the plate shown in FIG. 41A.
Figure 41C:
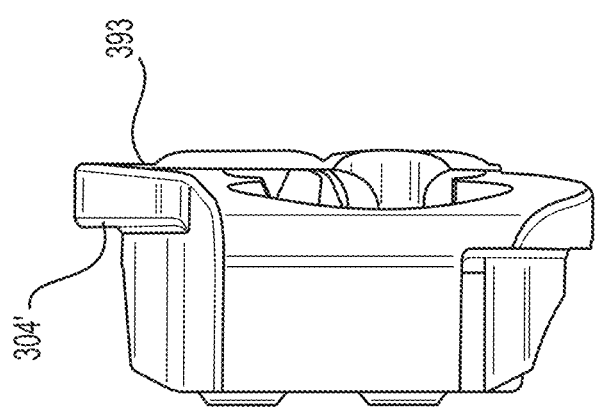
FIG. 41C is a left side elevational view of the plate shown in FIG. 41A.
Figure 42:
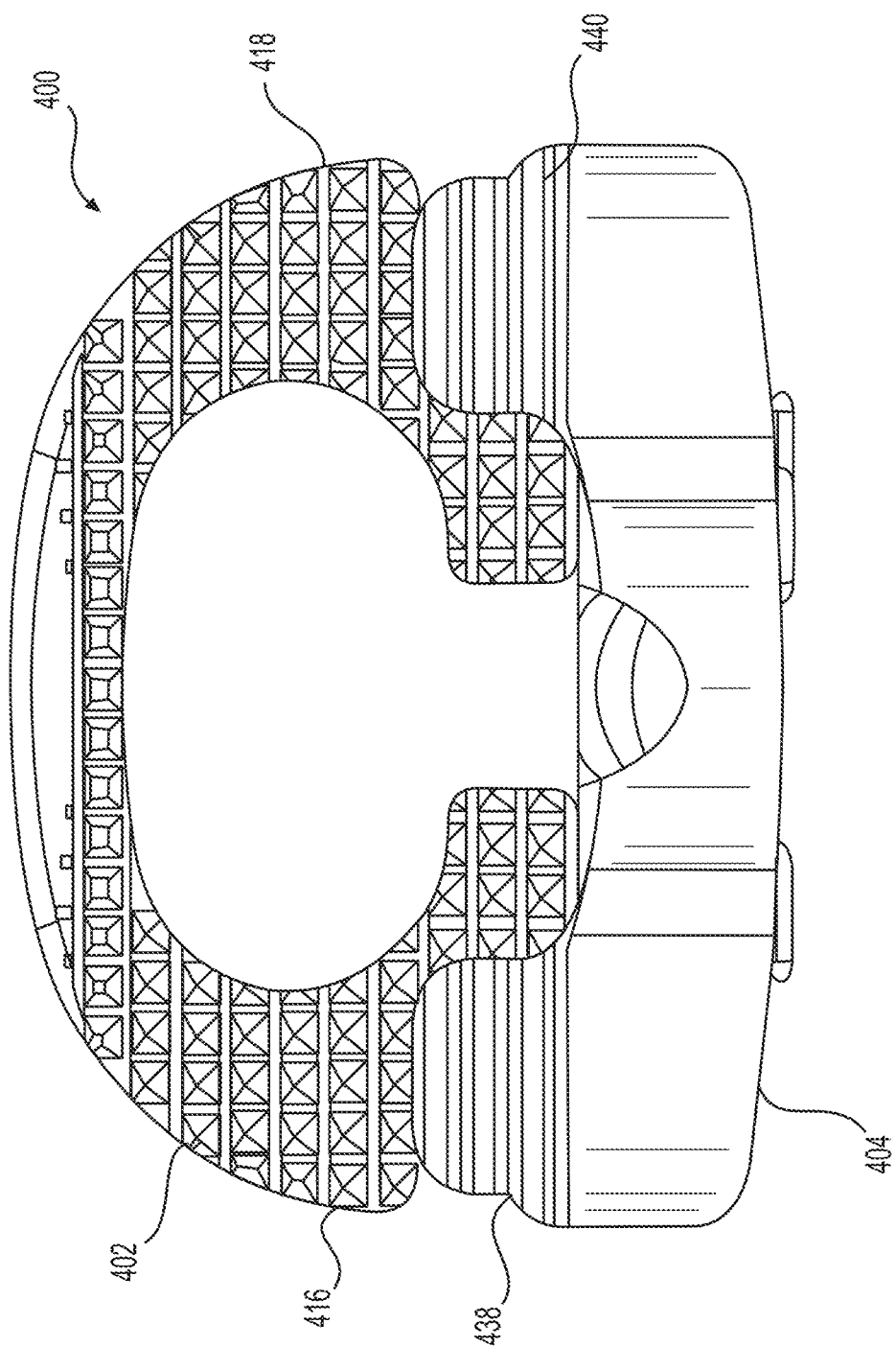
FIG. 42 is a top plan view of a spacer and plate assembly according to a fourth exemplary embodiment.
Figure 43:
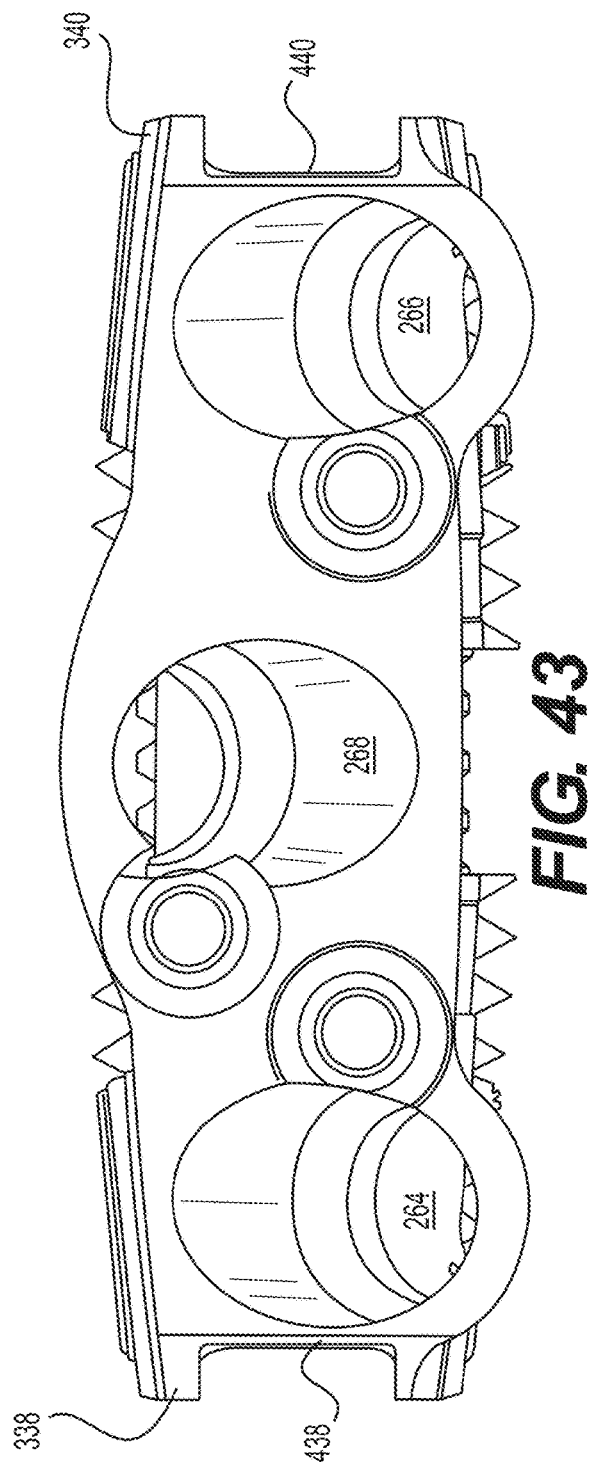
FIG. 43 is a posterior elevational view of the assembly shown in FIG. 42.
Figure 44:
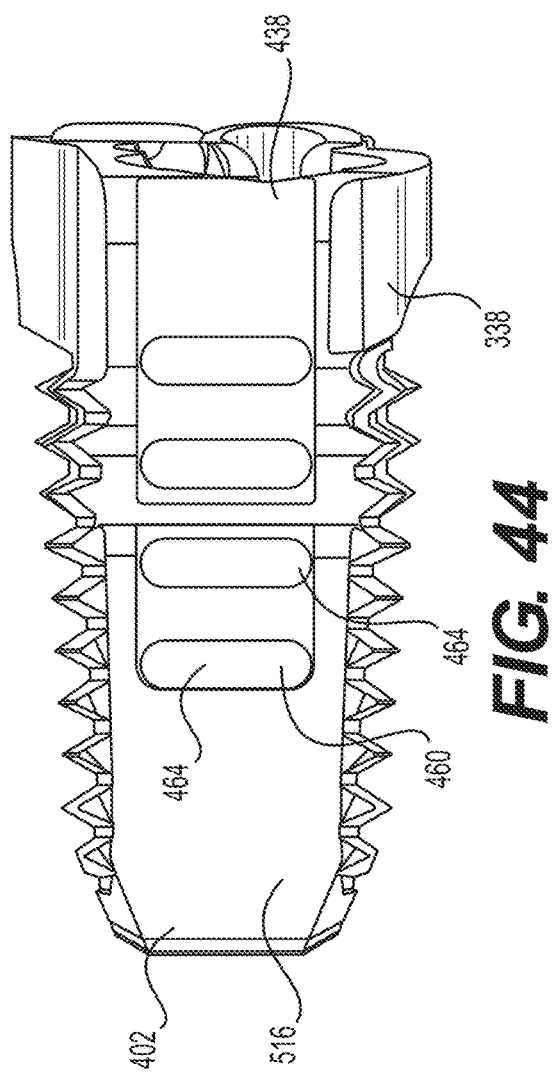
FIG. 44 is a left lateral side elevational view of the assembly shown in FIG. 42.

With respect to a spacer block 390 shown in FIGS. 40 and 41, however, spacer block 390 includes fingers 396, 398 that are insertable into indentations 317, 319. Other aspects of spacer block 390 are similar, if not identical, to corresponding aspects of spacer block 290 as discussed above.

Instead of plate 304, an alternative plate 304', shown in FIGS. 41A-41D can be provided. Plate 304' is similar to plate 304, with the addition of a superior extension 393 on the posterior end 394 of plate 304'. Extension 393 increases the overall height of plate 304' and allows plate 304' to be shouldered onto the vertebral body during insertion. As shown in FIG. 41B, extension 393 can be straight. Alternatively, extension 393 can be angled in a posterior direction.

An alternative embodiment of an intervertebral spacer and plate assembly 400 ("assembly 400") is shown in FIGS. 42-50. In an exemplary embodiment, assembly 400 can be used for lumbar repair, although those skilled in the art will recognize that assembly 400 can be sized for thoracic or cervical repair as well.

Figure 47:
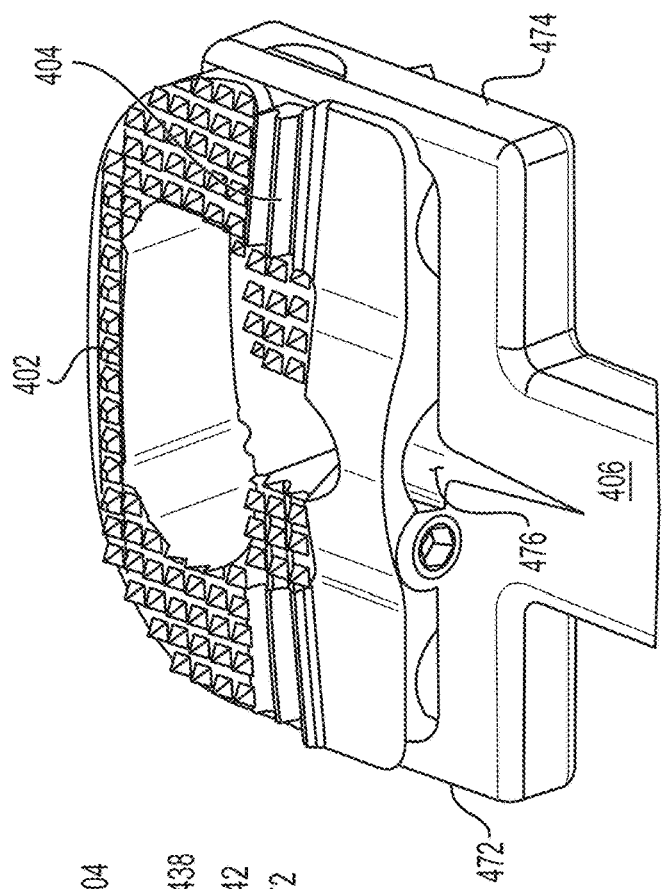
FIG. 47 is a top plan view, in section, of the plate of FIG. 42 and an insertion tool for inserting the assembly of FIG. 42.
Figure 48:
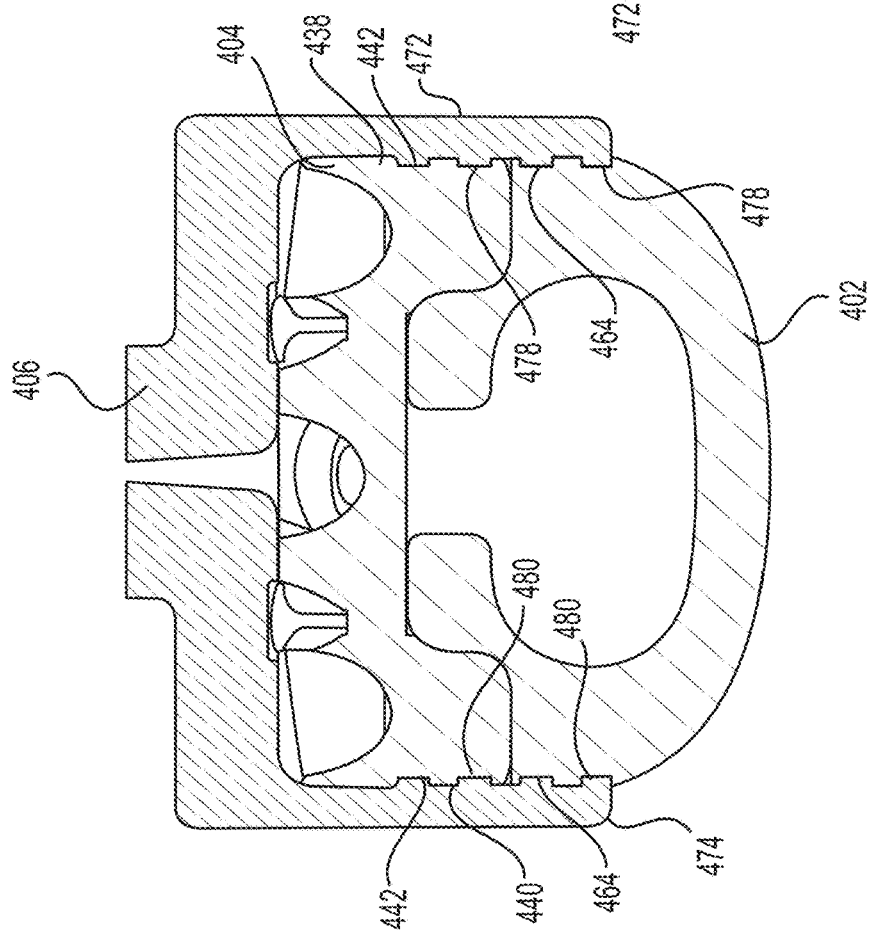
FIG. 48 is a perspective view of the plate and insertion tool of FIG. 47.
Figure 50:
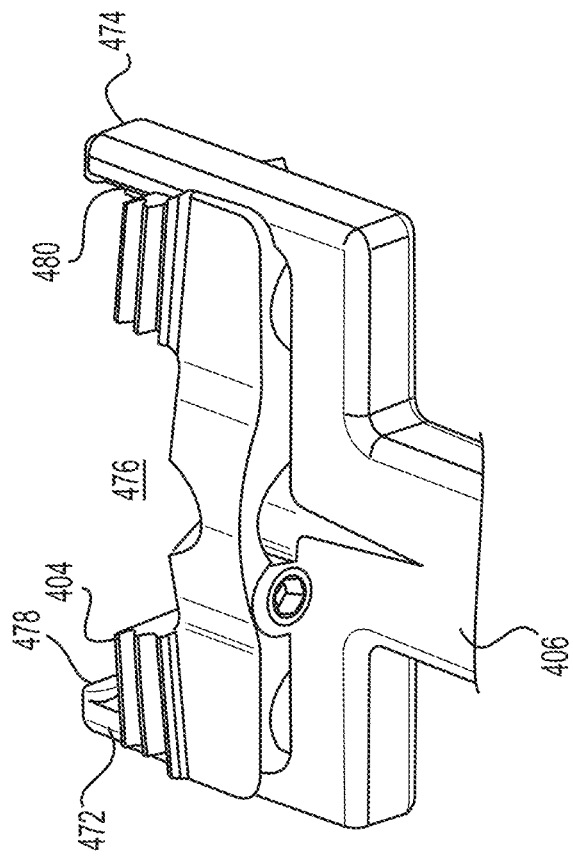
FIG. 50 is a perspective view of the assembly and insertion tool of FIG. 49.
Figure 49:
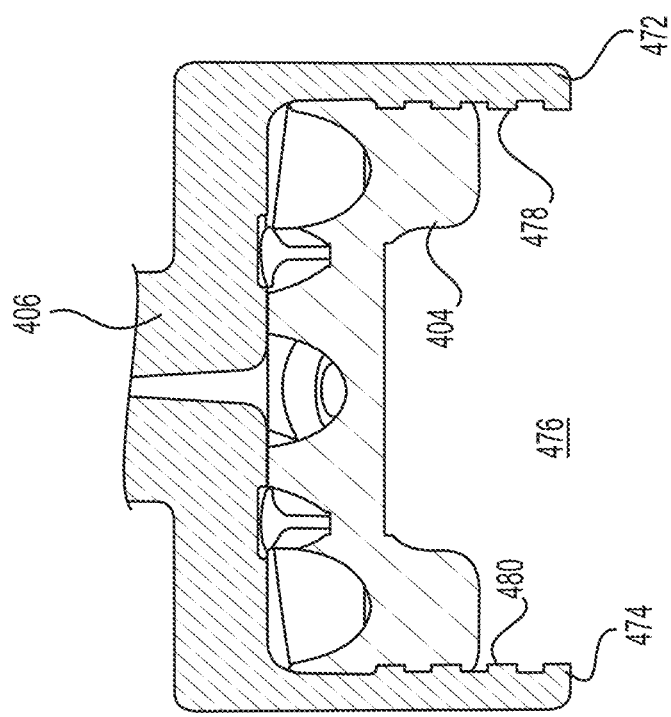
FIG. 49 is a top plan view, in section, of the assembly of FIG. 42 and the insertion tool for inserting the assembly.

Assembly 400 is formed from two separate components, an intervertebral spacer 402 ("spacer 402") and a plate 404 ("plate 404"). In some embodiments, spacer 402 and plate 404 are not connected to each other, but are instead each separately coupled to an insertion tool 406, as shown in FIGS. 47 and 48. Upon delivery to a surgical site, the spacer 402 and plate 404 can be decoupled from one another.

Figure 45:
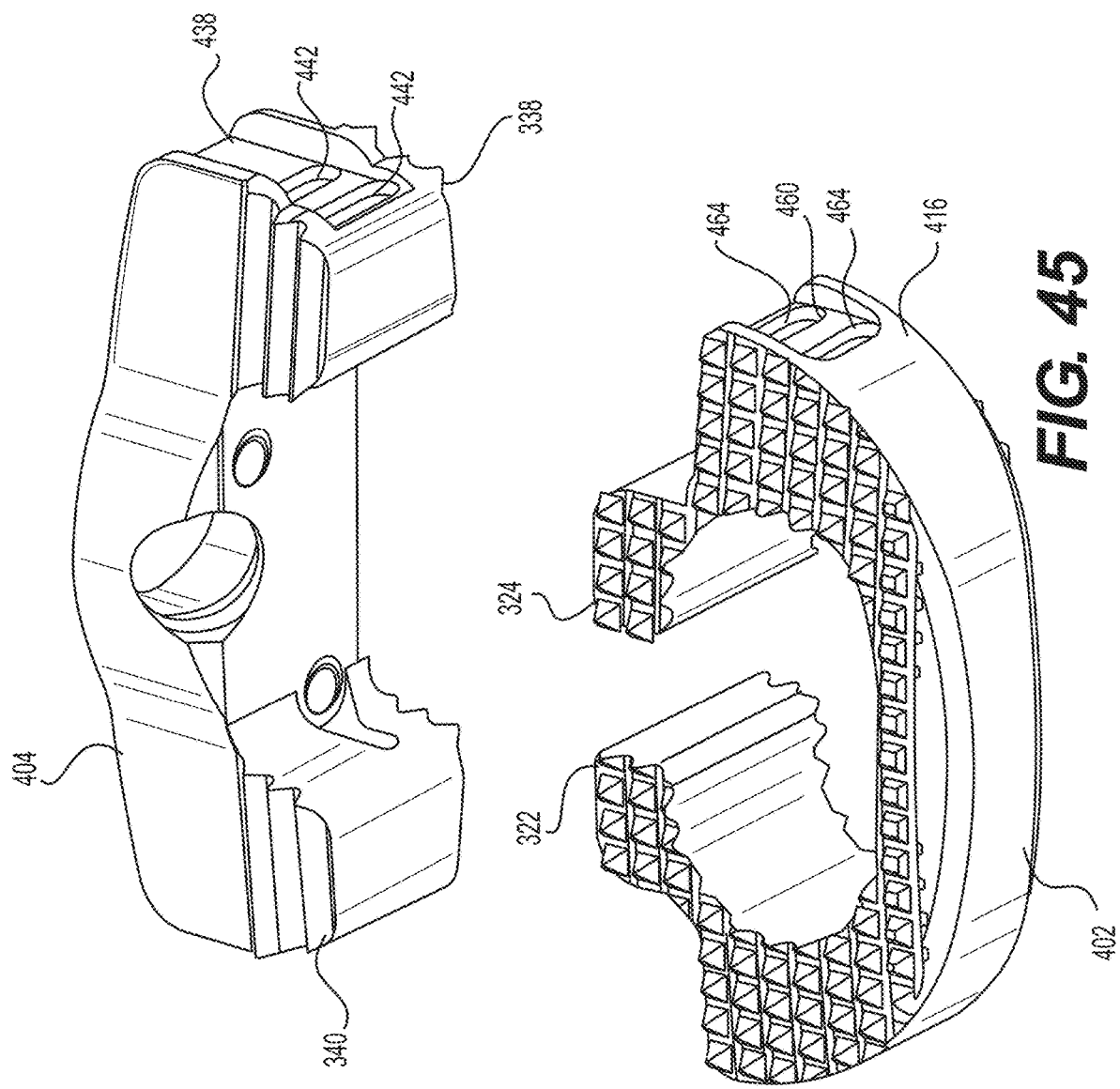
FIG. 45 is an exploded anterior perspective view of the assembly shown in FIG. 42.
Figure 46:
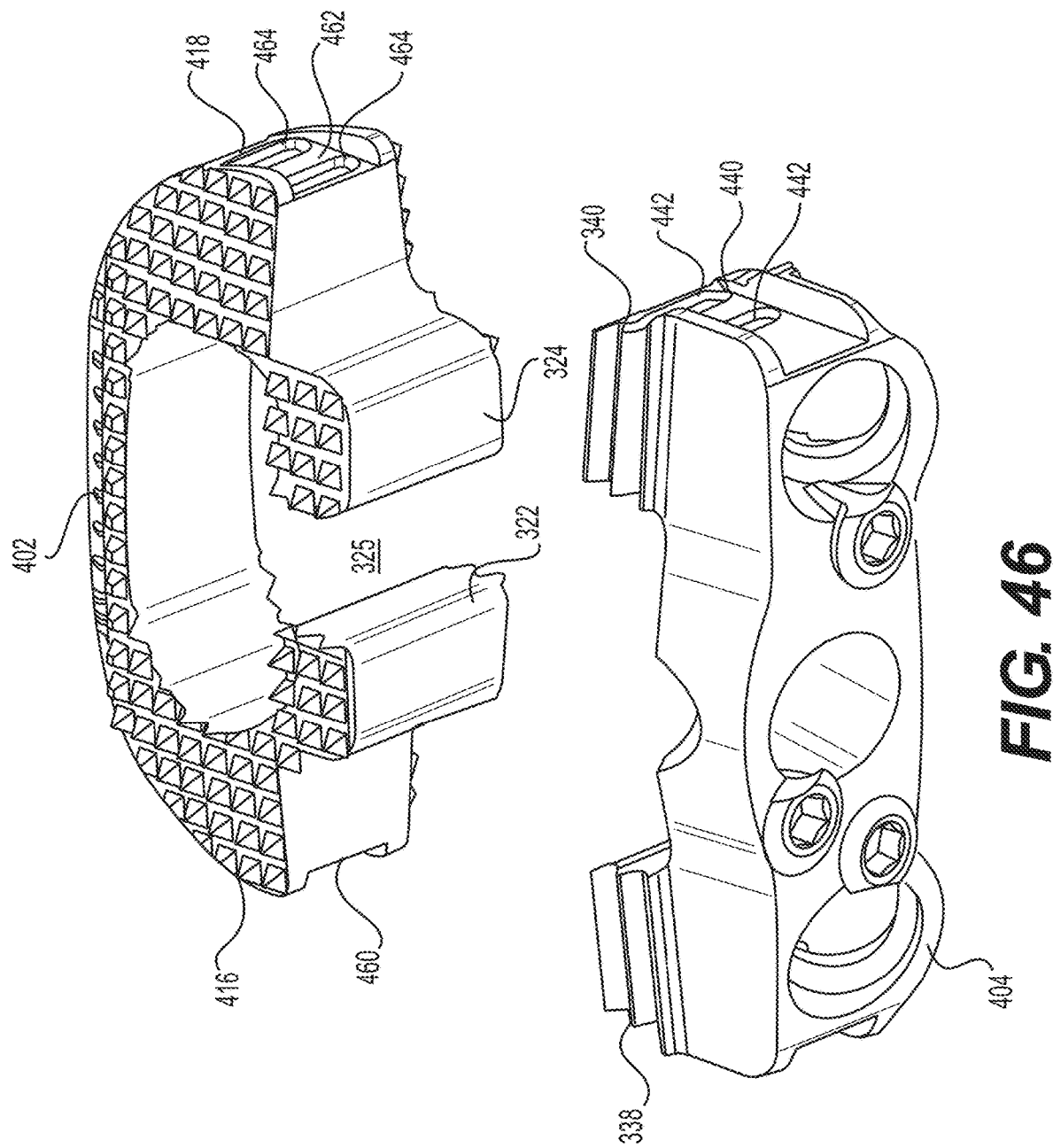
FIG. 46 is an exploded posterior perspective view of the assembly shown in FIG. 42.

Referring to FIGS. 42-47, spacer 402 is similar to spacer 302, but, instead of holes 260, 262 for insertion of insertion tool 306, lateral sides 416, 418 include a recess 460, 462, respectively. Recesses 460, 462 extend anteriorly from indentations 317, 319 toward anterior face 456. Each recess 460, 462 includes a plurality of superior-to-inferior extending slots 464. FIGS. 45 and 46 show two slots 464 in each recess 460, 462, although those skilled in the art will recognize that more or less than two slots 464 can be provided.

Additionally, fingers 338, 340 on plate 404 each include a recess 438, 440, respectively that extend in an anterior-to-posterior direction along the length of each respective finger 338, 340. Each recess 438, 440 includes a plurality of superior-to-inferior extending slots 464. FIGS. 45 and 46 show two slots 442 in each recess 438, 440, although those skilled in the art will recognize that more or less than two slots 442 can be provided.

Other aspects of spacer 402 and plate 404 are similar, if not identical, to corresponding aspects of spacer 302 and plate 304 as discussed above. Those aspects are identified with element numbers corresponding to spacer 302 and plate 304 with respect to spacer 402 and plate 404, respectively.

Insertion tool 406 is shown in FIGS. 47-52. Insertion tool 406 includes a distal end 470 having a first distal finger 472 and a second distal finger 474 that extends generally parallel to first distal finger 474. A gap between fingers 472, 474 forms a generally U-shaped cavity 476 that is sized to accept plate 404 therein, as shown in FIGS. 47 and 48. First distal finger 472 includes a plurality of protrusions 478 that fit into recess 460 and slots 464 on spacer 402 and recess 438 and slots 442 on plate 404. Similarly, second distal finger 474 includes a plurality of protrusions 480 that fit into recess 462 and slots 464 on spacer 402 and recess 440 and slots 442 on plate 404.

A proximal end (not shown) of insertion tool 406 can include a pivot connection such that the opening of insertion tool 406 at the proximal end splays first distal finger 472 away from second distal finger 474 to release spacer 402 and plate 404 so that spacer 402 and plate 404 are separated components.

Figure 52:
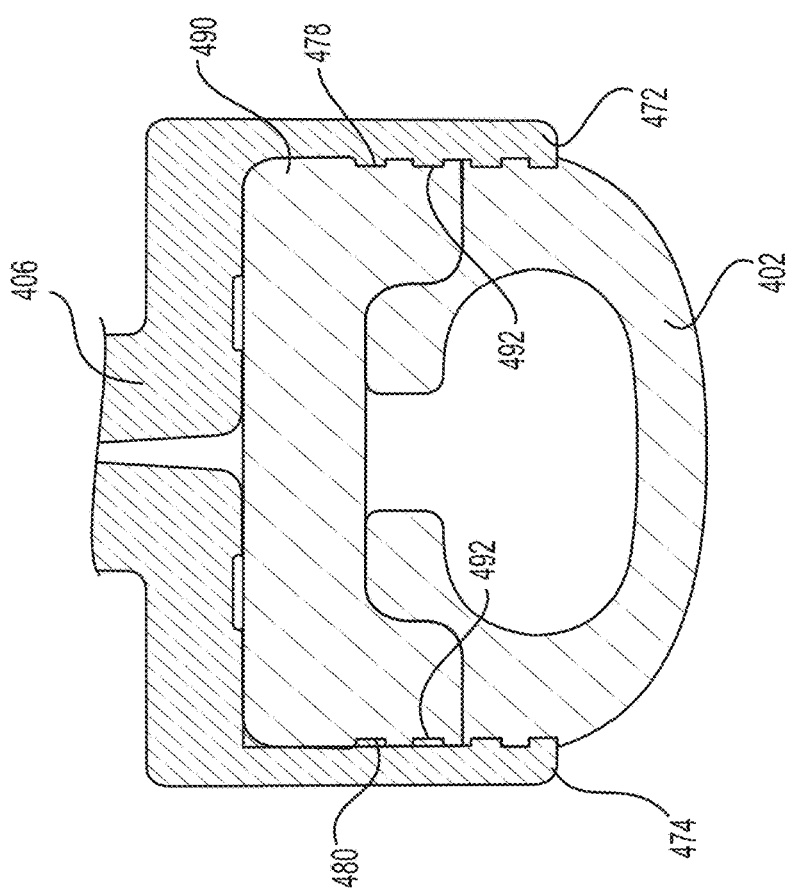
FIG. 52 is a perspective view of the spacer block, spacer, and insertion tool of FIG. 51.
Figure 51:
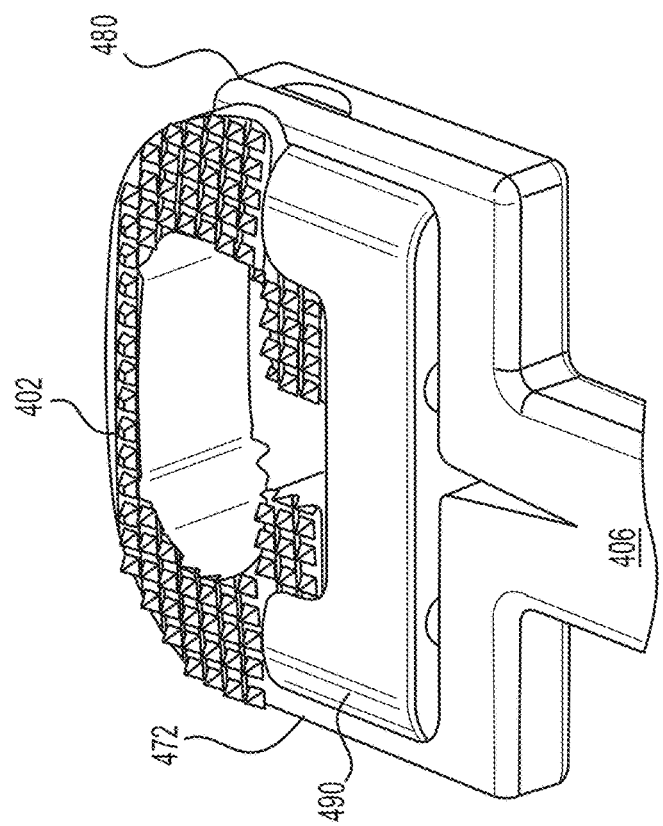
FIG. 51 is a top plan view, in section, of a spacer block and the spacer and insertion tool of FIG. 49.
Figure 53:
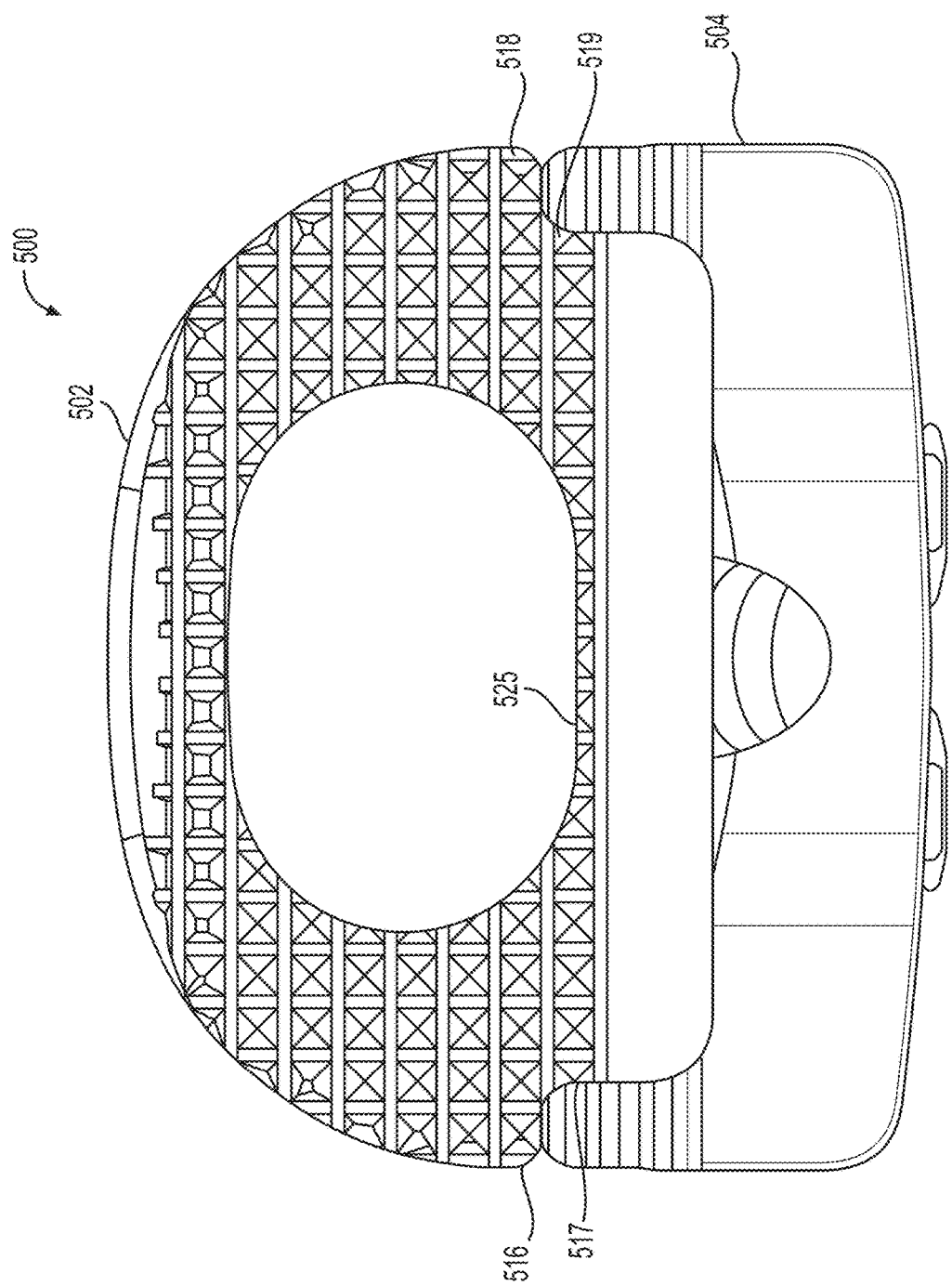
FIG. 53 is a top plan view of a spacer and plate assembly according to a fifth exemplary embodiment.
Figure 54:
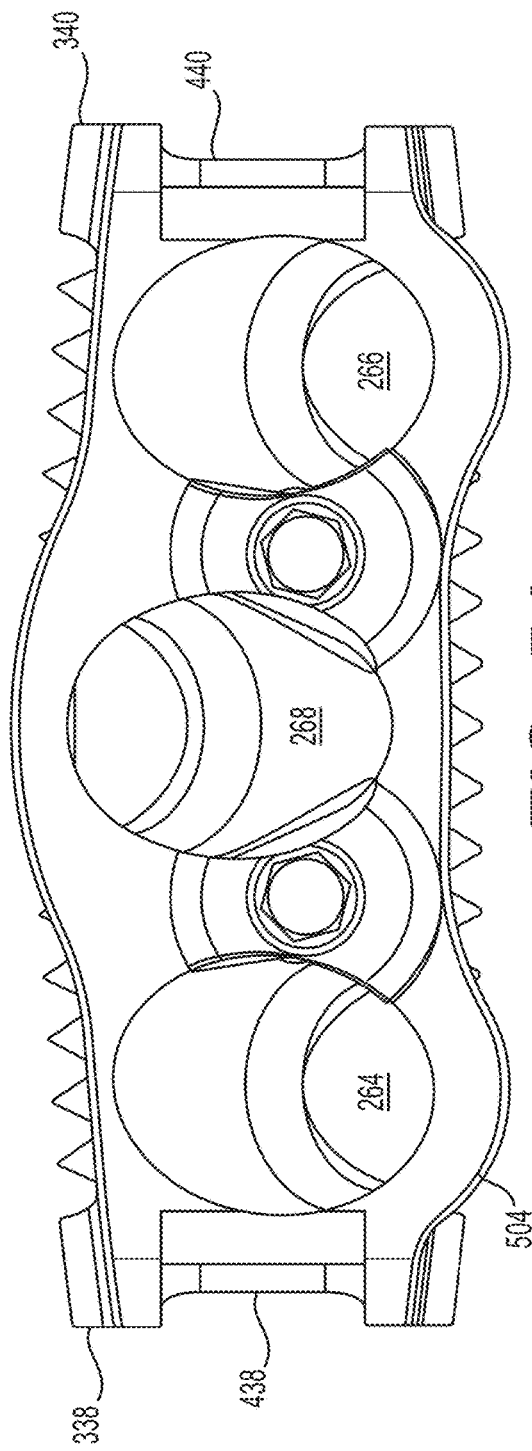
FIG. 54 is a posterior elevational view of the assembly shown in FIG. 53.
Figure 55:
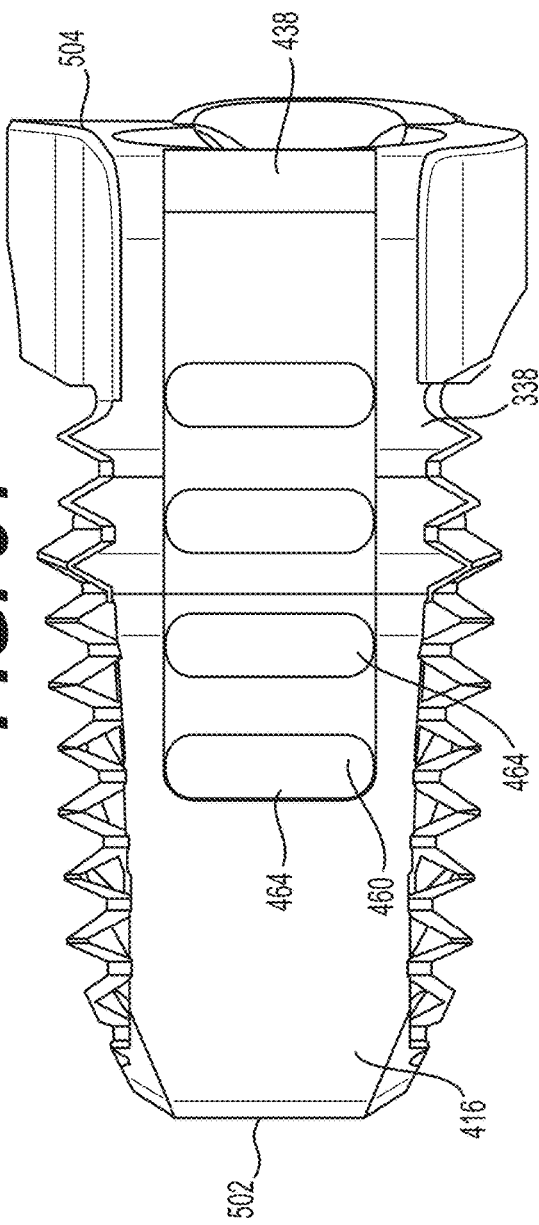
FIG. 55 is a left lateral side elevational view of the assembly shown in FIG. 53.
Figure 56:
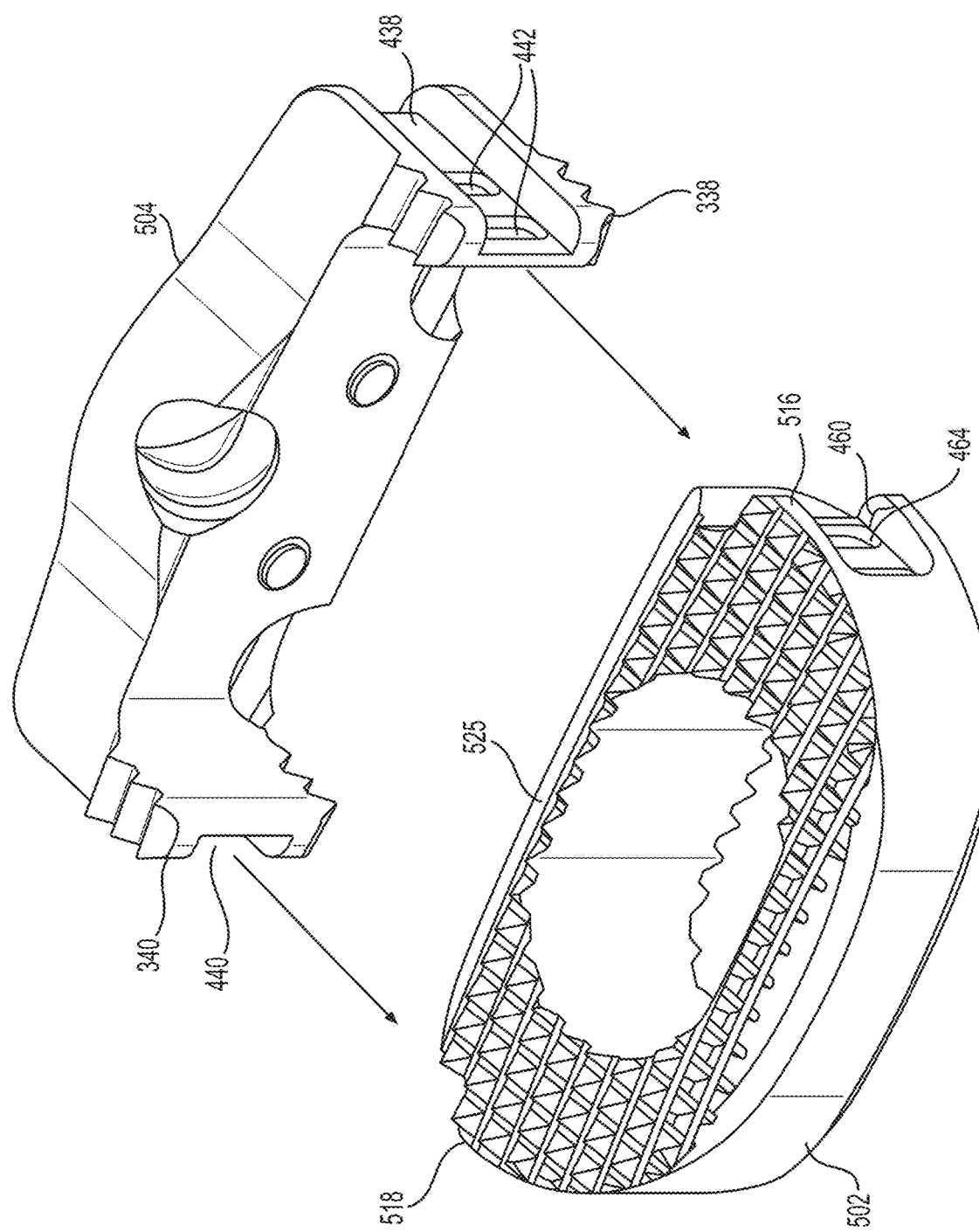
FIG. 56 is an exploded anterior perspective view of the assembly shown in FIG. 53.
Figure 57:
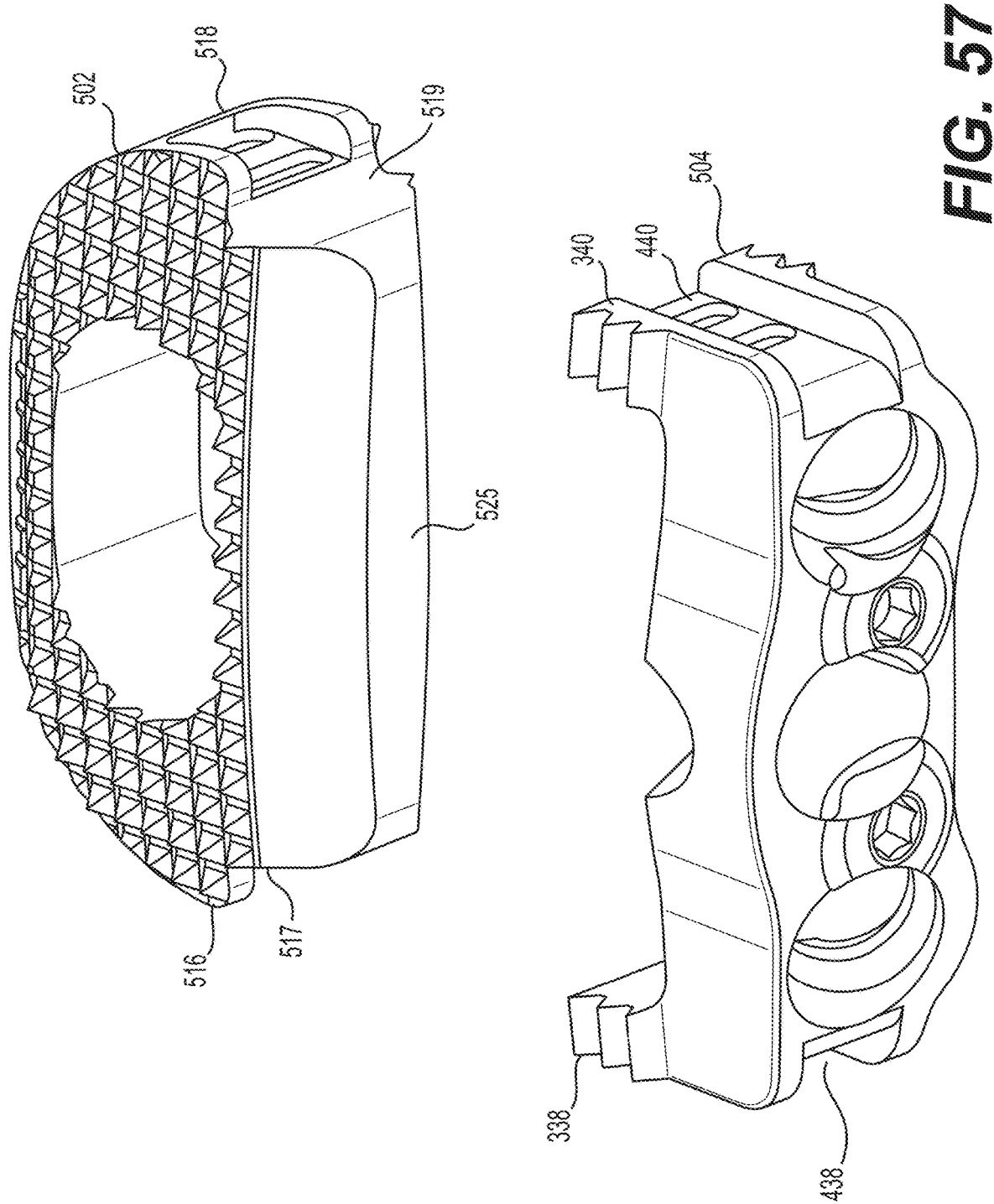
FIG. 57 is an exploded posterior perspective view of the assembly shown in FIG. 53.

Referring to FIGS. 51 and 52, spacer block 490 includes slots 492 that receive protrusions 478, 480 on insertion tool 406. Other aspects of spacer block 490 are similar, if not identical, to corresponding aspects of spacer block 390 as discussed above.

An alternative embodiment of an intervertebral spacer and plate assembly 500 ("assembly 500") is shown in FIGS. 53-63. In an exemplary embodiment, assembly 500 can be used for lumbar repair, although those skilled in the art will recognize that assembly 500 can be sized for thoracic or cervical repair as well.

Figure 58:
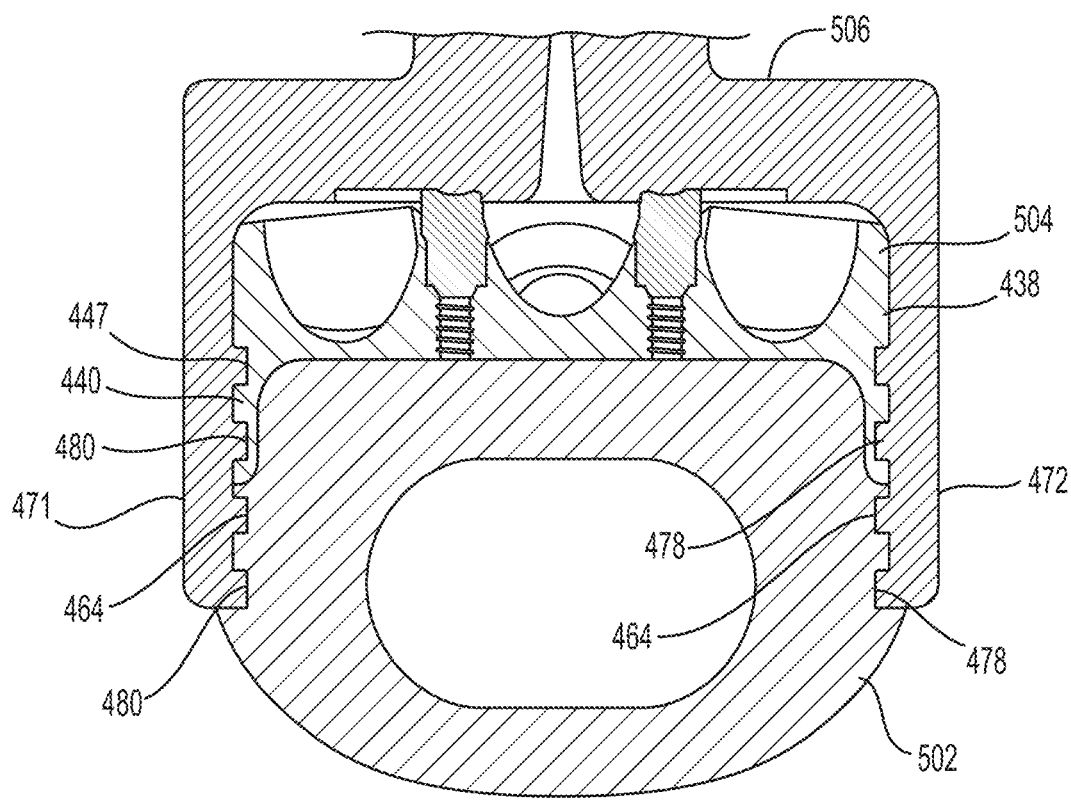
FIG. 58 is a top plan view, in section, of the assembly of FIG. 53 attached to an insertion tool for inserting the assembly of FIG. 53.
Figure 59:
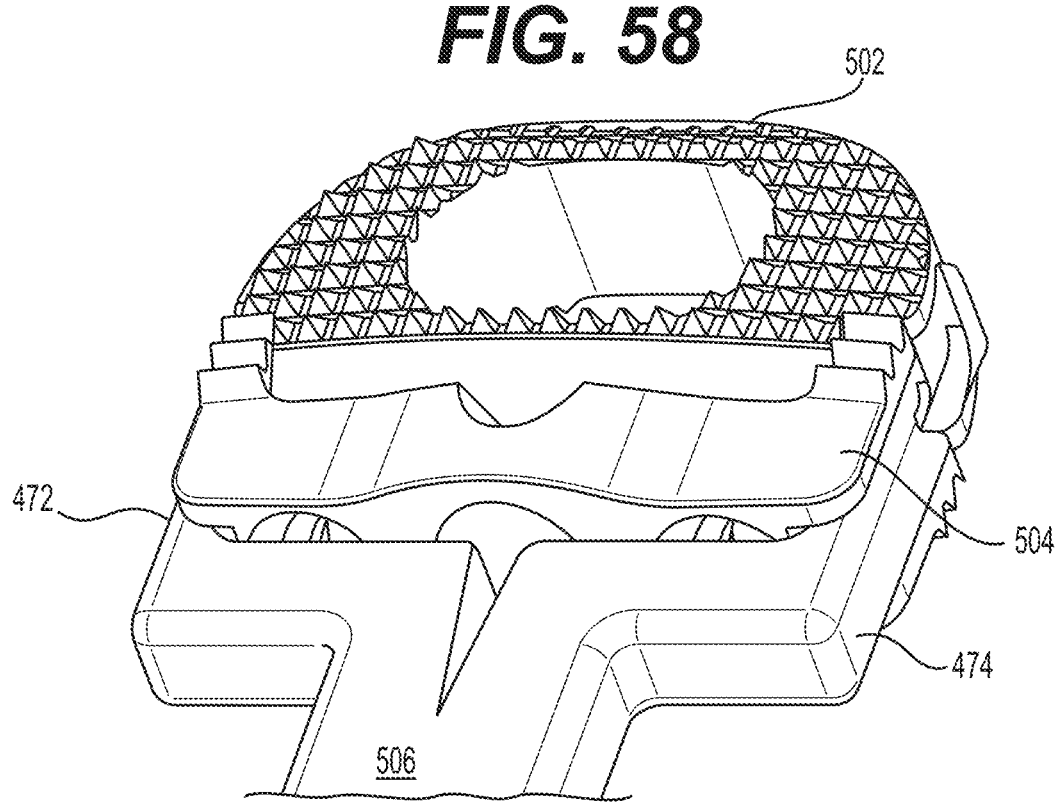
FIG. 59 is a perspective view of the assembly and insertion tool of FIG. 58.
Figure 60:
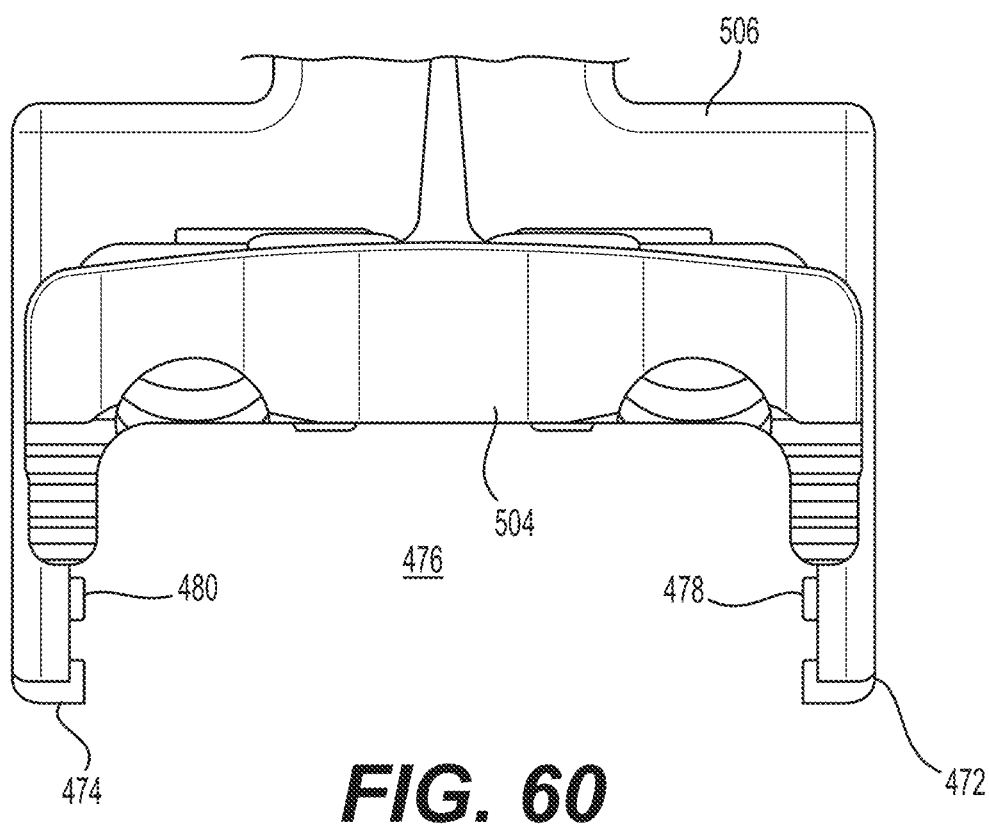
FIG. 60 is a top plan view, in section, of the plate of FIG. 53 and the insertion tool for inserting the plate.
Figure 61:
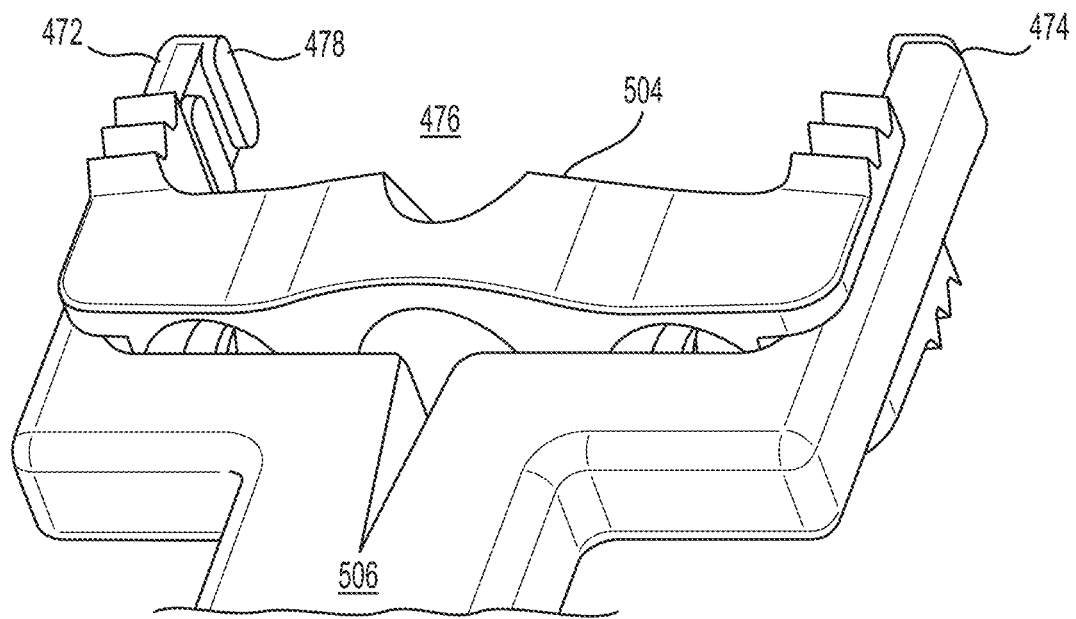
FIG. 61 is a perspective view of the plate and insertion tool of FIG. 60.

Assembly 500 is formed from two separate components, an intervertebral spacer 502 ("spacer 502") and a plate 504 ("plate 504"). In some embodiments, spacer 502 and plate 504 are not connected to each other, but are instead each separately coupled to an insertion tool 506, as shown in FIGS. 58 and 59.

Assembly 500 is similar to assembly 400 except that, instead of having gap 325 between two medially directed ends 324, 326, spacer 502 has a posterior portion 525 that extends fully between lateral sides 516, 518. Lateral sides 516, 518 include indentations 517, 519 that do not extend medially as far as indentations 317, 319 respectively, formed in spacer 402, as discussed above.

Figure 62:
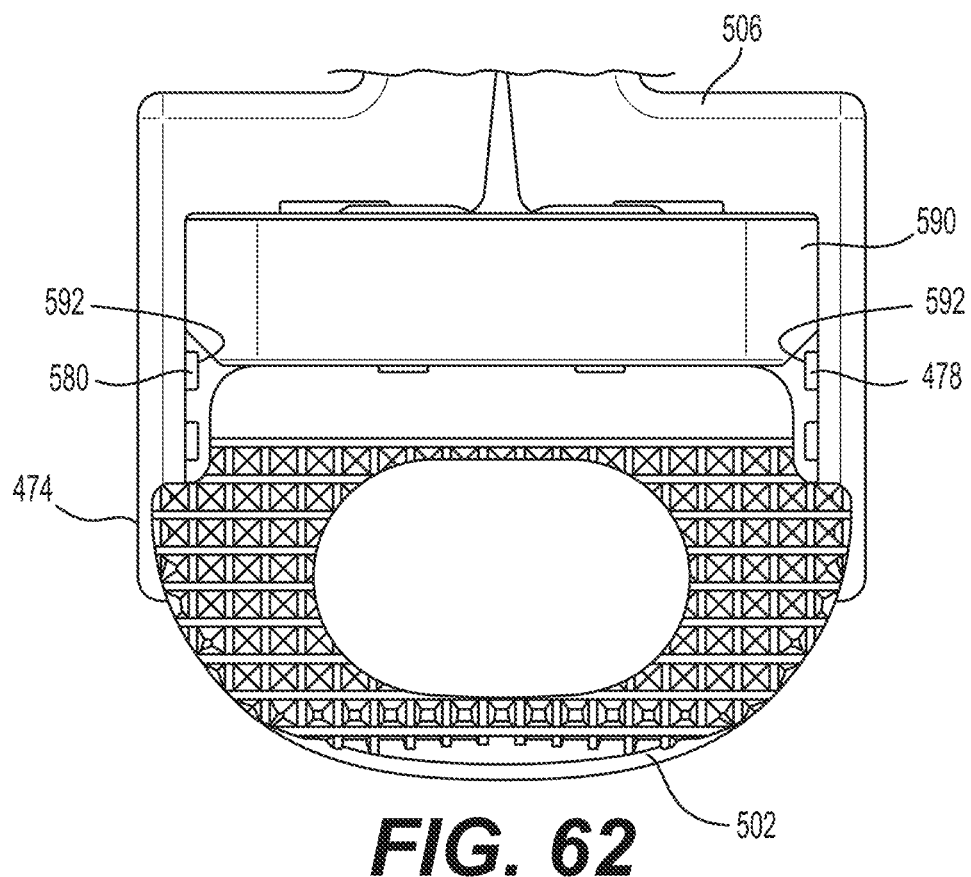
FIG. 62 is a top plan view, in section, of a spacer block and the spacer and insertion tool of FIG. 59.
Figure 63:
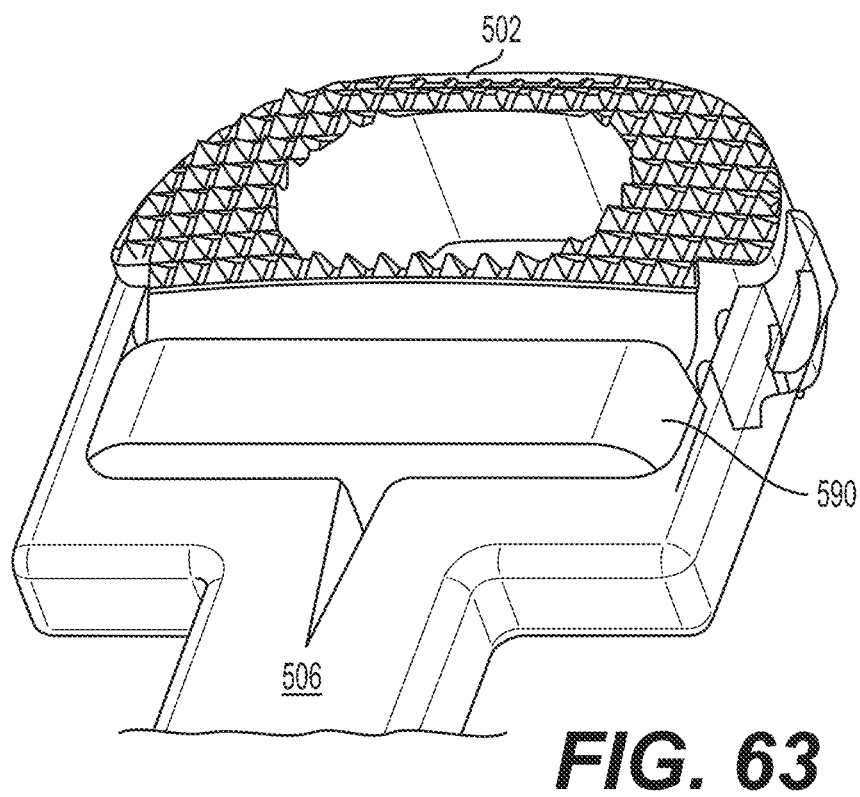
FIG. 63 is a perspective view of the spacer block, spacer, and insertion tool of FIG. 62.
Figure 64:
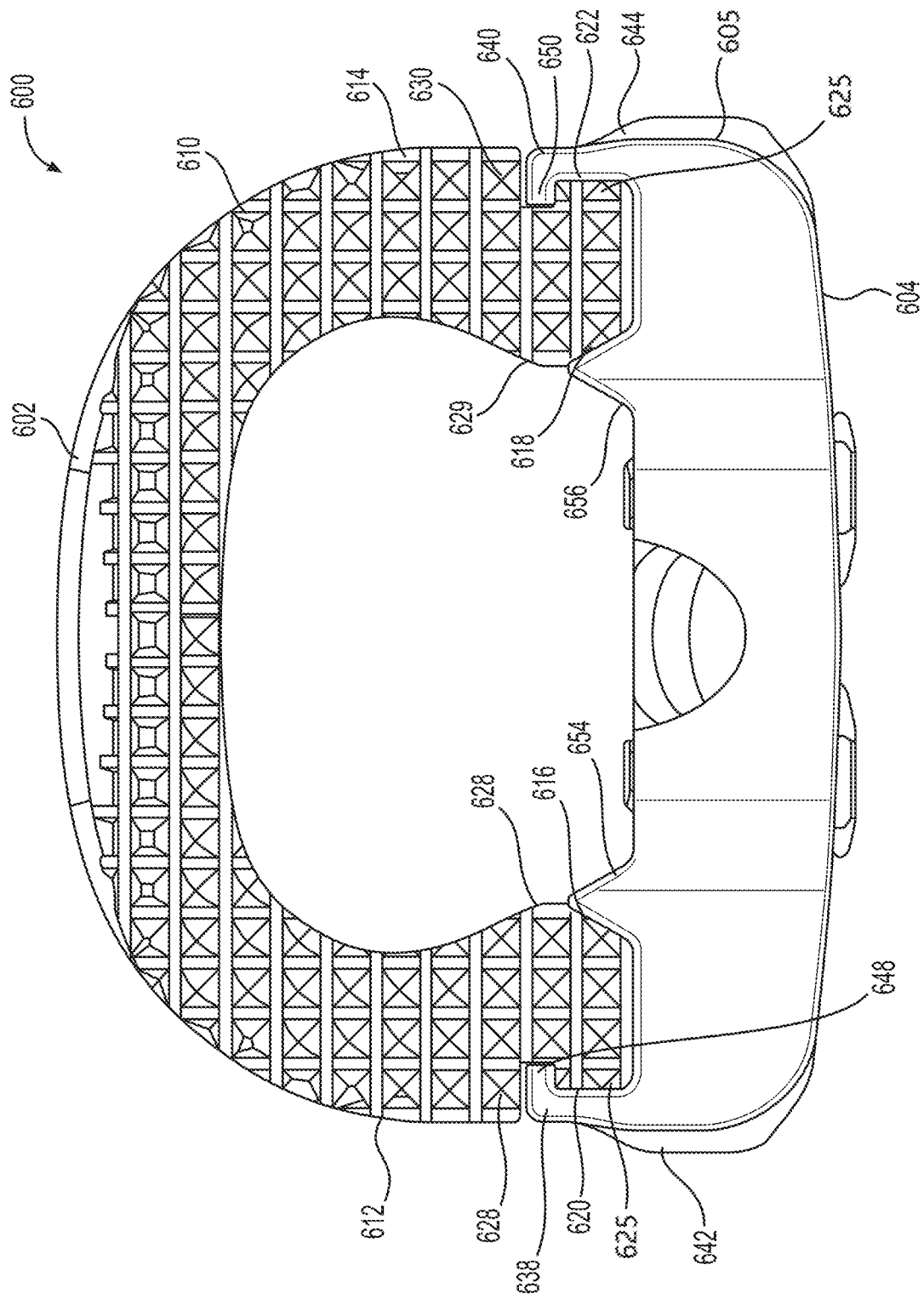
FIG. 64 is a top plan view of a spacer and plate assembly according to a sixth exemplary embodiment.

Additionally, referring to FIGS. 62 and 63, a spacer block 590 includes slots 592 that receive protrusions 478, 480 on an insertion tool 4506.

An alternative embodiment of an intervertebral spacer and plate assembly 600 ("assembly 600") is shown in FIGS. 64-67. In an exemplary embodiment, assembly 600 can be used for lumbar repair, although those skilled in the art will recognize that assembly 600 can be sized for thoracic or cervical repair as well.

Figure 65:
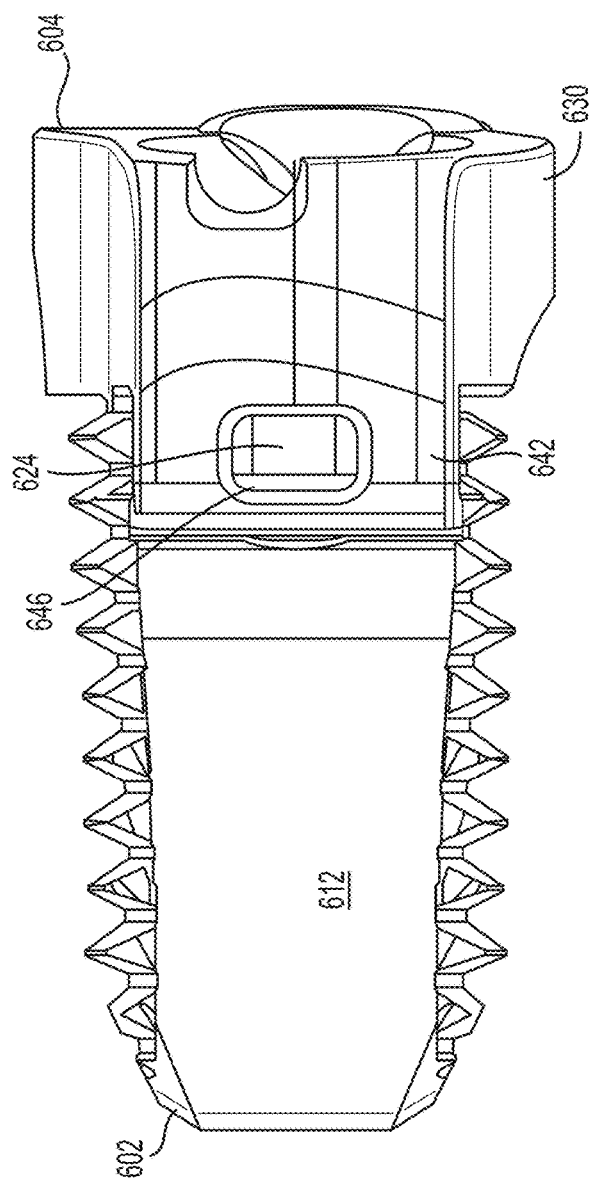
FIG. 65 is a left lateral side elevational view of the assembly shown in FIG. 64.

Assembly 600 is formed from two separate components, an intervertebral spacer 602 ("spacer 602") and a plate 604 ("plate 604"). Plate 704 is shown in detail in FIGS. 75-78. Plate 602 has a body 610 having a generally arcuate shape, with generally parallel lateral sides 612, 614. A posterior portion 616, 618, respectively, of each lateral side 612, 614 includes an anterior-to-posterior recess 620, 622, respectively. Each recess 620, 622 includes a laterally projecting protrusion 624 having sloped superior and inferior sides (only one protrusion 624 is shown in FIG. 65). Each recess 620, 622 is in communication with a slot 628, 630, respectively that each extends medially. A medial portion 628, 629 of each lateral side 612, 614, respectively, include an oblique cutout 616, 618.

Plate 604 includes a body 630 having a generally laterally elongate shape, with generally parallel lateral sides 642, 644. Fingers 638, 640 extend from lateral sides 642, 644, respectively. Fingers 638, 640 are sized to fit into recesses 620, 622, respectively, in spacer 602. As shown in FIG. 65, finger 638 includes a cutout 646 formed therein. Although not shown, finger 640 includes a corresponding cutout. An anterior end of each finger 638, 640 includes a medially extending prong 648, 650 that fits into a slot 628, 630, respectively. An anterior face 652 of body 630 also includes two spaced apart tangs 654, 656.

Figure 66:
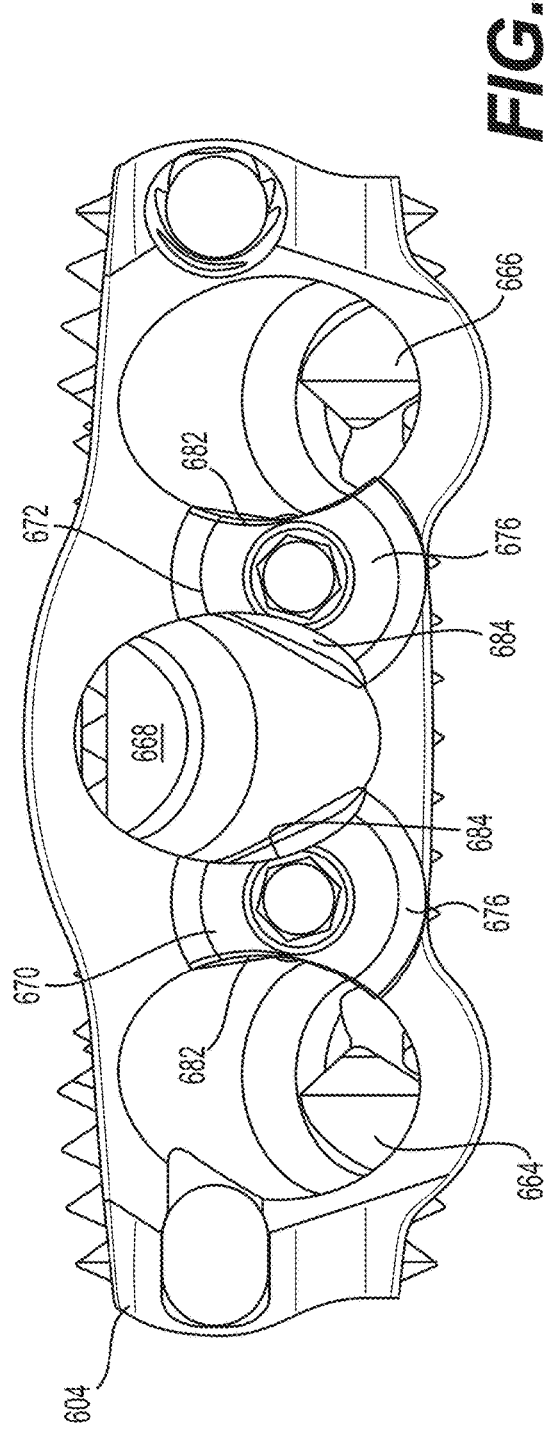
FIG. 66 is a posterior elevational view of the assembly shown in FIG. 64.
Figure 67:
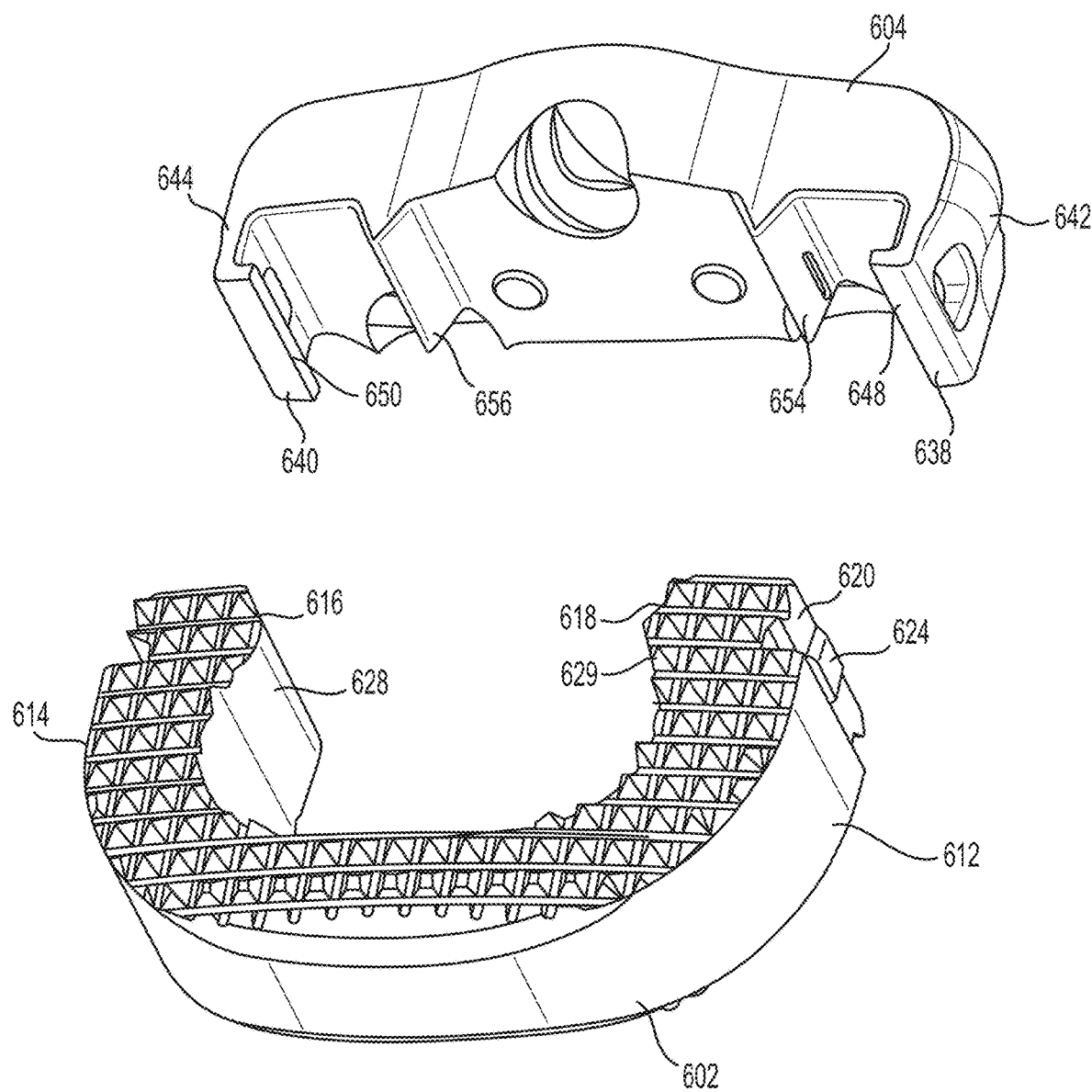
FIG. 67 is an exploded anterior perspective view of the assembly shown in FIG. 64.
Figures 68, 69, 70:
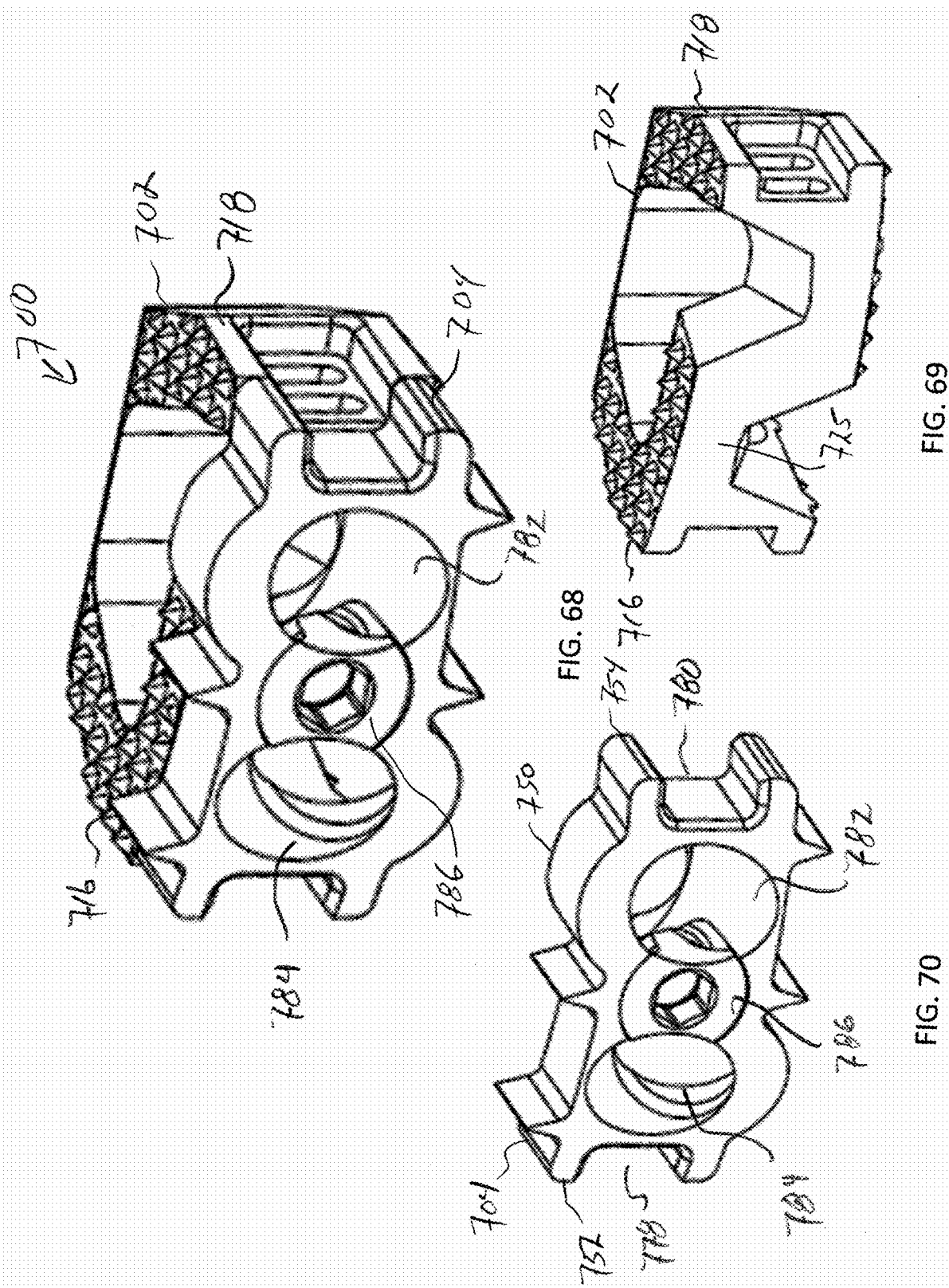
FIG. 68 is a perspective view of a spacer and plate assembly according to a seventh exemplary embodiment.
FIG. 69 is a perspective view of a spacer used with the assembly shown in FIG. 68.
FIG. 70 is a perspective view of a plate used with the assembly shown in FIG. 68.

Referring to FIG. 66, through-holes 664, 666, 668 are provided in plate 604 and are sized to allow a securing screw (not shown) to be inserted therethrough to secure plate 604 to each of a superior vertebra (not shown) and an inferior vertebra (not shown), between which spacer 602 is being inserted. Through-holes 664, 666 each extends in a superior-to-inferior direction so that their respective screw each engages and secures to the inferior vertebra, while through-hole 668 extends in an inferior-to-superior direction so that its screw engages and secures the superior vertebra.

Locking screws 670, 672 are each is disposed between respective through-holes 664, 666, 668. Each locking screw 670, 672 has a head 676 with a pair of arcuate cutouts 682, 684 that are sized to allow the securing screws discussed above to be inserted into through-holes 664, 666, 668. During insertion of assembly 600, locking screws 664, 666, 668 are in a configuration relative to plate 604 as shown in FIG. 66. After the securing screws secure plate 604 to the superior and inferior vertebra, locking screws 670, 672 are rotated, for example, about 90 degrees, so that heads 676, 678 each extends over its adjacent securing screws, preventing the securing screws from inadvertently backing out. In some embodiments, the locking screws 670, 672 (upon rotation) can abut a side of the securing screws to prevent inadvertent backing out.

Assembly 600 is fitted together by aligning fingers 638, 640 and prongs 648, 650 on plate 604 with recesses 620, 622 and slots 628, 630, respectively, on spacer 602, which also aligns lateral sides of tangs 654, 656 with cutout 616, 618, respectively. Plate 604 is slid down into spacer 602, locking fingers 638, 640 and prongs 648, 650 into recesses 620, 622 and slots 628, 630, respectively.

Additionally, protrusion 624 slides into cutout 646. Tangs 654, 656 engage cutouts 616, 618, respectively, stabilizing plate 604 with respect to spacer 602.

Assembly 600 is inserted between adjacent vertebrae as a unit, and, unlike other embodiments of the present invention, remain as a unit after implantation.

Another alternative embodiment of an intervertebral spacer and plate assembly 700 ("assembly 700") is shown in FIGS. 68-82. In an exemplary embodiment, assembly 700 can be used for cervical repair, although those skilled in the art will recognize that assembly 400 can be sized for thoracic or lumbar repair as well.

Assembly 700 is formed from two separate components, an intervertebral spacer 702 ("spacer 702") and a plate 704 ("plate 704"). In some embodiments, spacer 702 and plate 704 are not connected to each other, but are instead each separately coupled to an insertion tool similar to insertion tool 406, shown in FIGS. 47 and 48.

Figure 72:
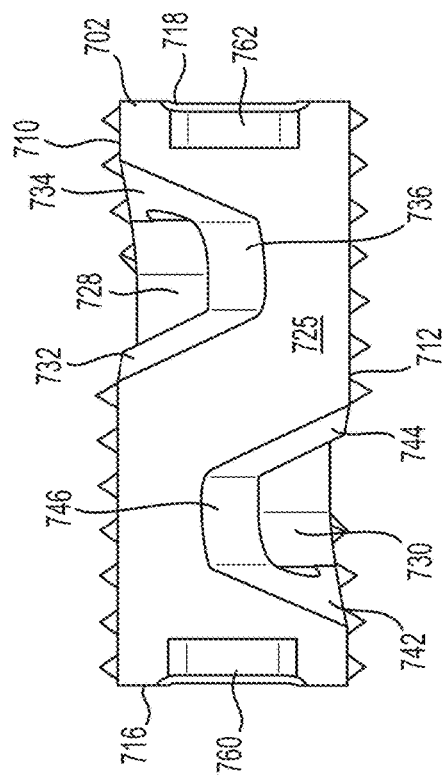
FIG. 72 is an anterior elevational view of the spacer shown in FIG. 69.
Figure 74:
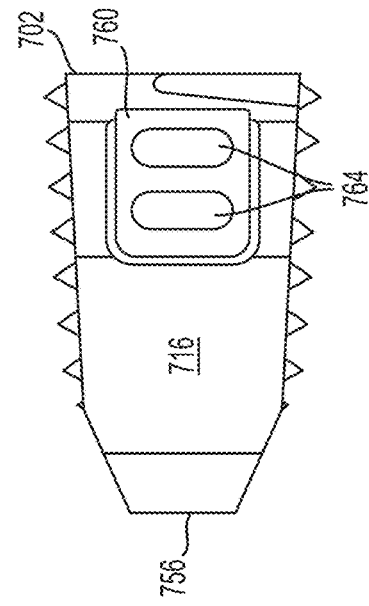
FIG. 74 is a left side elevational view of the spacer shown in FIG. 69.
Figure 71:
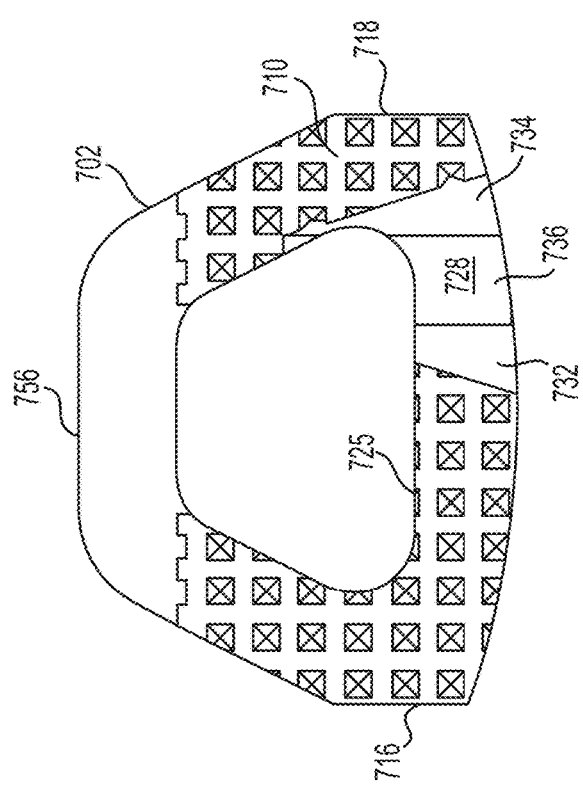
FIG. 71 is a top plan view of the spacer shown in FIG. 69.
Figure 73:
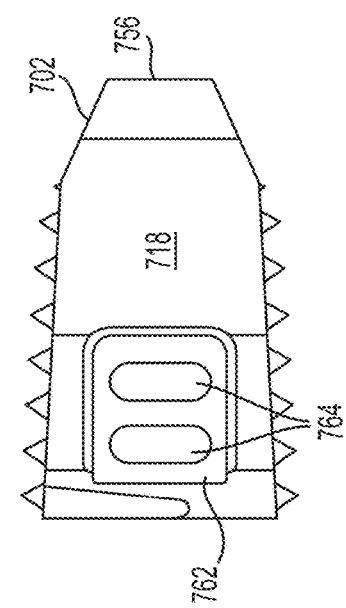
FIG. 73 is a right side elevational view of the spacer shown in FIG. 69.
Figure 76:
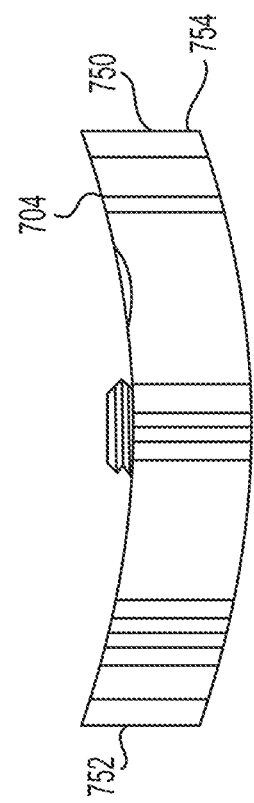
FIG. 76 is a top plan view of the plate shown in FIG. 70.
Figure 78:
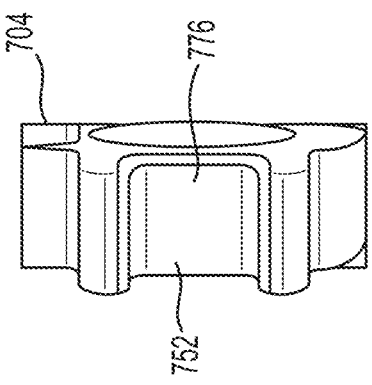
FIG. 78 is a left side elevational view of the spacer shown in FIG. 70.
Figure 75:
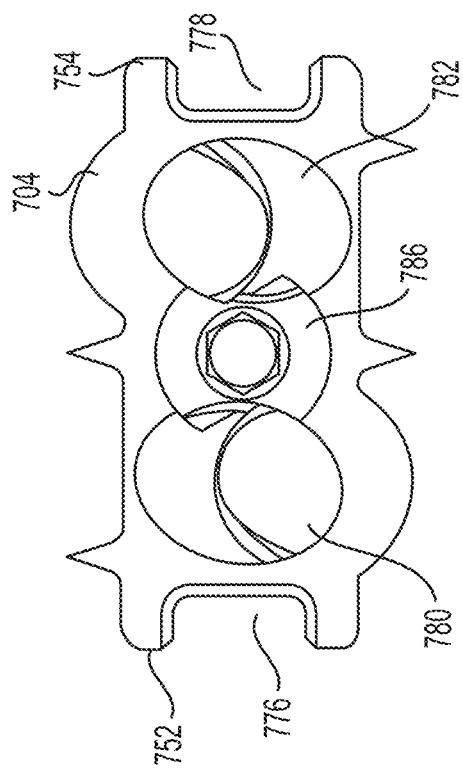
FIG. 75 is an anterior elevational view of the plate shown in FIG. 70.
Figure 77:
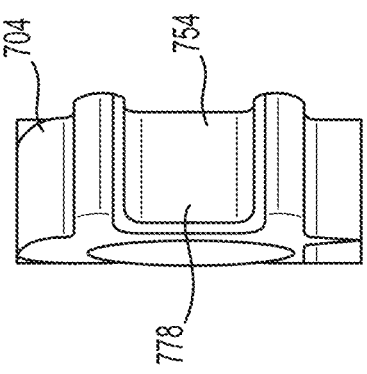
FIG. 77 is a right side elevational view of the plate shown in FIG. 70.
Figure 79:
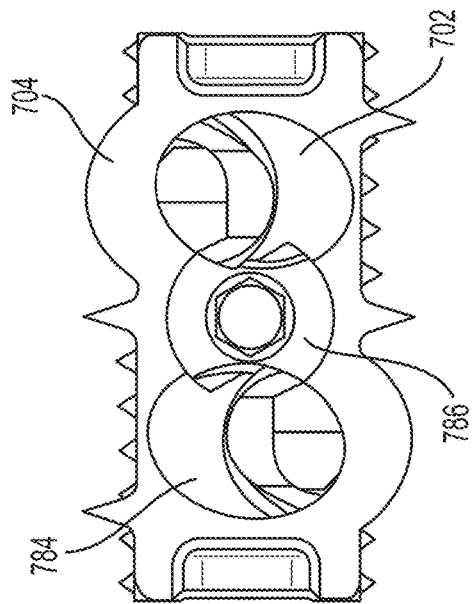
FIG. 79 is a top plan view of the assembly shown in FIG. 68.
Figure 80:
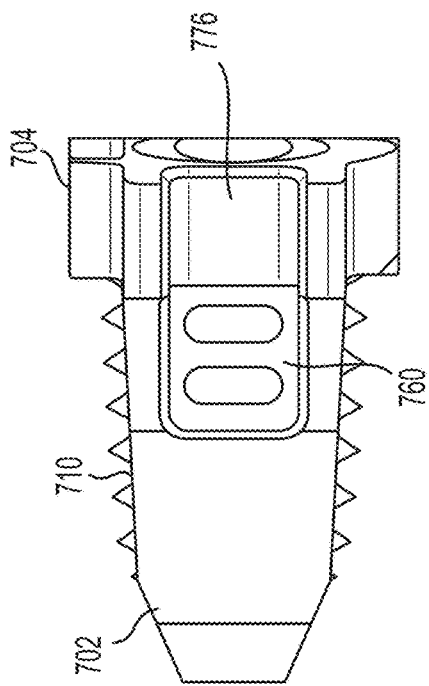
FIG. 80 is an anterior elevational view of the assembly shown in FIG. 68.

Referring to FIGS. 72-74, spacer 702 is similar to spacer 402, but, instead of having gap 325 between two medially directed ends 324, 326, spacer 702 has a posterior portion 725 that extends fully between lateral sides 716, 718. Recesses 760, 762 extend anteriorly from posterior portion 725 toward anterior face 756. Each recess 760, 762 includes a plurality of superior-to-inferior extending slots 764. FIGS. 73 and 74 show two slots 764 in each recess 760, 762, respectively, although those skilled in the art will recognize that more or less than two slots 764 can be provided.

Posterior portion 725 includes cutouts 728, 730 to allow securing screws (not shown) to extend therethrough to secure plate 704 to adjacent vertebrae (not shown). When viewed from a posterior-to-anterior direction, a first cutout 728 is formed in a superior surface 710 and is defined by side walls 732, 734 and a bottom wall 736. As shown in FIG. 72, side walls 732, 734 and bottom wall 736 extend at oblique angles relative to each other, although those skilled in the art will recognize that side walls 732, 734 can extend orthogonally to bottom wall 736.

Similarly, a second cutout 738 is formed in an inferior surface 712 and is defined by side walls 742, 744 and a top wall 746. As shown in FIG. 72, side walls 742, 744 and top wall 746 extend at oblique angles relative to each other, although those skilled in the art will recognize that side walls 742, 744 can extend orthogonally to top wall 746.

Plate 704 is shown in detail in FIGS. 75-78. Plate 704 has a body 750 having a generally arcuate shape, with generally parallel lateral sides 752, 754. Each lateral side 752, 754 includes an anterior-to-posterior recess 776, 778, respectively. Each recess 776, 778 is in communication with a slot 760, 762 in spacer 702.

Plate 704 also includes through-openings 782, 784 for securing screws (not shown) that are used to secure plate 704 to adjacent vertebrae (not shown). A locking screw 786 can be rotated, for example, about 90 degrees after the securing screws have been inserted to keep the securing screws from backing out after insertion. When plate 704 is aligned with spacer 702 as shown in FIGS. 79-82, through-opening 782 is aligned with first cutout 728 in spacer 702 and through-opening 784 is aligned with second cutout 730 in spacer 702 so that the securing screws can pass over or under spacer 702 and into their respective vertebrae.

Figure 81:
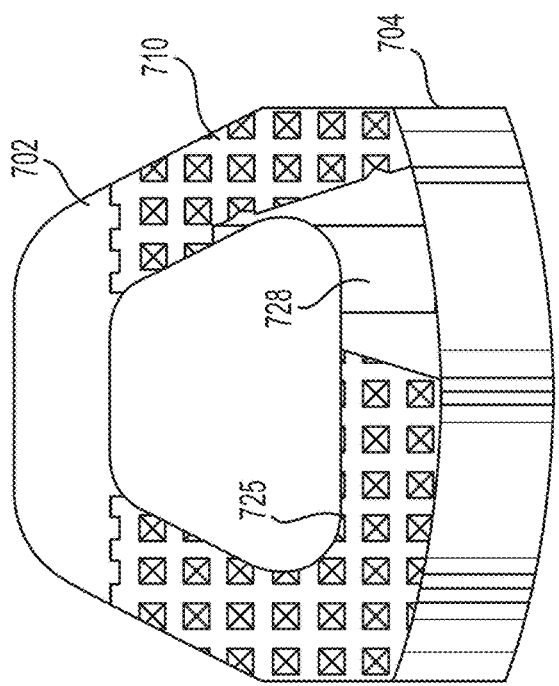
FIG. 81 is a right side elevational view of the assembly shown in FIG. 68.
Figure 82:
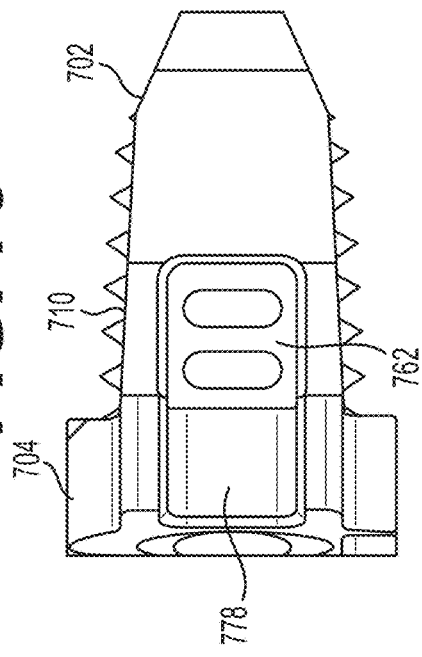
FIG. 82 is a left side elevational view of the assembly shown in FIG. 68.

Also, as shown in FIGS. 81 and 82, when plate 704 is aligned with spacer 702 for insertion, recess 776 is aligned with recess 760 and recess 778 is aligned with recess 762 so that an insertion tool, similar to insertion tool 406, can extend through plate 704 and grip spacer 702 for insertion.

The insertion procedure for assembly 700 can be similar to that as is described above for assembly 400. However, instead of insertion tool 406 having protrusions that engage plate 704, such protrusions can be omitted and assembly 700 can rely on friction between plate 704 and insertion tool 406, as well as between implant 702 and insertion tool 406.

An alternative embodiment of an intervertebral spacer and plate assembly 800 ("assembly 800") is shown in FIGS. 83-98. In an exemplary embodiment, assembly 800 can be used for cervical repair, although those skilled in the art will recognize that assembly 800 can be sized for thoracic or lumbar repair as well.

Assembly 800 is formed from two separate components, an intervertebral spacer 802 ("spacer 802") and a plate 804 ("plate 804"). In some embodiments, spacer 802 and plate 804 are not connected to each other, but instead merely engage each other.

Referring to FIGS. 84 and 86-89, spacer 802 includes a body 808 having a superior surface 810 and an opposing inferior surface 812. Each of superior surface 810 and inferior surface 812 can have a plurality of fixation elements 814 extending outwardly therefrom. While fixation elements 814 are shown as being generally pyramidal in shape, those skilled in the art will recognize that fixation elements 814 can be other shapes, such as ribbed, or other suitable shapes. Fixation elements 814 are used to bite into a grip each of adjacent vertebrae (not shown) between which spacer 802 is inserted.

As shown in FIG. 20, body 802 can have a generally oblong shape, with generally linear lateral sides 816, 818, connected to each other by an anterior portion 820 and a posterior portion 822, with a generally isosceles trapezoid interior space 823 defined therebetween that can optionally be filled with graft material.

Posterior portion 822 includes an arcuate face 824 that extends between lateral sides 816, 818. A rounded protrusion 826 extends posteriorly from posterior portion 822. A pair of insertion tool engagement holes 828, 829 are each located on opposing sides of protrusion 826. Holes 828, 829 can be threaded or unthreaded, and can be through-holes or blind holes. Holes 828, 829 are sized to accept arms of an insertion tool (not shown) for insertion of assembly 800.

Referring now to FIGS. 85 and 90-93, plate 804 includes a body 830 having an anterior surface 832 and an opposing posterior surface 834. Referring to FIGS. 90 and 91, plate 804 can have a generally "X" shape, with left and right superior arms 836, 838, respectively, and left and right inferior arms 840, 842, respectively. Superior arms 836, 838 include through-openings 844, 846 that are angled in a superior direction to allow screws (not shown) to be inserted therethrough to secure plate 804 to a superior vertebra (not shown). Similarly, inferior arms 840, 842 include through-openings 848, 850 that are angled in an inferior direction to allow securing screws (not shown) to be inserted therethrough to secure plate 804 to an inferior vertebra (not shown).

Referring to FIG. 90, locking screws 852, 854, 856, 858 are each disposed adjacent to a respective through-opening 844, 846, 848, 850. Each locking screw 852, 854, 856, 858 has a head 860 with an arcuate cutout 862, respectively, that is sized to allow the securing screws discussed above to be inserted into through-openings 844, 846, 848, 850. During insertion of assembly 800, locking screws 852, 854, 856, 858 are in a configuration relative to plate 804 as shown in FIG. 95. After the securing screws secure plate 804 to the superior and inferior vertebra, locking screws 852, 854, 856, 858 are rotated, for example, about 90 degrees, so that heads 860 each extends over its adjacent securing screws, preventing the securing screws from inadvertently backing out.

Plate 804 also includes a centrally located posterior recess 870. As shown in FIG. 90, recess 870 can be generally oblong in shape, although those skilled in the art will recognize that recess 870 can be other shapes. Recess 870 accepts a prong on an insertion device (not shown) for insertion of assembly 800.

Figure 98:
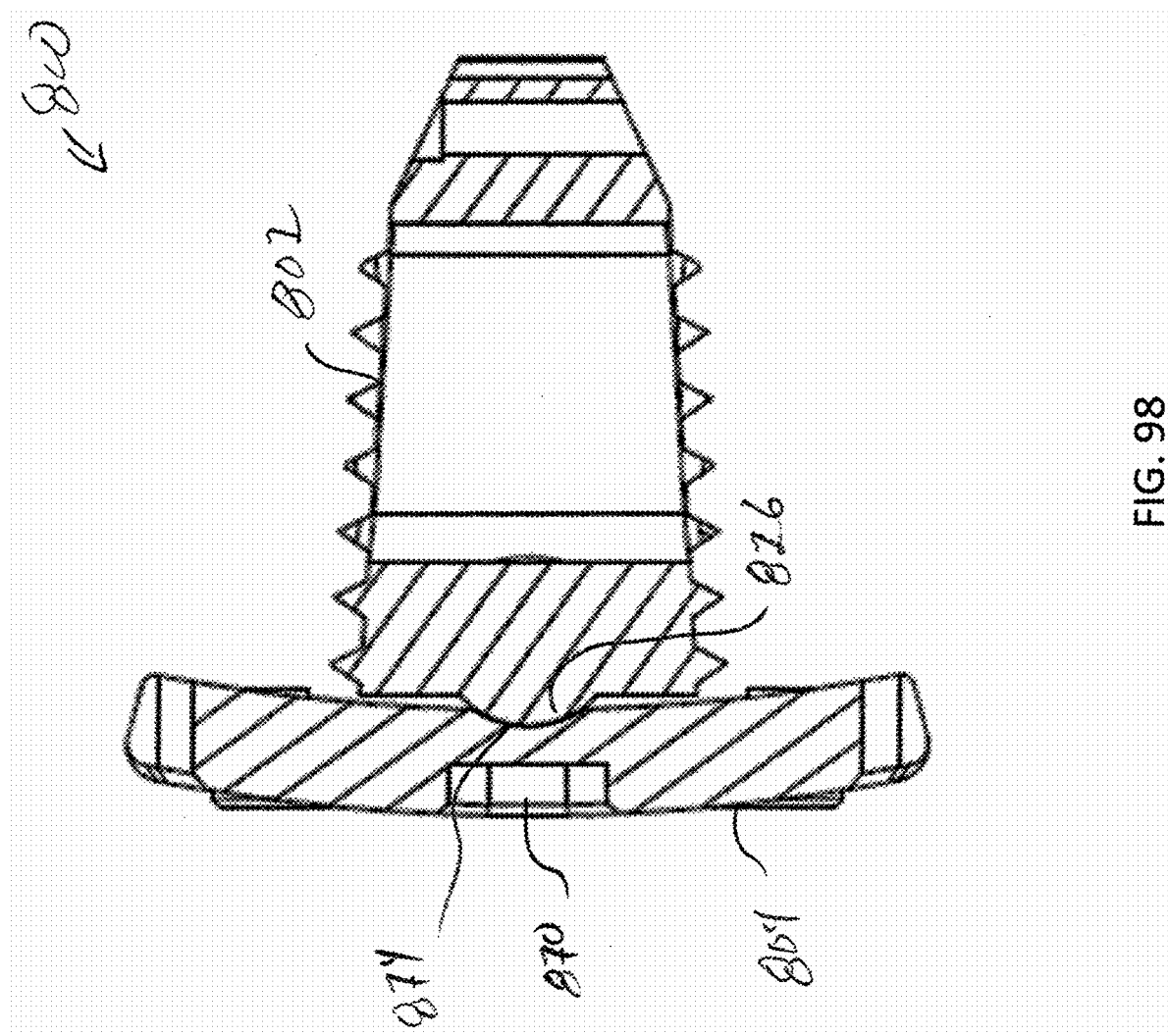
FIG. 98 is a side elevational view, in section, of the assembly shown in FIG. 94, taken along lines 98-98 of FIG. 94.
Figure 111:
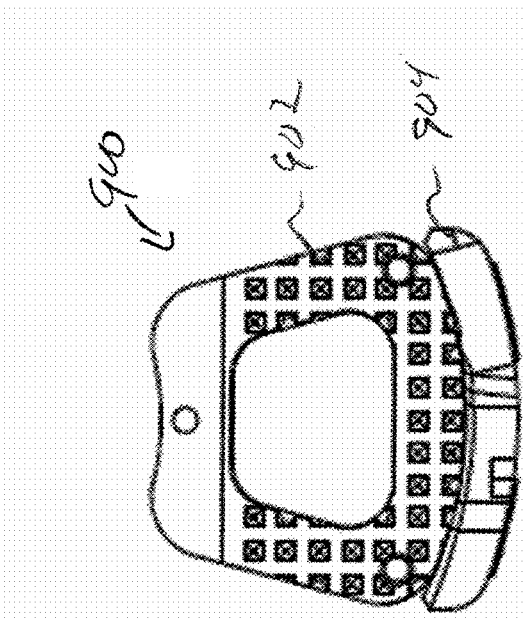
FIG. 111 is an anterior elevational view of the assembly shown in FIG. 99.
Figure 110:
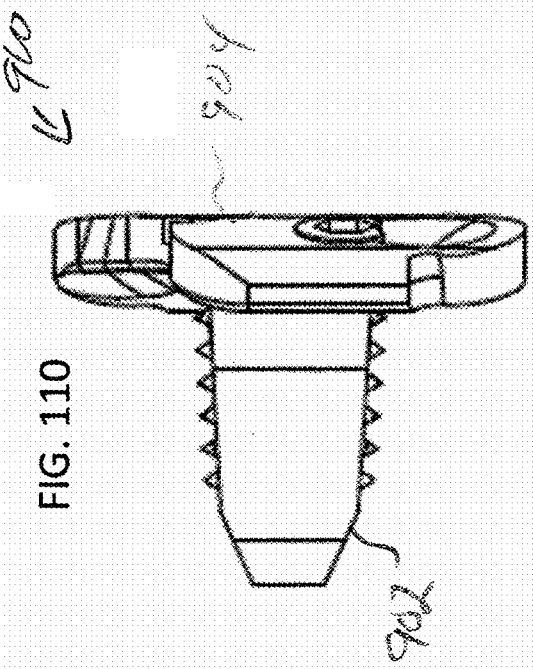
FIG. 110 is a top plan view of the assembly shown in FIG. 99.
Figure 112:
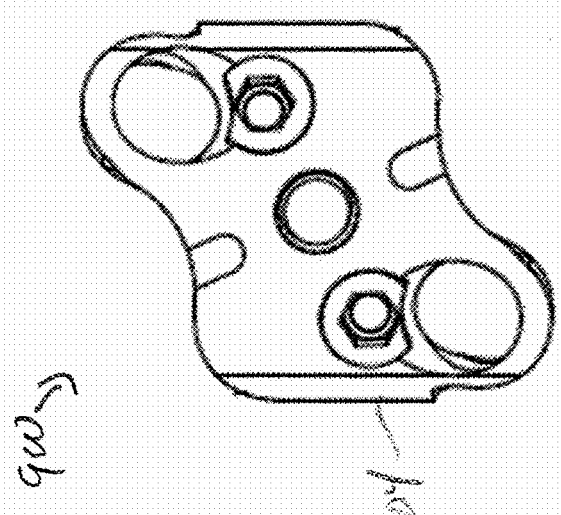
FIG. 112 is a right side elevational view of the assembly shown in FIG. 99.
Figure 113:
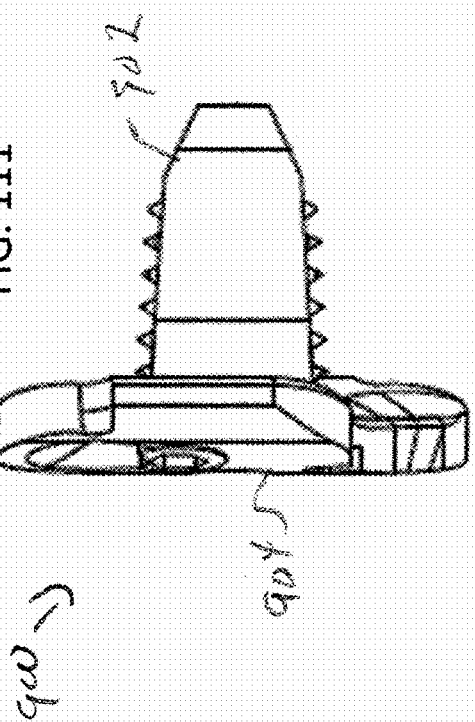
FIG. 113 is a left side elevational view of the assembly shown in FIG. 99.

Referring to FIG. 91, anterior surface 8732 of plate 804 includes a centrally located concave recess 874 that accepts protrusion 826, as shown in FIG. 98. Protrusion 826 rides within recess 874, forming an articulating joint that allows plate 804 to pivot relative to body 802, providing some flexibility for the patient after assembly 800 is implanted.

FIGS. 83 and 95-98 show assembly 800. While plate 804 is butted up against spacer 802 to form a coupled construct, plate 804 is not rigidly connected to spacer 802 so that spacer 802 and plate 804 remain separate, independent components throughout insertion and after insertion into the patient.

An alternative embodiment of an intervertebral spacer and plate assembly 900 ("assembly 900") is shown in FIGS. 99-113. In an exemplary embodiment, assembly 900 can be used for cervical repair, although those skilled in the art will recognize that assembly 900 can be sized for thoracic or lumbar repair as well.

Assembly 900 is formed from two separate components, an intervertebral spacer 902 and a plate 904. Spacer 902 and plate 904 are never connected to each other, but instead merely engage each other.

Referring to FIGS. 99 and 102-105, spacer 902 includes a body 908 having a superior surface 910 and an opposing inferior surface 912. Each of superior surface 910 and inferior surface 912 can have a plurality of fixation elements 914 extending outwardly therefrom. While fixation elements 914 are shown as being generally pyramidal in shape, those skilled in the art will recognize that fixation elements 914 can be other shapes, such as ribbed, or other suitable shapes. Fixation elements 914 are used to bite into a grip each of adjacent vertebrae (not shown) between which spacer 902 is inserted.

As shown in FIG. 103, body 902 can have a generally oblong shape, with generally linear lateral sides 916, 918, connected to each other by an anterior portion 920 and a posterior portion 922, with a generally isosceles trapezoid interior space 923 defined therebetween that can optionally be filled with graft material.

Posterior portion 922 includes an arcuate face 924 that extends between lateral sides 916, 918. A generally centrally located insertion tool engagement hole 928 extends through posterior portion 922. Hole 928 can be threaded, as shown in FIG. 100, or unthreaded. Hole 928 is sized to an insertion tool (not shown) for insertion of assembly 900.

A pair of plate engagement slots 931, 932 are each located on opposing sides of hole 928. Slots 931, 932 are blind holes and are generally rectangular in shape, with rounded corners. Slots 931, 932 are sized to accept posterior protrusions from plate 904, as is discussed below.

Referring now to FIGS. 101 and 106-109, plate 904 includes a body 930 having an anterior surface 933 and an opposing posterior surface 934. Referring to FIGS. 108 and 109 and 91 plate can have a generally "rhomboid" shape, with a right superior arm 936 and a left inferior arm 940. Superior arm 936 includes a through-opening 944 that is angled in a superior direction to allow a screw (not shown) to be inserted therethrough to secure plate 904 to a superior vertebra (not shown). Similarly, inferior arm 940 includes a through-opening 948 that is angled in an inferior direction to allow a securing screw (not shown) to be inserted therethrough to secure plate 904 to an inferior vertebra (not shown).

Referring to FIG. 108, locking screws 952, 954 are each disposed adjacent to a respective through-opening 944, 948. Each locking screw 952, 954 has a head 960 with an arcuate cutout 962, respectively, that is sized to allow the securing screws discussed above to be inserted into through-openings 944, 948. During insertion of assembly 900, locking screws 952, 954 are in a configuration relative to plate 904 as shown in FIG. 108. After the securing screws secure plate 904 to the superior and inferior vertebra, locking screws 952, 954 are rotated, for example, about 90 degrees, so that heads 960 each extends over its adjacent securing screws, preventing the securing screws from inadvertently backing out.

Plate 904 also includes a centrally located through-opening 970. As shown in FIG. 108, through-opening 970 can be generally circular in shape, although those skilled in the art will recognize that through-opening 970 can be other shapes. Through-opening 970 is unthreaded and allows an insertion device (not shown) to pass therethrough for engagement with hole 928 in spacer 902 for insertion of assembly 900.

Referring still to FIG. 108, a posterior surface 972 of plate 904 includes a pair of diametrically opposed slots 974, 976 that extend at an oblique angle away from through-opening 970. Slots 974, 976 accept a prong of an insertion instrument (not shown) during implantation of assembly 900, allowing the insertion instrument to be placed into slots 974, 976 so that plate 904 is held rigidly on the insertion instrument without being able to rotate.

Referring now to FIGS. 106, 107, and 109, an anterior surface 980 of plate 904 includes a pair of diametrically opposed protrusions 982, 984 that are sized and located to fit into plate engagement slots 931, 932. A posterior end of locking screws 952, 954 also extends outwardly from plate engagement slots 931, 932 as well.

FIGS. 99 and 110-113 show assembly 900. While plate 904 is butted up against spacer 902 to form a coupled construct, plate 904 is not connected to spacer 902 so that spacer 902 and plate 904 remain separate components throughout insertion and after insertion into the patient.

FIGS. 114-116 show an alternative plate 1004 that can be used with spacer 902 to form an assembly 1000. Plate 1004 has a generally rectangular shape with a centrally located through-opening 1070. As shown in FIG. 114, through-opening 1070 can be generally circular in shape, although those skilled in the art will recognize that through-opening 1070 can be other shapes. Through-opening 1070 is unthreaded and allows an insertion device (not shown) to pass therethrough for engagement with hole 928 in spacer 902 for insertion of assembly 1000.

Plate 1004 has left and right superior through-openings 1044, 1046 that are angled in a superior direction to allow screws (not shown) to be inserted therethrough to secure plate 1004 to a superior vertebra (not shown). Similarly, plate 1004 has left and right inferior through-openings 1048, 1050 that are angled in an inferior direction to allow securing screws (not shown) to be inserted therethrough to secure plate 1004 to an inferior vertebra (not shown).

Locking screws 1052, 1054, 1056, 1058 are each disposed adjacent to a respective through-opening 1044, 1046, 1048, 1050. Each locking screw 1052, 1054, 1056, 1058 has a head 1060 with an arcuate cutout 1062, respectively, that is sized to allow the securing screws discussed above to be inserted into through-openings 1044, 1046, 1048, 1050. During insertion of assembly 1000, locking screws 1052, 1054, 1056, 1058 are in a configuration relative to plate 1004 as shown in FIG. 114. After the securing screws secure plate 904 to the superior and inferior vertebra, locking screws 1052, 1054, 1056, 1058 are rotated, for example, about 90 degrees, so that heads 1060 each extends over its adjacent securing screws, preventing the securing screws from inadvertently backing out.

A posterior surface 1072 of plate 1004 also includes a pair of superior and inferior slots 1074, 1076 on opposing sides of through-opening 1070. Slots 1074, 1076 accept a prong of an insertion instrument (not shown) during implantation of assembly 1000, allowing the insertion instrument to be placed into slots 1074, 1076 so that plate 1004 is held rigidly on the insertion instrument without being able to rotate.

Figure 117:
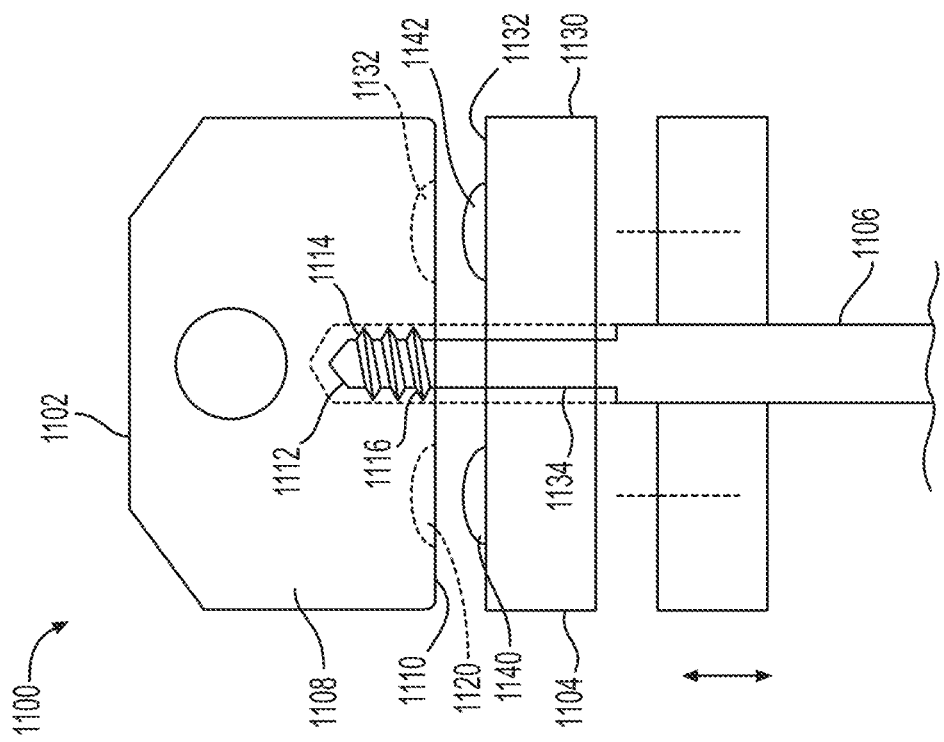

Referring now to FIG. 117, an alternative embodiment of an intervertebral spacer and plate assembly 1100 ("assembly 1100") is shown. Assembly 1100 includes a spacer 1102 and a plate 1104.

Plate 1102 has a body 1108 that includes a posterior surface 1110. Posterior surface 1110 includes a central through-opening 1112 that is sized to accept an insertion instrument 1106. Through-opening 1112 is threaded to match threads 1114 on a distal end 1116 of insertion instrument 1106. Posterior surface 1110 also includes a pair of concave recesses 1120, 1122, one on either side of through-opening 1112.

Plate 1104 has a body 1130 that includes an anterior surface 1132 for mating with posterior surface 1110 of spacer 1102. Body 1130 includes a through-opening 1134 that extends posteriorly-to-anteriorly through the center of body 1130. Through-opening 1134 has a larger diameter than through-opening 1112 in spacer 1102 to allow distal end 1116 of insertion instrument 1106 to pass therethrough.

Anterior surface 1132 of body 1130 also includes a pair of convex protrusions 1140, 1142, one on either side of through-opening 1134 that extend into recesses 1120, 1122, respectively, when plate 1104 is butted against spacer 1102, forming a solid construct.

Figure 118:
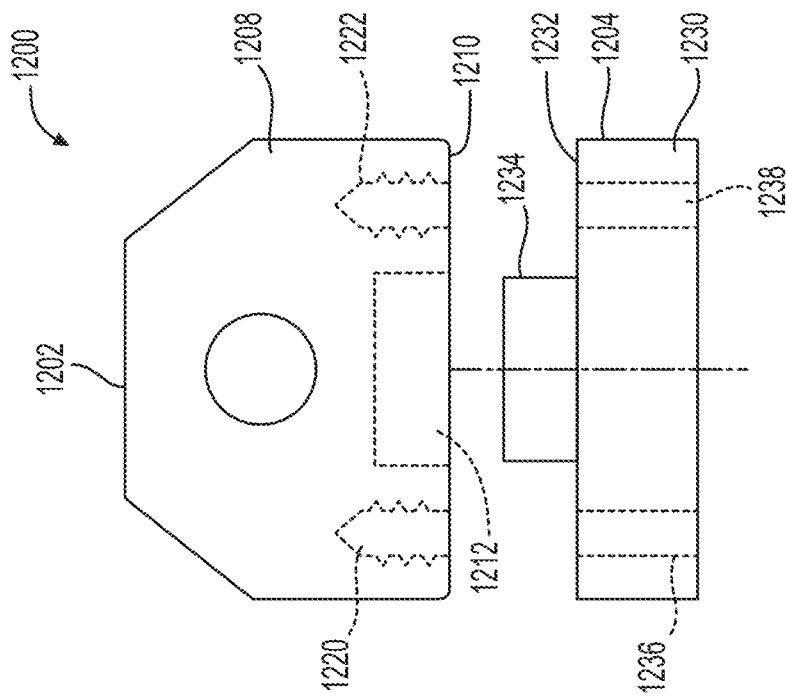

Referring now to FIG. 118, an alternative embodiment of an intervertebral spacer and plate assembly 1200 ("assembly 1200") is shown. Assembly 1200 includes a spacer 1202 and a plate 1204.

Plate 1202 has a body 1208 that includes a posterior surface 1210. Posterior surface 1210 includes a central recess 1212. Posterior surface 1210 also includes a pair of threaded recesses 1220, 1222, one on either side of central recess 1212.

Plate 1204 includes a body 1230 having an anterior surface 1232. A protrusion 1234 extends anteriorly from anterior surface 1232 and is sized to fit into central recess 1212. Body 1230 also includes a pair of lateral through-holes 1236, 1238 that extend through body 1230 and align with threaded recesses 1220, 1222 when protrusion 1234 is inserted into central recess 1212.

To insert assembly 1200 into a patient, an insertion instrument (not shown) having two prongs is inserted through through-holes 1236, 1238 in plate 1104 and threaded into threaded recesses 1220, 1222 in plate 1200. Assembly 1200 is inserted into plate 1204 is secured to a patient, then the insertion tool is unthreaded from threaded recesses 1220, 1222 and removed from assembly 1200.

Figure 119:
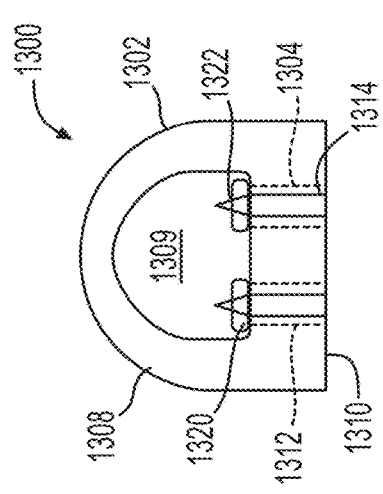

Referring now to FIG. 119, an alternative embodiment of an intervertebral spacer and plate assembly 1300 ("assembly 1300") is shown. Assembly 1300 includes a spacer 1302 and a plate 1304. Spacer 1302 includes a body 1308 having a central void 1309 formed therein. A posterior side 1310 of spacer 1302 includes a pair of through-passages 1312, 1314 into void 1309.

Plate 1304 includes a pair of fingers 1320, 1322, each of which extends into one of through-passages 1312, 1314 and into void 1309. When two prongs of an insertion device (not shown) are inserted into through-passages 1312, 1314, fingers 1320, 1322 splay open, temporarily securing plate 1304 to spacer 1302 for insertion. After insertion, when the insertion device is removed, fingers "un-splay" so that plate 1304 is no longer secured to spacer 1302 and spacer 1302 and plate 1304 are two separate entities.

Referring now to FIG. 119, an alternative embodiment of an intervertebral spacer and plate assembly 1300 ("assembly 1300") is shown. Assembly 1300 includes a spacer 1302 and a plate 1304. Spacer 1302 includes a body 1308 having a central void 1309 formed therein. A posterior side 1310 of spacer 1302 includes a pair of through-passages 1312, 1314 into void 1309.

Plate 1304 includes a pair of fingers 1320, 1322, each of which extends into one of through-passages 1312, 1314 and into void 1309. When two prongs of an insertion device (not shown) are inserted into through-passages 1312, 1314, fingers 1320, 1322 splay open, temporarily securing plate 1304 to spacer 1302 for insertion. After insertion, when the insertion device is removed, fingers "un-splay" so that plate 1304 is no longer secured to spacer 1302 and spacer 1302 and plate 1304 are two separate entities.

Figure 120:
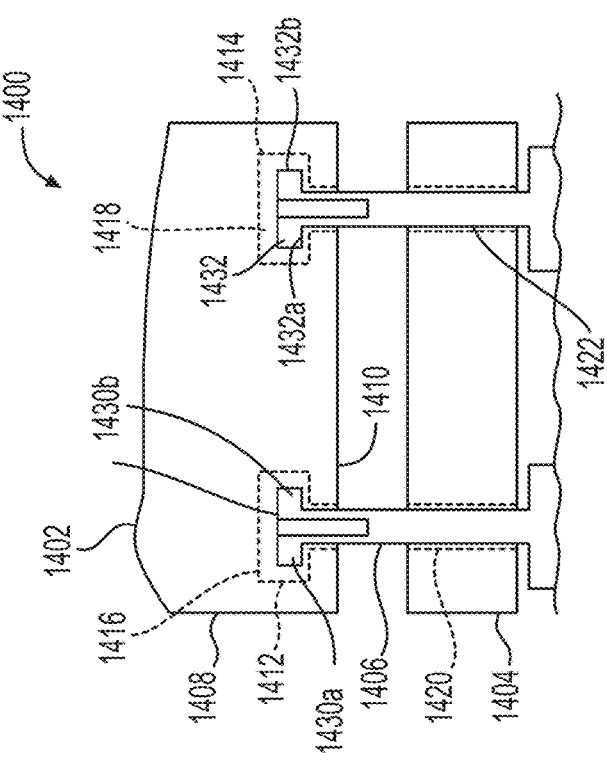

Referring now to FIG. 120, an alternative embodiment of an intervertebral spacer and plate assembly 1400 ("assembly 1400") is shown. Assembly 1400 includes a spacer 1402 and a plate 1404. Spacer 1402 includes a body 1408. A posterior side 1410 of spacer 1302 includes a pair of blind passages 1412, 1414 extending into body 1408. Each of blind passages 1412, 1414 widens to a receiving portion 1416, 1418, respectively, in a posterior-to-anterior direction.

Plate 1404 includes a pair of through-passages 1420, 1422 extending parallel to each other in a posterior-to-anterior direction such that, when plate 1404 is aligned with spacer 1402, passage 1420 aligns with passage 1412 and passage 1422 aligns with passage 1414.

An insertion device 1406 includes two parallel hollow prongs 1430, 1432. Each prong 1430, 1432 is split posteriorly into two half portions 1430a, 1430b and 1432a, 1432b, each portion 1430a, 1430b, 1432a, 1432b having a lip.

When prongs 1430, 1432 of insertion device 1406 are inserted through through-passages 1420, 1422 and into blind passages 1412, 1414, respectively, and rods (not shown) are inserted through prongs 1430, 1432, prong half portions 1430a, 1430b and 1432a, 1432b splay apart so that the lips on prongs 1430, 1432 splay open and are retained within receiving portions 1416, 1418, respectively, temporarily securing plate 1404 to spacer 1402 for insertion. After insertion, when the insertion device is removed, fingers "un-splay" so that plate 1404 is no longer secured to spacer 1402 and spacer 1402 and plate 1404 are two separate entities.

Figure 121:
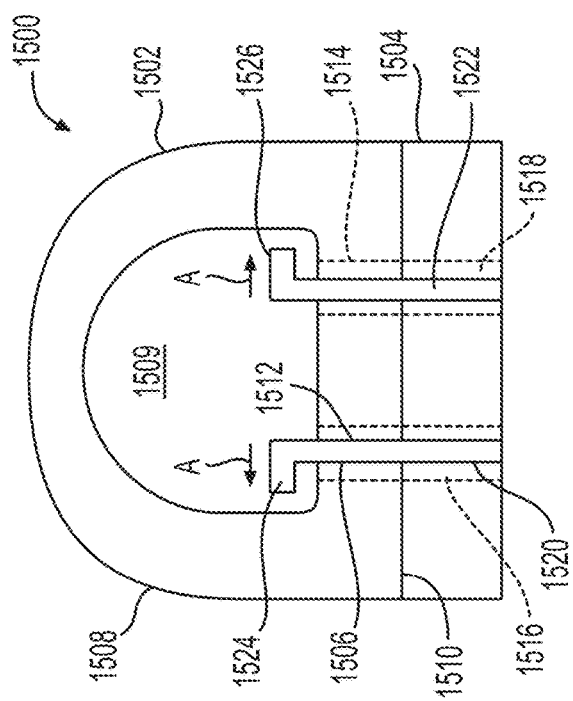

Referring now to FIG. 121, an alternative embodiment of an intervertebral spacer and plate assembly 1500 ("assembly 1500") is shown. Assembly 1500 includes a spacer 1502 and a plate 1504. Spacer 1502 includes a body 1508 having a central void 1509 formed therein. A posterior side 1510 of spacer 1502 includes a pair of through-passages 1512, 1514 into void 1509.

Plate 1504 includes parallel through-passages 1516, 1518 extending parallel to each other in a posterior-to-anterior direction such that, when plate 1504 is aligned with spacer 1502, passage 1516 aligns with passage 1412 and passage 14221518 aligns with passage 1514.

Insertion device 1506 includes a pair of fingers 1520, 1522, each of which extends through one of through-passages 1516, 1518 and one of through-passages 1512, 1514 and into void 1509. Each finger 1520, 1522 includes a laterally extending lip 1524, 1526, respectively.

When two prongs of an insertion device (not shown) are inserted into through-passages 1516, 1518 and 1512, 1514, with the prongs on medial sides of each of fingers 1520, 1522, fingers 1520, 1522 are biased laterally so that lips 1524, 1526 engage the posterior wall of void 1509, temporarily securing plate 1504 to spacer 1502 for insertion. After insertion, when the insertion device 1506 is removed, fingers 1520, 1522 bias back toward each other so that plate 1504 is no longer secured to spacer 1502 and spacer 1502 and plate 1504 are two separate entities.

Figure 122:
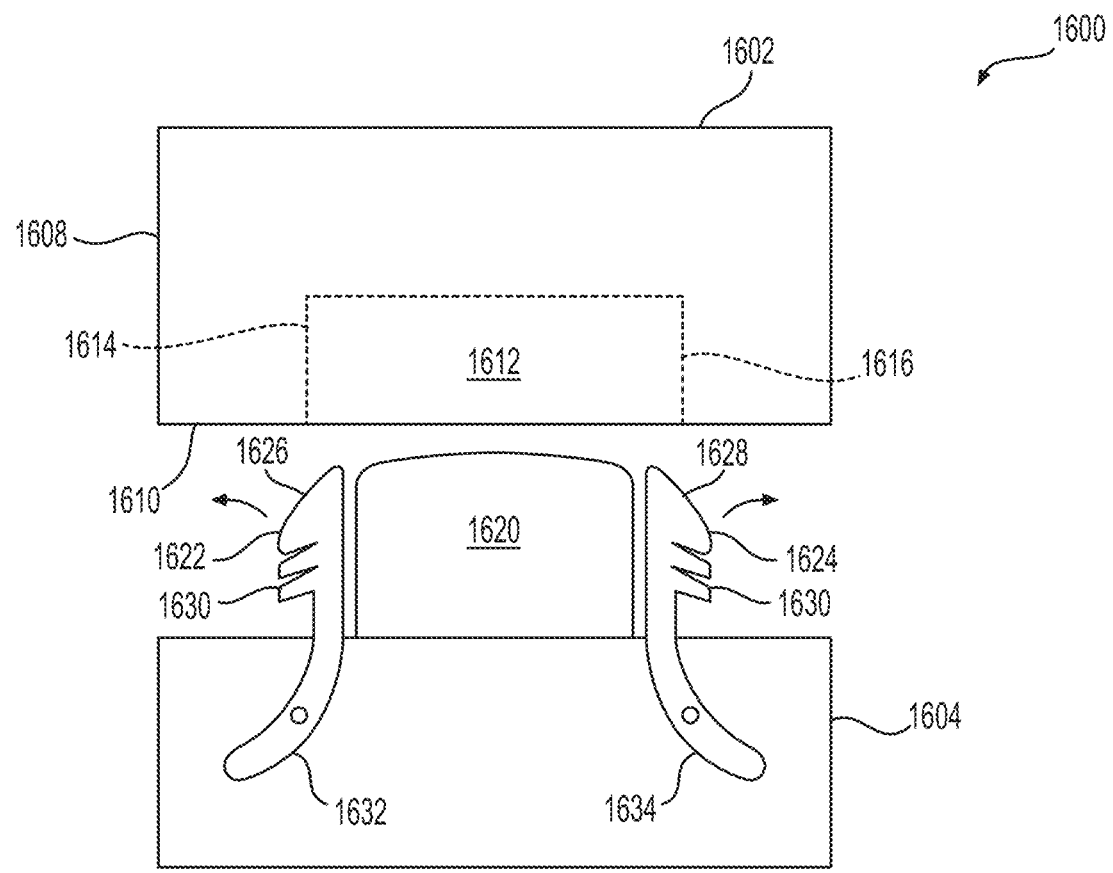

Referring now to FIG. 122, an alternative embodiment of an intervertebral spacer and plate assembly 1600 ("assembly 1600") is shown. Assembly 1600 includes a spacer 1602 and a plate 1604. Spacer 1602 includes a body 1608. A posterior side 1610 of spacer 1602 includes a blind slot 1612 extending into body 1608. Slot 1612 includes lateral sidewalls 1614, 1616.

Plate 1604 includes a tab 1620 sized to fit into slot 1612 with lateral space on either side of tab 1620 to accommodate fingers 1622, 1624. Biased fingers 1622, 1624 are pivotally connected to spacer 1604 with anterior ends 1626, 1628 having a plurality of laterally extending fingers 1630. Posterior ends 1632, 1634 of fingers 1622, 1624 are engageable by an insertion device (not shown)

During insertion, fingers 1622, 1624 are against lateral sidewalls 1614, 1616 of slot 1612 so that plate 1604 is engaged with spacer 1602. Fingers 1630 compress toward their respective fingers 1622, 1624, wedging spacer 1604 into spacer 1602. After assembly 1600 is inserted, the insertion device is removed, allowing fingers 1622, 1624 to bias away from sidewalls 1614, 1616, respectively, releasing spacer 1602 from plate 1604.

Figure 123:
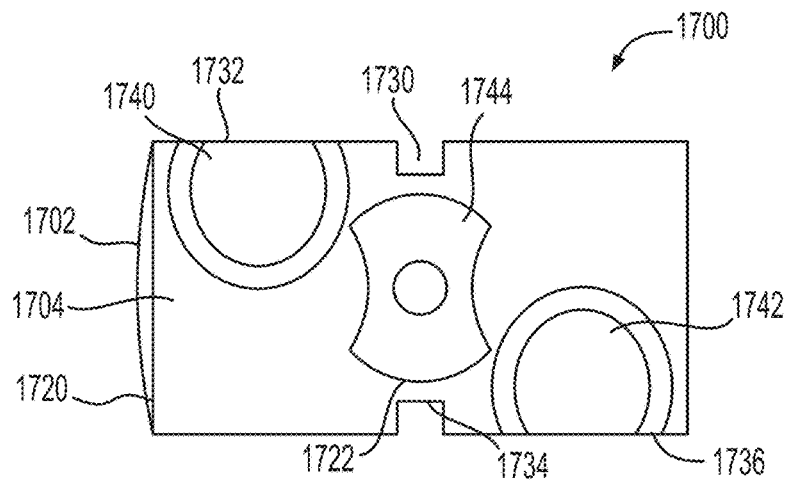
Figure 124:
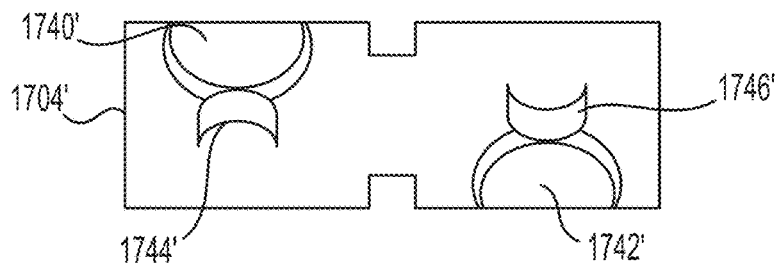
Figure 125:
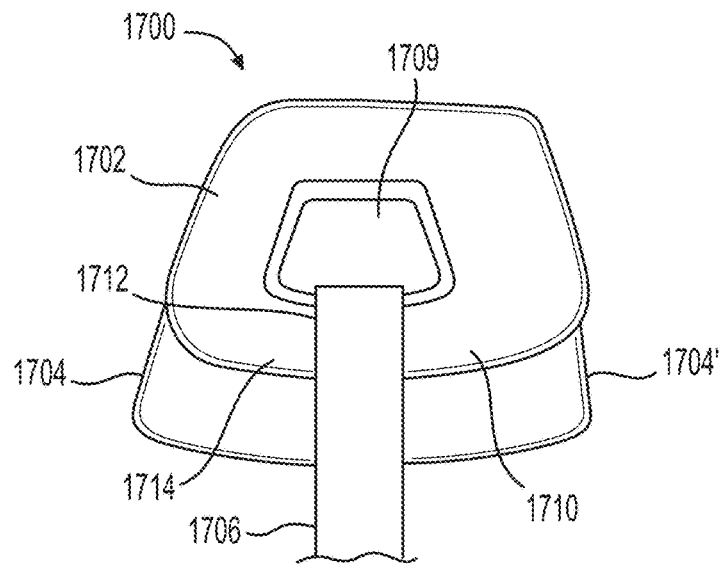

Referring now to FIGS. 123-125, an alternative embodiment of an intervertebral spacer and plate assembly 1700 ("assembly 1700") is shown. Assembly 1700 includes a spacer 1702 and a plate 1704. Spacer 1702 includes a body 1708 having a central void 1709 formed therein. A superior surface 1710 of spacer 1702 includes a central slot 1712 extending along a posterior surface 1714 to void 1709. Similarly, an inferior surface 1720 includes a corresponding slot 1722.

Referring to FIG. 123, plate 1704 includes a slot 1730 extending along a top surface 1732 thereof and a slot 1734 extending along a bottom surface 1736 thereof. Plate 1704 includes a pair of screw opening 1740, 1742 and a centrally located blocking screw 1744. An alternative embodiment of a plate 1704', shown in FIG. 124, uses multiple blocking screws 1740', 1744', each for an individual screw opening 1740', 1742', with locking screws 1744', 1746' disposed laterally away from a center of plate 1740' to allow plate 1740' to be thinner than plate 1740 and still be able to secure screws (not shown) in screw openings 1740', 1742'.

FIG. 125 shows in insertion device 1706 gripping both spacer 1702 and either plate 1704 or plate 1704'. Insertion device 1706 extends through slots 1730, 1712 and slots 1734, 1722, securing spacer 1702 and plate 1704, 1704' to securing device 1706. After insertion, insertion device 1704 is slid posteriorly, decupling spacer 1702 and plate 1704, 1704'.

Referring to FIGS. 126 and 127, an alternative embodiment of an intervertebral spacer and plate assembly 1800 ("assembly 1800") is shown. Assembly 1800 includes a spacer 1802 and a plate 1804. Spacer 1802 includes a body 1810 having a posterior portion 1812. Posterior portion 1812 includes a space 1814 that is sized to receive plate 1804. Plate 1804 can be inserted into space 1814 from a posterior direction or from a superior direction.

Spacer 1802 can include connections for an insertion device (not shown) similar to that disclosed with respect to spacer 102, described above. Assembly 1800 can be inserted as a unit and then, after insertion, the insertion device is removed and spacer 1802 and plate 1804 remain as separate components in the patient's spinal column.

Referring to FIGS. 128-130 an alternative embodiment of an intervertebral spacer and plate assembly 1900 ("assembly 1900") is shown. Assembly 1900 includes a spacer 1902 and a plate 1904 or plate 1904'. Spacer 1902 includes a body 1910 having a posterior portion 1912. Posterior portion 1912 includes a threaded opening 1914 that is sized to receive an insertion tool (not shown). Each of plates 1904, 1904' include a threaded connection 1920, 1920' extending therethrough. Threaded connections 1920, 1920' accept a threaded insertion device (not shown) that extends though plate 1904, 1904' and into threaded opening 1914 in plate 1902. The threaded connection between the insertion device and spacer 1902 and plate 1904, 1904' can be loose to provide for articulation during insertion, similar to the movement of a joystick. Once assembly 1900 is inserted, the insertion device is removed, and spacer 1902 and plate 1904, 1904' remain as separate components in the patient's spinal column.

All of spacers 102-1902 described above can be constructed from biocompatible material, such a, for example, bone, PEEK, titanium, with or without surface treatments, and with varying porosity.

In some embodiments, any of the plates and spacers described above can be accompanied by other surgical implants, including rods and screws. One of skill in the art will appreciate that any of the plates and spacers can be used on multiple levels of the spine.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A surgical method comprising:
   (a) attaching a plate to an insertion tool, the insertion tool comprising a first distal finger and a second distal finger, wherein the first distal finger is threaded;
   (b) attaching an intervertebral spacer to the insertion tool, wherein the spacer has a U-shaped body with a first lateral portion and a second lateral portion, wherein the first lateral portion includes a tubular protrusion that defines an internally threaded passage, and the first distal finger is threadedly connected to the internally threaded passage of the tubular protrusion;
   (c) delivering the plate and the intervertebral spacer to a surgical site in a patient via the insertion tool;
   (d) inserting the intervertebral spacer within a disc space;
   (e) attaching the plate to one or more vertebral bodies adjacent the disc space; and
   removing the insertion tool such that the intervertebral spacer and the plate are decoupled from each other at the surgical site
      wherein the insertion tool is configured to be inserted through the plate into the spacer.

2. The method according to claim 1, wherein step (a) further comprises sliding the plate onto each of the first finger and the second finger.

3. The method according to claim 1, wherein the first finger is parallel to the second finger.

4. The method according to claim 1, wherein step (b) comprises attaching the intervertebral spacer to each of the first finger and the second finger.

5. The method according to claim 4, wherein step (b) further comprises threadingly inserting the second finger into the intervertebral spacer.

6. The method according to claim 4, wherein the first finger is bore rod configured to pass into the plate and the second finger includes rod having a threaded end configured to thread into the plate and the intervertebral spacer.

7. The method according to claim 6, wherein step (b) further comprises threading the rod of the second finger into a through-hole of the intervertebral spacer.

8. The method according to claim 1, further comprising the step of (g) inserting graft material into the intervertebral spacer.

9. The method according to claim 1, wherein the plate comprises an anterior surface and wherein the intervertebral spacer comprises a posterior surface and wherein step (b) comprises engaging the anterior surface with the posterior surface.

10. A surgical method comprising:
(a) attaching a plate and an intervertebral spacer to an insertion instrument, wherein the insertion instrument comprises a first distal finger and a second distal finger, and the first distal finger is threaded, and wherein the spacer has a U-shaped body with a first lateral portion and a second lateral portion, the first lateral portion includes a tubular protrusion that defines an internally threaded passage, and the first distal finger is connected to the passage of the tubular protrusion;
(b) delivering the insertion instrument with the plate and the intervertebral spacer to a surgical site; and
(c) implanting the plate and the intervertebral spacer at or near the surgical site, wherein the plate and the intervertebral spacer are not attached to one another following implantation
wherein the insertion tool is configured to be inserted through the plate into the spacer.

11. The method according to claim 10, wherein step (a) is performed in the absence of securing the plate to the intervertebral spacer.

12. The method according to claim 10, wherein the plate comprises a first through-opening and a second through-opening and wherein step (a) comprises inserting the insertion instrument through the first through-opening and the second through-opening and into the intervertebral spacer.

13. The method according to claim 12, wherein step (a) further comprises threading the insertion instrument into the plate.

14. The method according to claim 12, wherein step (a) further comprises threading the insertion tool into the intervertebral spacer.

15. The method according to claim 10, wherein the second distal finger comprises an unthreaded finger and wherein step (a) comprises inserting the unthreaded finger through the plate and into the intervertebral spacer.

16. The method according to claim 10, further comprising the step of (d) removing the insertion instrument such that the intervertebral spacer is separate from the connecting plate.

17. The method according to claim 16, wherein the intervertebral spacer is inserted between two adjacent vertebrae.

18. The method according to claim 10, wherein the intervertebral spacer is implanted in a disc space between two vertebrae and at least a portion of the plate is implanted outside of the disc space.

* * * * *